US012600762B2

(12) United States Patent
Lu et al.

(10) Patent No.: US 12,600,762 B2
(45) Date of Patent: Apr. 14, 2026

(54) MASKED CYTOKINES AND METHODS OF USE THEREOF

(71) Applicant: ASKGENE PHARMA, INC.,
Camarillo, CA (US)

(72) Inventors: Yuefeng Lu, Moorpark, CA (US);
Chunxiao Yu, Santa Barbara, CA (US);
Jian-Feng Lu, Oak Park, CA (US);
Liqin Liu, Woodland Hills, CA (US)

(73) Assignee: ASKGENE PHARMA, INC.,
Camarillo, CA (US)

( * ) Notice: Subject to any disclaimer, the term of this patent is extended or adjusted under 35 U.S.C. 154(b) by 723 days.

(21) Appl. No.: 17/787,741

(22) PCT Filed: Jan. 11, 2021

(86) PCT No.: PCT/US2021/013007
§ 371 (c)(1),
(2) Date: Jun. 21, 2022

(87) PCT Pub. No.: WO2021/142471
PCT Pub. Date: Jul. 15, 2021

(65) Prior Publication Data
US 2023/0108562 A1     Apr. 6, 2023

Related U.S. Application Data

(60) Provisional application No. 63/126,393, filed on Dec. 16, 2020, provisional application No. 63/029,473, filed on May 23, 2020, provisional application No. 63/027,138, filed on May 19, 2020, provisional application No. 62/959,973, filed on Jan. 11, 2020.

(51) Int. Cl.
| | |
|---|---|
| *C07K 14/715* | (2006.01) |
| *C07K 14/54* | (2006.01) |
| *C07K 14/55* | (2006.01) |
| *C07K 16/24* | (2006.01) |
| *C07K 16/28* | (2006.01) |
| *A61K 38/00* | (2006.01) |

(52) U.S. Cl.
CPC .......... *C07K 14/7155* (2013.01); *C07K 14/54* (2013.01); *C07K 14/5418* (2013.01); *C07K 14/5443* (2013.01); *C07K 14/55* (2013.01); *C07K 16/244* (2013.01); *C07K 16/2818* (2013.01); *A61K 38/00* (2013.01); *C07K 2317/622* (2013.01); *C07K 2319/00* (2013.01)

(58) Field of Classification Search
CPC ................ C07K 14/7155; C07K 14/54; C07K 14/5418; C07K 14/5433; C07K 14/55
See application file for complete search history.

(56) References Cited

U.S. PATENT DOCUMENTS

| | | | |
|---|---|---|---|
| 4,411,993 | A | 10/1983 | Gillis |
| 5,229,109 | A | 7/1993 | Grimm et al. |
| 6,682,736 | B1 | 1/2004 | Hanson et al. |
| 6,942,853 | B2 | 9/2005 | Chernajovsky et al. |
| 6,955,807 | B1 | 10/2005 | Shanafelt et al. |
| 6,984,720 | B1 | 1/2006 | Korman et al. |
| 7,008,624 | B1 | 3/2006 | Grabstein et al. |
| 7,153,507 | B2 | 12/2006 | van de Winkel et al. |
| 7,858,081 | B2 | 12/2010 | Bernard et al. |
| 7,943,743 | B2 | 5/2011 | Korman et al. |
| 8,008,449 | B2 | 8/2011 | Korman et al. |
| 8,211,420 | B2 | 7/2012 | Bondensgaard et al. |
| 8,563,697 | B2 | 10/2013 | Clarke et al. |
| 8,642,742 | B2 | 2/2014 | Hofer et al. |
| 8,642,745 | B2 | 2/2014 | Arathoon et al. |
| 9,206,260 | B2 | 12/2015 | Hofer et al. |
| 9,428,567 | B2 | 8/2016 | Garcia et al. |
| 9,447,159 | B2 | 9/2016 | Ast et al. |
| 9,474,780 | B2 | 10/2016 | Bokvist et al. |
| 9,732,134 | B2 | 8/2017 | Gavin et al. |
| 9,822,180 | B2 | 11/2017 | Cobbold et al. |
| 10,035,836 | B1 | 7/2018 | Greve |
| 10,137,195 | B2 | 11/2018 | Sahin et al. |
| 10,301,384 | B2 | 5/2019 | Vicari et al. |
| 10,611,812 | B2 | 4/2020 | Wang et al. |
| 10,800,825 | B2 | 10/2020 | Lee et al. |
| 10,815,303 | B2 | 10/2020 | Yue et al. |
| 10,858,452 | B2 | 12/2020 | Mortier et al. |
| 11,130,806 | B2 | 9/2021 | Vicari et al. |
| 11,267,883 | B2 | 3/2022 | Laine et al. |
| 11,357,820 | B2 | 6/2022 | Corvari et al. |
| 11,459,404 | B2 | 10/2022 | Bacac et al. |
| 11,845,801 | B2 | 12/2023 | Lu et al. |
| 2002/0039581 | A1 | 4/2002 | Carreno et al. |
| 2002/0086014 | A1 | 7/2002 | Korman et al. |
| 2003/0124678 | A1 | 7/2003 | Epstein et al. |

(Continued)

FOREIGN PATENT DOCUMENTS

| | | | |
|---|---|---|---|
| CA | 3083946 A1 | 6/2019 |
| CN | 101426916 A | 5/2009 |

(Continued)

OTHER PUBLICATIONS

Chen et al., "Fusion protein linkers: property, design and functionality," Adv Drug Deliv Rev. (2013) 65(10):1357-69.
Kalim et al., "Prostaglandin E2 inhibits IL-23 and IL-12 production by human monocytes through down-regulation of their common p40 subunit," Mol Immunol. (2013) 53(3):274-82.
Moya et al., "Isolation and characterization of modified species of a mutated (Cys(125)-Ala) recombinant human interleukin-2," J Chromatogr A. (2002) 971(1-2):129-42.

(Continued)

*Primary Examiner* — Prema M Mertz
(74) *Attorney, Agent, or Firm* — Steptoe LLP; Yi Han Dulkeith; Mauricio Alvarez

(57) ABSTRACT

Provided herein are prodrugs and methods of making and using thereof for stimulating the immune system, or treating cancer, autoimmune or an infectious disease.

19 Claims, 13 Drawing Sheets

Figure 1B:
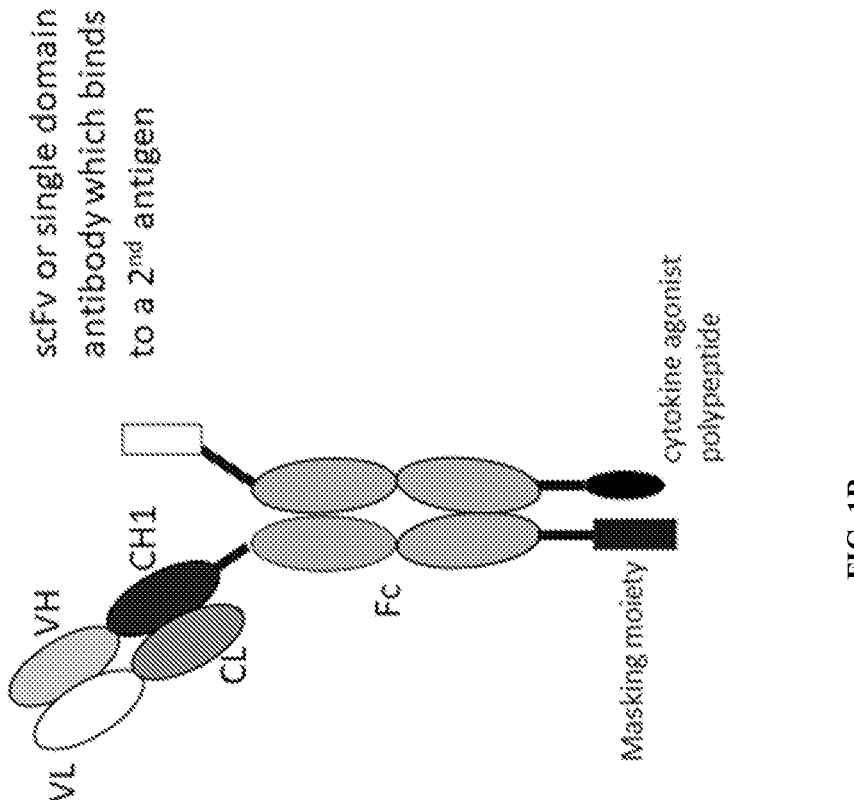

Specification includes a Sequence Listing.

(56) References Cited

U.S. PATENT DOCUMENTS

| | | |
|---|---|---|
| 2004/0053829 A1 | 3/2004 | Pfizenmaier et al. |
| 2005/0201994 A1 | 9/2005 | Korman et al. |
| 2006/0236411 A1 | 10/2006 | Dreher et al. |
| 2006/0269515 A1 | 11/2006 | Denis-Mize et al. |
| 2011/0150892 A1 | 6/2011 | Thudium et al. |
| 2011/0250213 A1 | 10/2011 | Tso et al. |
| 2011/0306752 A1 | 12/2011 | Wittrup et al. |
| 2013/0022623 A1 | 1/2013 | Karsunky et al. |
| 2013/0089516 A1 | 4/2013 | Frelinger et al. |
| 2014/0135482 A1 | 5/2014 | Bossenmaier et al. |
| 2014/0294759 A1 | 10/2014 | Chu et al. |
| 2014/0314709 A1 | 10/2014 | León Monzón et al. |
| 2014/0328791 A1 | 11/2014 | Bossard et al. |
| 2015/0266954 A1 | 9/2015 | Davies et al. |
| 2016/0319256 A9 | 11/2016 | Deming et al. |
| 2016/0340413 A1 | 11/2016 | Duerner et al. |
| 2017/0173149 A1 | 6/2017 | Ettinger et al. |
| 2017/0204154 A1 | 7/2017 | Greve |
| 2017/0240608 A1 | 8/2017 | Stagliano et al. |
| 2017/0306303 A1 | 10/2017 | Taunton et al. |
| 2018/0086849 A1 | 3/2018 | Bacac et al. |
| 2018/0118828 A1 | 5/2018 | Bernett et al. |
| 2019/0046611 A1 | 2/2019 | Ali et al. |
| 2019/0070264 A1 | 3/2019 | Qu et al. |
| 2019/0153471 A1 | 5/2019 | Paul et al. |
| 2019/0367576 A1 | 12/2019 | Winston et al. |
| 2020/0123227 A1 | 4/2020 | Fu et al. |
| 2020/0164069 A1 | 5/2020 | Ettinger et al. |
| 2020/0207846 A1 | 7/2020 | Igawa et al. |
| 2020/0331966 A1 | 10/2020 | Stover et al. |
| 2020/0347128 A1 | 11/2020 | Tagaya et al. |
| 2020/0392235 A1 | 12/2020 | Lu et al. |
| 2021/0163562 A1 | 6/2021 | Lu et al. |
| 2021/0260163 A1 | 8/2021 | Yu et al. |
| 2022/0127352 A1 | 4/2022 | Laine et al. |
| 2022/0162280 A1 | 5/2022 | Fu et al. |
| 2022/0289822 A1 | 9/2022 | Lu et al. |
| 2022/0306714 A1 | 9/2022 | Yao et al. |
| 2022/0356221 A1 | 11/2022 | Lu et al. |
| 2023/0096452 A1 | 3/2023 | Zhou et al. |
| 2024/0067739 A1 | 2/2024 | Lu et al. |
| 2024/0076331 A1 | 3/2024 | Lu et al. |
| 2024/0076355 A1 | 3/2024 | Lu et al. |
| 2025/0051413 A1 | 2/2025 | Yu et al. |
| 2025/0127858 A1 | 4/2025 | Yu et al. |

FOREIGN PATENT DOCUMENTS

| | | | |
|---|---|---|---|
| CN | 110174363 A | 8/2019 | |
| EP | 1870459 A1 | 12/2007 | |
| EP | 2639241 A2 | 9/2013 | |
| EP | 2665486 B1 | 12/2019 | |
| EP | 3093295 B1 | 5/2020 | |
| EP | 3733716 A1 | 11/2020 | |
| NZ | 567242 A | 11/2009 | |
| WO | WO 1999/029732 A2 | 6/1999 | |
| WO | WO 2002/022833 A1 | 3/2002 | |
| WO | WO 2003/017935 A2 | 3/2003 | |
| WO | WO 2003/028630 A2 | 4/2003 | |
| WO | WO 2004/021861 A2 | 3/2004 | |
| WO | WO 2005/063279 A1 | 7/2005 | |
| WO | WO 2005/066348 A2 | 7/2005 | |
| WO | WO 2005/085282 A1 | 9/2005 | |
| WO | WO 2008/003473 A2 | 1/2008 | |
| WO | WO 2009/025846 A2 | 2/2009 | |
| WO | WO 2009/061853 A2 | 5/2009 | |
| WO | WO 2010/040105 A2 | 4/2010 | |
| WO | WO 2012/061536 A2 | 5/2012 | |
| WO | WO 2012/099886 A1 | 7/2012 | |
| WO | WO 2012/107417 A1 | 8/2012 | |
| WO | WO 2012/120125 A1 | 9/2012 | |
| WO | WO 2012/146628 A1 | 11/2012 | |
| WO | WO 2014/066527 A2 | 5/2014 | |
| WO | WO 2014/164553 A1 | 10/2014 | |
| WO | WO 2015/066279 A2 | 5/2015 | |
| WO | WO 2015/110930 A1 | 7/2015 | |
| WO | WO 2016/001275 A1 | 1/2016 | |
| WO | WO 2016/014428 A2 | 1/2016 | |
| WO | WO 2016/082677 A1 | 6/2016 | |
| WO | WO 2016/086186 A2 | 6/2016 | |
| WO | WO 2016/090173 A1 | 6/2016 | |
| WO | WO 2016/112497 A1 | 7/2016 | |
| WO | WO 2016/115275 A1 | 7/2016 | |
| WO | WO 2016/200645 A1 | 12/2016 | |
| WO | WO 2017/013203 A1 | 1/2017 | |
| WO | WO 2017/046200 A1 | 3/2017 | |
| WO | WO 2017/162587 A1 | 9/2017 | |
| WO | WO 2017/201432 A2 | 11/2017 | |
| WO | WO 2017/220989 A1 | 12/2017 | |
| WO | WO 2018/004338 A1 | 1/2018 | |
| WO | WO 2018/119246 A1 | 6/2018 | |
| WO | WO 2018/191438 A1 | 10/2018 | |
| WO | WO 2019/137541 | 7/2019 | |
| WO | WO 2019/173832 A2 | 9/2019 | |
| WO | WO 2019/174617 A1 | 9/2019 | |
| WO | WO 2019/222296 A1 | 11/2019 | |
| WO | WO 2019/246392 A1 | 12/2019 | |
| WO | WO 2020/069398 A1 | 4/2020 | |
| WO | WO 2020/227019 A1 | 11/2020 | |
| WO | WO 2020/242884 A1 | 12/2020 | |
| WO | WO 2020/247843 A2 | 12/2020 | |
| WO | WO 2022/032003 A2 | 2/2022 | |
| WO | WO 2022/159395 A1 | 7/2022 | |
| WO | WO 2022/178103 | 8/2022 | |
| WO | WO 2022/221746 A1 | 10/2022 | |
| WO | WO 2023/044290 A1 | 3/2023 | |
| WO | WO 2024/119193 A2 | 6/2024 | |
| WO | WO 2024/252184 | 12/2024 | |
| WO | WO 2025/122660 | 6/2025 | |

OTHER PUBLICATIONS

Robinson et al., "The potential and promise of IL-15 in immuno-oncogenic therapies." Immunol Lett. (2017) 190:159-168.

Adoro et al., "IL-21 induces antiviral microRNA-29 in CD4 T cells to limit HIV-1 infection," Nature Communications 6:7562 (12 pages) (2015).

Bazan, "Unraveling the structure of IL-2," Science 257:410-13 (1992).

Bernard et al., "Identification of an interleukin-15alpha receptor-binding site on human interleukin-15," J Biol Chem. 279:24313-22 (2004).

Bogdan et al., "Macrophage deactivation by interleukin 10," J Exp Med. 174(6):1549-55 (1991).

Booty et al., "IL-21 signaling is essential for optimal host resistance against *Mycobacterium tuberculosis* infection," Nature, Scientific Reports 6:36720 (13 pages) (2016).

Charych et al., "Modeling the receptor pharmacology, pharmacokinetics, and pharmacodynamics of NKTR-214, a kinetically-controlled interleukin-2 (IL2) receptor agonist for cancer immunotherapy," PLoS One 12(7) (2017).

Chothia et al., "Canonical structures for the hypervariable regions of immunoglobulins," J. Mol. Biol. 96(4):901-17 (1987).

Colombo et al., "Interleukin-12 in anti-tumor immunity and immunotherapy," Cytokine Growth Factor Rev. 13(2):155-68 (2002).

Conlon et al., "IL15 by Continuous Intravenous Infusion to Adult Patients with Solid Tumors in a Phase I Trial Induced Dramatic NK-Cell Subset Expansion," Clin Cancer Res. 25(16):4945-4954 (2019).

Del Vecchio et al., "Interleukin-12: biological properties and clinical application," Clin Cancer Res. 13(16):4677-85 (2007).

Dall'Acqua et al., "Properties of human IgG1s engineered for enhanced binding to the neonatal Fc receptor (FcRn)," J Biol Chem. 281: 23514-24 (2006).

De Waal Malefyt et al., "Interleukin 10 (IL-10) and viral IL-10 strongly reduce antigen-specific human T cell proliferation by diminishing the antigen-presenting capacity of monocytes via downregulation of class II major histocompatibility complex expression," J Exp Med. 174(4):915-24 (1991).

(56)            References Cited

OTHER PUBLICATIONS

Database UniProt [Online] RecName: Full=High affinity IL-2 receptor subunit beta {ECO:00002561 ARBA:ARBA00014194}; retrieved from EBI accession No. UNIPROT:A0A2K6RLA0; Database accession No. A0A2K6RLA0; the whole document.

DiSanto et al., "Interleukin-2 (IL-2) receptor gamma chain mutations in X-linked severe combined immunodeficiency disease result in the loss of high-affinity IL-2 receptor binding," Eur J Immunol. 24(2):475-9 (1994).

Donaldson et al., "Design and development of masked therapeutic antibodies to limit off-target effects: application to anti-EGFR antibodies," Cancer Biol Ther. 8(22):2147-52 (2009).

Fiorentino et al., "IL-10 acts on the antigen-presenting cell to inhibit cytokine production by Th1 cells," J Immunol. 146(10):3444-51 (1991).

Fontenot et al., "A function for interleukin 2 in Foxp3-expressing regulatory T cells," Nature Immunol 6:1142-51 (2005).

Gelebart et al., "Interleukin-21 effectively induces apoptosis in mantle cell lymphoma through a STAT1-dependent mechanism," Leukemia 23:1836-1846 (2009).

Gharibi et al., "Biological effects of IL-21 on different immune cells and its role in autoimmune diseases," Immunobiology 221(2):357-67 (2016).

Giri et al., "Utilization of the beta and gamma chains of the IL-2 receptor by the novel cytokine IL-15," EMBO J. 13:2822-30 (1994).

Giri et al., "IL-15, a novel T cell growth factor that shares activities and receptor components with I L-2," J Leukoc Biol. 57:763-6 (1995).

Grimm et al., p. 25, Abstr 5861 (2016) [www.page-meeting.org/?abstract=5861].

Guo et al., "Immunobiology of the IL-15/IL-15Ra complex as an antitumor and antiviral agent," Cytokine Growth Factor Rev 38:10-21 (2017).

Harrington et al., "Modulation of immune checkpoint molecule expression in mantle cell lymphoma," Leuk Lymphoma 60(10):2498-2507 (2019).

Heaton et al. "Human interleukin 2 analogues that preferentially bind the intermediate-affinity interleukin 2 receptor lead to reduced secondary cytokine secretion: implications for the use of these interleukin 2 analogues in cancer immunotherapy," Cancer Res. 53(11):2597-602 (1993).

Hezareh et al. "Effector function activities of a panel of mutants of a broadly neutralizing antibody against human immunodeficiency virus type 1," J. Virol. 75(24):12161-8 (2001).

Holcomb et al., "A forced marriage of IL-2 and PD-1 antibody nurtures tumor-infiltrating T cells," J Clin Invest. 132(3):e156628 (2022).

Hsu et al., "A cytokine receptor-masked IL2 prodrug selectively activates tumor-infiltrating lymphocytes for potent antitumor therapy," Nature Communications, vol. 12, No. 1 (2021).

Hutmacher et al., "Antibody-cytokine fusion proteins: Biopharmaceuticals with immunomodulatory properties for cancer therapy," Adv Drug Deliv Rev. 141:67-91 (2019).

Johnson et al., "Soluble IL-2 receptor beta and gamma subunits: ligand binding and cooperativity," Eur Cytokine Netw. 5(1):23-34 (1994).

Jounaidi et al., "Tethering IL2 to Its Receptor IL2RB Enhances Antitumor Activity and Expansion of Natural Killer NK92 Cells," Cancer Research, vol. 77 ( 21) 5938-5951 (2017).

Kang et al., "Rational design of interleukin-21 antagonist through selective elimination of the gammaC binding epitope," J Biol Chem. 285(16):12223-31 (2010).

Kim et al., "Both integrated and differential regulation of components of the IL-2/IL-2 receptor system," Cytokine Growth Factor Rev. 17:349-66 (2006).

Kirwood, "Cancer immunotherapy: the interferon-alpha experience," Semin Oncol. 29(3 Suppl 7):18-26 (2002).

Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology 6(3):e1277306 (2017).

Korn et al., "IL-21 initiates an alternative pathway to induce proinflammatory T(H)17 cells," Nature 448(7152):484-87 (2007).

Krieg et al., "Improved IL-2 immunotherapy by selective stimulation of IL-2 receptors on lymphocytes and endothelial cells," Proc Natl Acad Sci. 107:11906-11 (2010).

Kuen et al., "Antibody masked cytokines as new approach in targeted tumor therapy," (2018) (Doctoral Thesis). XP055702405.

Lasek et al., "Interleukin 12: still a promising candidate for tumor immunotherapy?" Cancer Immunol Immunother. 63(5):419-35 (2014).

Lehours et al., "Subunit structure of the high and low affinity human interleukin-15 receptors," Eur Cytokine Netw. 11:207-15 (2000).

Lopes et al., "ALKS 4230: a novel engineered IL-2 fusion protein with an improved cellular selectivity profile for cancer immunotherapy," J Immunother Cancer. 8(1) (2020).

Macatonia et al., "Differential effect of IL-10 on dendritic cell-induced T cell proliferation and IFN-gamma production," J Immunol. 150(9):3755-65 (1993).

McDonald et al., "Interleukin 2-Based Fusion Proteins for the Treatment of Cancer," Journal of Immunology Research, vol. 2021 pp. 1-11 (2021).

Marth et al., "Interferon-gamma in combination with carboplatin and paclitaxel as a safe and effective first-line treatment option for advanced ovarian cancer: results of a phase I/II study," Int. J. Gynecol. (Cancer) 16:1522-1528 (2006).

Mehta et al., "Biology of IL-21 and the IL-21 receptor," Immunol Rev. 202:84-95 (2004).

Merchant et al., "An efficient route to human bispecific IgG," Nature Biotech 16:677-81 (1998).

Minami et al., "The IL-2 receptor complex: its structure, function, and target genes," Annu Rev Immunol. 11:245-68 (1993).

Mitra et al., "Interleukin-2 activity can be fine tuned with engineered receptor signaling clamps," Immunity 42(5):826-38 (2015).

Moretto et al., "IL-21 is important for induction of KLRG1+ effector CD8 T cells during acute intracellular infection," J Immunol. 196(1): 375-384 (2016).

Mullard, "Restoring IL-2 to its cancer immunotherapy glory," Nat Rev Drug Discov. 20(3):163-165 (2021).

Nurieva et al., "Essential autocrine regulation by IL-21 in the generation of inflammatory T cells," Nature 448(7152):480-83 (2007).

Ortiz-Sanchez et al., "Antibody-cytokine fusion proteins: applications in cancer therapy," Expert Opin Biol Ther. 8(5): 609-632 (2008).

Parkin et al., "An overview of the immune system," Immunology 357(9270):1777-89 (2001).

Pettit et al., "Structure-Function Studies of Interleukin 15 using Site-specific Mutagenesis, Polyethylene Glycol Conjugation, and Homology Modeling," J Biol Chem. 272: 2312-18 (1997).

Publicover et al., "IL-21 is pivotal in determining age-dependent effectiveness of immune responses in a mouse model of human hepatitis B," J Clin Invest. 121(3):1154-62 (2011).

Puskas et al., "Development of an attenuated interleukin-2 fusion protein that can be activated by tumour-expressed proteases," Immunology 133:206-220 (2011).

Raeber et al., "A systematic review of interleukin-2-based immunotherapies in clinical trials for cancer and autoimmune diseases," eBioMedicine 90:104539 (25 pages) (2023).

Robbie et al., "A novel investigational Fc-modified humanized monoclonal antibody, motavizumab-YTE, has an extended half-life in healthy adults," Antimicrob Agents Chemother. 57(12):6147-53 (2013).

Rosen et al., "TransCon IL-2 β/γ: a novel long-acting prodrug with sustained release of an IL-2Rβ/γ-selective IL-2 variant with improved pharmacokinetics and potent activation of cytotoxic immune cells for the treatment of cancer," J Immunother Cancer. 10(7) (2022):e004991 (14 pages).

Sanjabi et al., "Regulation of the Immune Response by TGF-β: From Conception to Autoimmunity and Infection," Cold Spring Harb Perspect Biol. 9(6) (2017).

(56)                   References Cited

OTHER PUBLICATIONS

Schmidt et al., "Safety and Clinical Effect of Subcutaneous Human Interleukin-21 in Patients with Metastatic Melanoma or Renal Cell Carcinoma: A Phase I Trial," Clin Cancer Res. 16(21):5312-19 (2010).

Shen et al., "Engineered IL-21 cytokine muteins fused to anti-PD-1 antibodies can improve CD8+ T cell function and anti-tumor immunity," Front Immunol. 11:832 (2020).

Singh et al., "Anti-claudin 18.2 antibody as new targeted therapy for advanced gastric cancer," J Hematol Oncol. (2017) 10(1):105).

Skrombolas et al., "Development of an Interleukin-12 Fusion Protein That Is Activated by Cleavage with Matrix Metalloproteinase 9," J Interferon Cytokine Res. 39(4):233-245 (2019).

Smith, "Interleukin-2: inception, impact, and implications," Science 240:1169-76 (1988).

Sockolosky et al., "Selective targeting of engineered T cells using orthogonal IL-2 cytokine-receptor complexes," Science. 359(6379):1037-1042 (2018).

Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," J Clin Onc. 36:15 suppl (2018).

Sogkas et al., "First Association of Interleukin 12 Receptor Beta 1 Deficiency with Sjogren's Syndrome," Front Immunol. 8:885 (2017).

Spiess et al., "Alternative molecular formats and therapeutic applications for bispecific antibodies," Mol Imm. 67(2)(A):95-106 (2015).

Spolski et al., "The Yin and Yang of Interleukin-21 in Allergy, Autoimmunity and Cancer," Curr Opin Immunol. 20(3): 295-301 (2008).

Spolski et al., "Interleukin-21: basic biology and implications for cancer and autoimmunity," Annu Rev Immunol. 26:57-79 (2008).

Stauber et al., "Crystal structure of the IL-2 signaling complex: paradigm for a heterotrimeric cytokine receptor," Proc Natl Acad Sci U S A. 103(8):2788-93 (2006).

Tam et al., "Functional, Biophysical, and Structural Characterization of Human IgG1 and IgG4 Fc Variants with Ablated Immune Functionality," Antibodies 6(12):1-34 (2017).

Vazquez-Lombardi et al., "Molecular Engineering of Therapeutic Cytokines," Antibodies 2(3), 426-451 (2013).

Wang et al., "Structure of the quaternary complex of interleukin-2 with its alpha, beta, and gammac receptors," Science 310:1159-63 (2005).

Wang et al., "Targeting IL-10 Family Cytokines for the Treatment of Human Diseases," Cold Spring Harb Perspect Biol. 11(2):a028548 (2019).

Watford et al., "The biology of IL-12: coordinating innate and adaptive immune responses," Cytokine Growth Factor Rev. 14(5):361-8 (2003).

Weerd et al. "Type I interferon receptors: biochemistry and biological functions," The Journal of Biological Chemistry 282 (28): 20053-7 (2007).

Wei et al., "The Sushi domain of soluble IL-15 receptor alpha is essential for binding IL-15 and inhibiting inflammatory and allogenic responses in vitro and in vivo," J Immunol. 167(1):277-82 (2001).

Weidle et al., "Proteases as activators for cytotoxic prodrugs in antitumor therapy," Cancer Genomics Proteomics. 11(2):67-80 (2014).

Worthington et al., "Regulation of TGFβ in the immune system: an emerging role for integrins and dendritic cells," Immunobiology 217(12):1259-65 (2012).

Wüest et al., "TNF-Selectokine: a novel prodrug generated for tumor targeting and site-specific activation of tumor necrosis factor," Oncogene. 21(27):4257-65 (2002).

Ye et al., "Targeting IL-2: an unexpected effect in treating immunological diseases," Signal Transduct Target Ther. 3:2 (2018).

Young et al., "Antibody-cytokine fusion proteins for treatment of cancer: engineering cytokines for improved efficacy and safety," Semin Oncol. 41(5): 623-636 (2014).

Zarkavelis et al., "The emerging role of Interleukin-21 as an antineoplastic immunomodulatory treatment option," Transl Cancer Res. 6(Suppl 2):S328-30 (2017).

Zhang et al., "Human IL-21 and IL-4 bind to partially overlapping epitopes of common gamma-chain," Biochem Biophys Res Commun. 300(2):291-6 (2003).

Zhang et al., "A phase I/II study of ASKB589 (anti-claudin 18.2 [CLDN18.2] monoclonal antibody) in patients with solid tumors," Journal of Clinical Oncology 41(4 suppl):397-397 (2023).

Zhu et al., "Novel Human Interleukin-15 Agonists," J Immnol. 183(6):3598 (2009).

scFv or single domain antibody which binds to a 2nd antigen

| | PD-1+ T cell (EC$_{50}$ µg/mL) | PD-1- T cells (EC$_{50}$ µg/mL) | Potency Fold Change (EC$_{50}$ PD-1- / EC$_{50}$ PD-1+) |
|---|---|---|---|
| PD-1 | >10,000 | >10,000 | N/A |
| 215β Ref | 1.12 | 5.72 | 5 x ↑ |
| 215β | 38.48 | 20 | 2 x ↓ |
| 215γ | 2.47 | 195 | 79 x ↑ |
| PD1/IL15 mutein (M2) | 0.14 | 6.25 | 44 x ↑ |

FIG. 5C

FIG. 6B

MASKED CYTOKINES AND METHODS OF USE THEREOF

CROSS REFERENCE TO RELATED APPLICATIONS

The application is a national stage application under 35 U.S.C. § 371 of International Patent Application No. PCT/US2021/013007, filed on Jan. 11, 2021, which claims priority from U.S. Provisional Applications 62/959,973, filed Jan. 11, 2020; 63/027,138, filed May 19, 2020; 63/029,473, filed May 23, 2020; and 63/126,393, filed Dec. 16, 2020. The disclosures of the aforementioned priority applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 11, 2021, is named 025471_WO008_SL.txt and is 240,322 bytes in size.

BACKGROUND OF THE INVENTION

Interleukin (IL)-2, IL-4, IL-7, IL-9, IL-15, and IL-21 play important roles in the proliferation, differentiation, and survival of immune cells. The receptors for these cytokines share a common γ chain (γC), also known as CD132. Thus, these cytokines are also called common γC family cytokines.

IL-2 plays a central role in lymphocyte generation, survival, and homeostasis. It has 133 amino acids and consists of four antiparallel, amphipathic alpha-helices that form a quaternary structure essential for its function (Smith, Science (1988) 240:1169-76; Bazan, Science (1992) 257:410-13). IL-2 exerts its activities by binding to IL-2 receptors (IL-2R), which consist of up to three individual subunits. Association of the α (CD25 or Tac antigen), β(CD122), and γC subunits results in a trimeric, high-affinity receptor for IL-2 ($K_D$~0.01 nM). Dimeric IL-2 receptor consisting of the β and γ subunits is termed intermediate-affinity IL-2R ($K_D$~1 nM). The a subunit alone forms the monomeric low affinity IL-2 receptor ($K_D$~10 nM). See, e.g., Kim et al., Cytokine Growth Factor Rev. (2006) 17:349-66). Although the dimeric intermediate-affinity IL-2 receptor binds IL-2 with approximately 100-fold lower affinity than the trimeric high-affinity receptor, both the dimeric and trimeric IL-2 receptors can transmit signal upon IL-2 binding (Minami et al., Annu Rev Immunol. (1993) 11:245-68).

IL-15 is a cytokine with structural similarities to IL-2. IL-15 is secreted by mononuclear phagocytes and other immune cells following viral infection. IL-15 induces proliferation of natural killer (NK) and other cells of the immune system and is involved in the killing of virally infected cells and cancer cells. Like IL-2, IL-15 binds to the IL-2 receptor (IL-2R) β/γ complex, the intermediate affinity receptor, with a $K_D$ of about 1 nM (Giri et al., EMBO J. (1994) 13:2822-30). IL-15 binds to IL-15 receptor (IL-15R) a with a much higher affinity ($K_D$~0.05 nM). IL-15Rα can associate with the IL-2Rβ/γ complex to form an IL-15-specific, functional high-affinity (αβγ) receptor (Minami et al., Annu. Rev. Immunol. (1993) 11:245-67; Giri et al., J Leukoc Biol. (1995) 5745:763-6; and Lehours et al., Eur Cytokine Netw. (2000) 11:207-15).

IL-21 is produced by activated CD4[+] T cells, T-follicular helper cells, and natural killer T (NKT) cells (Spolski and Leonard, Ann Rev Immunol. (2008) 26:57008). IL-21 has been shown to exert pleiotropic effects on the proliferation, differentiation, and cytotoxicity of various classes of lymphoid cells. More recently, IL-21 has been further shown to play a crucial role in the differentiation of CD4[+] T cells into T-helper 17 ($TH_{17}$) cells, a subset of T cells associated with development of inflammatory conditions and autoimmune diseases (Korn et al., Nature (2007) 448(7152):484-87; Nurieva et al., Nature (2007) 448(7152):480-83). The receptor complex of IL-21 is composed of the private chain IL-21Rα and the common chain γC (or Ry). Human IL-21 binds to IL-21Rα with a very high affinity ($K_D$~70 pM; Zhang et al., Biochem Biophys Res Commun. (2003) 300 (2):291-6), while binding to IL-21Rγ with a relatively low affinity ($K_D$~160 µM).

The above cytokines, their muteins, and fusion proteins have been investigated for their potential as therapeutics, with recombinant IL-2 being the first cytokine approved for cancer therapy. However, these cytokine drugs and drug candidates have significant side effects. In addition, their in vivo half-lives are often short, even when presented as antibody-cytokine fusion molecules, potentially due to the "PK sink" formed by the receptors of the cytokines on the immune cells.

Thus, there remains a need to develop cytokine-based cancer therapeutics that are more tumor site-selective and have improved PK and efficacy, while causing fewer side effects.

SUMMARY OF THE INVENTION

The present disclosure provides a prodrug comprising a cytokine moiety, a masking moiety, and a carrier moiety, wherein the masking moiety binds to the cytokine moiety and inhibits a biological activity of the cytokine; the carrier moiety comprises an antigen-binding moiety that binds to an antigen expressed on the surface of a target cell; and the masking moiety is linked to the carrier moiety without a cleavable peptide linker (e.g., linked indirectly to the carrier moiety, through a non-cleavable peptide linker; or directly, without a peptide linker).

In some embodiments, the prodrug is activated by cells that express on the cell surface both the antigen and a receptor for the cytokine moiety. In some embodiments, the biological activity of the prodrug is increased by at least 2, 5, or 10 folds at a disease site comprising the cells as compared to a site not comprising the cells. In particular embodiments, the receptor for the cytokine moiety comprises two or more subunits.

In some embodiments, the antigen is selected from PD-1, PD-L1, CTLA-4, TIGIT, TIM-3, LAG-3, CD25, CD16a, CD16b, NKG2D, NKP44, NKP30, CD19, CD20, CD30, CD38, BCMA, and signal regulatory protein alpha (SIRP alpha, designated CD172a).

In some embodiments, the cytokine moiety comprises an IL-2 agonist polypeptide, an IL-7 agonist polypeptide, an IL-9 agonist polypeptide, an IL-15 agonist polypeptide, an IL-21 agonist polypeptide, an IL-1α agonist polypeptide, an IL-1β agonist polypeptide, an IL-4 agonist polypeptide, an IL-5 agonist polypeptide, an IL-6 agonist polypeptide, an IL-8 agonist polypeptide, an IL-10 agonist polypeptide, an IL-12 agonist polypeptide, an IL-17 agonist polypeptide, an IL-18 agonist polypeptide, an IL-22 agonist polypeptide, an IL-23 agonist polypeptide, an IL-31 agonist polypeptide, an IL-33 agonist polypeptide, an IL-36 agonist polypeptide, an interferon-alpha agonist polypeptide, an interferon gamma agonist polypeptide, a 4-1BB ligand, an OX-40 ligand, or a CD-40 ligand.

In some embodiments, the cytokine moiety comprises an IL-2 agonist polypeptide or an IL-15 agonist polypeptide and the masking moiety comprises an ECD of IL-2 receptor β(IL-2βECD) or a functional fragment thereof. In additional embodiments, the cytokine moiety comprises an IL-21 agonist polypeptide and the masking moiety comprises a Fab, a single chain Fv (scFv), or a single domain antibody against IL-21. In other embodiments, the cytokine moiety comprise an IL-2 agonist polypeptide and the masking moiety comprises a Fab, an scFv, or a single domain antibody against IL-2. In additional embodiments, the cytokine moiety comprises an IL-15 agonist polypeptide, and the masking moiety comprises a Fab, an scFv, or a single domain antibody against IL-15. In other embodiments, the cytokine moiety comprises an IL-15 agonist polypeptide, and the masking moiety comprises a sushi domain of IL-15 receptor α(IL-15Rα sushi domain).

In some embodiments, the cytokine moiety comprises an IL-21 agonist polypeptide comprising SEQ ID NO: 1, or an amino acid sequence at least 90% identical thereto. In other embodiments, the cytokine moiety comprises an IL-2 agonist polypeptide comprising SEQ ID NO: 6 or 62, or an amino acid sequence at least 95% identical thereto. In other embodiments, the cytokine moiety comprises an IL-15 agonist polypeptide comprising SEQ ID NO: 7, or an amino acid sequence at least 95% identical thereto.

In some embodiments, the masking moiety comprises an extracellular domain (ECD) of a receptor of the cytokine. In particular embodiments, the cytokine moiety comprises an IL-7 agonist polypeptide and the masking moiety comprises an ECD of IL-7 receptor α(IL-7Rα ECD) or a functional analog thereof. In particular embodiments, the cytokine moiety is an IL-21 agonist polypeptide and the masking moiety comprises an ECD of IL-21 receptor α(IL-21Rα ECD) or a functional analog thereof. In particular embodiments, the masking moiety comprises an IL-21Rα ECD or a functional analog thereof comprising an amino acid sequence selected from SEQ ID NO: 12, 13, and 63-73, or at least 90% (e.g., at least 95%) identical thereto. In some embodiments, the masking moiety comprises an IL-2β ECD or a functional analog thereof comprising SEQ ID NO: 11, or an amino acid sequence at least 95% identical thereto.

In some embodiments, the masking moiety comprises an scFv that binds the cytokine moiety and inhibits or interferes with the interaction between the cytokine moiety and its receptors. In particular embodiments, the masking moiety is an scFv that binds to human IL-21 and comprises an amino acid sequence of SEQ ID NO: 20 or 21. In particular embodiments, the masking moiety comprises an scFv that binds to IL-2 and inhibits or interferes with the interaction between IL-2 and IL-2Rα, the interaction between IL-2 and IL-2Rβ, and/or the interaction between IL-15 and IL-2Rγ, optionally wherein the scFv comprises the heavy chain and light chain CDRs of antibody 4E12B2D10. In some embodiments, the scFv comprises the heavy chain and light chain of antibody 4E12B2D10. In particular embodiments, the heavy chain and light chain amino acid sequences of 4E12B2D10 comprise SEQ ID NO: 60 and 61, respectively. In some embodiments, the masking moiety is an scFv that binds to IL-2 and comprises an amino acid sequence of SEQ ID NO: 22 or 23, or at least 95% identical as that of SEQ ID NO: 22 or 23. In particular embodiments, the masking moiety comprises an scFv that binds to IL-15 and inhibits or interferes with the interaction between IL-15 and IL-2RB, and/or the interaction between IL-2 and IL-2Ry, optionally wherein the scFv comprises the heavy chain and light chain CDRs of anti-IL-15 antibody 146B7, 146H5, or 404E4, or optionally wherein the scFv comprises the heavy chain and light chain of anti-IL-15 antibody 146B7, 146H5, or 404E4, or optionally wherein the scFv comprises SEQ ID NO: 18 or 19. In some embodiments, an scFv or Fab IL-15 antagonist comprises heavy chain CDR1-3 of an anti-IL-15 antibody selected from 146B7, 146H5, and 404E4; and the light chain CDR1-3 of anti-IL-15 antibody selected from 146B7, 146H5, and 404E4 all of which are described in described in WO2003/017935A2.

In particular embodiments, the masking moiety comprises an scFv that binds to IL-21 and inhibits or interferes with the interaction between IL-21 and IL-21Rα, and/or the interaction between IL-21 and IL-2Rγ. In particular embodiments, the masking moiety comprises an scFv that binds to a cytokine selected from IL-2, IL-7, IL-9, IL-15, or IL-21 and inhibits or interferes with the interaction between the cytokine and IL-2Rγ.

In some embodiments, the prodrug has a half-life in a non-human primate or a human that is at least 20 times, at least 50 times, at least 100 times, at least 150 times, or at least 200 times longer than that of the corresponding wild type cytokine.

In particular embodiments, the prodrug comprises two light chains with an amino acid sequence of SEQ ID NO: 44, and two heavy chain polypeptide chains whose amino acid sequences respectively comprise SEQ ID NOs: 24 and 25; SEQ ID NOs: 35 and 36; SEQ ID NOs: 37 and 36; SEQ ID NOs: 37 and 38; SEQ ID NOs: 39 and 41; or SEQ ID NOs: 42 and 43.

In particular embodiments, the prodrug comprises two light chains with an amino acid sequence of SEQ ID NO: 50, and two heavy chain polypeptide chains whose amino acid sequences respectively comprise SEQ ID NOs: 51 and 54; SEQ ID NOs: 51 and 55; SEQ ID NOs: 51 and 56; SEQ ID NOs: 52 and 54; SEQ ID NOs: 53 and 58; SEQ ID NOs: 53 and 59; or SEQ ID NOs: 52 and 57.

In some embodiments, the present disclosure provides a pharmaceutical composition comprising the prodrug of the present disclosure and a pharmaceutically acceptable excipient.

In some aspects, the present disclosure provides a polynucleotide or polynucleotides encoding the present prodrugs, expression vectors comprising the polynucleotides, and host cells (e.g., mammalian host cells such as CHO, NS0 cells, and 293T cells) comprising the expression vectors. The present disclosure also provides methods of making the present prodrugs, comprising culturing the host cells under conditions that allow expression of prodrugs and isolating (also purifying) the prodrugs.

Figure 3:
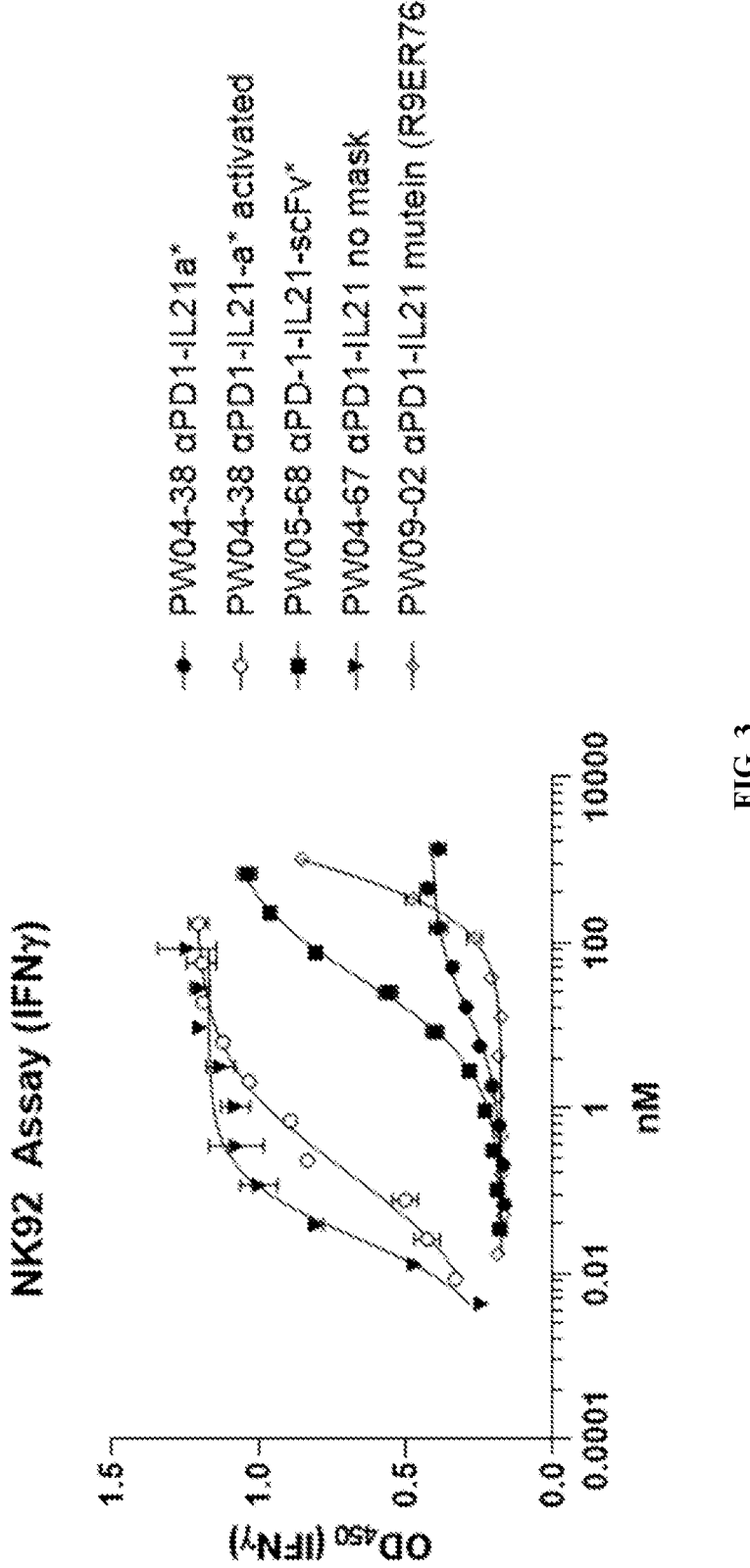
Figure 4A:
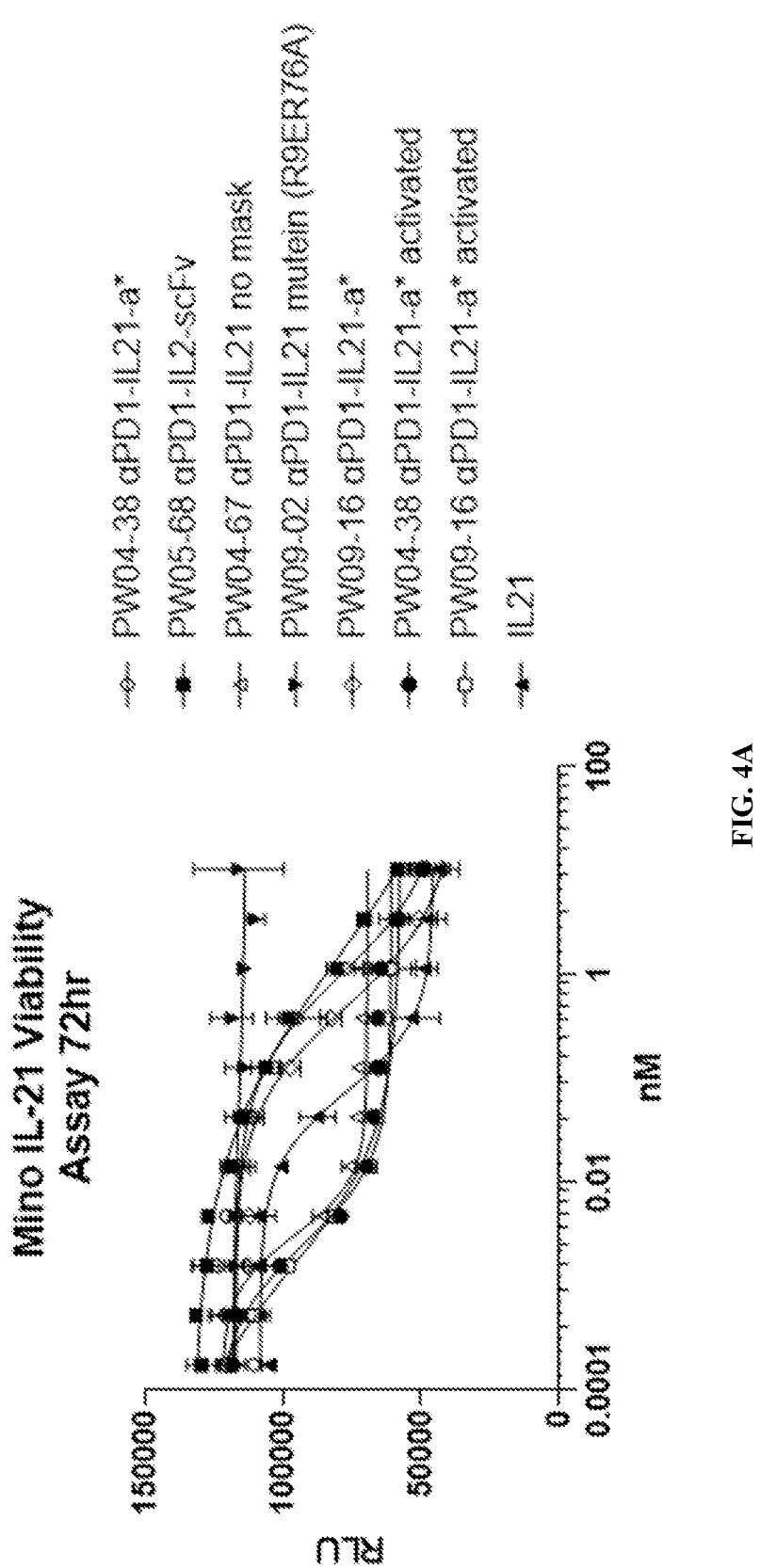
Figure 4B:
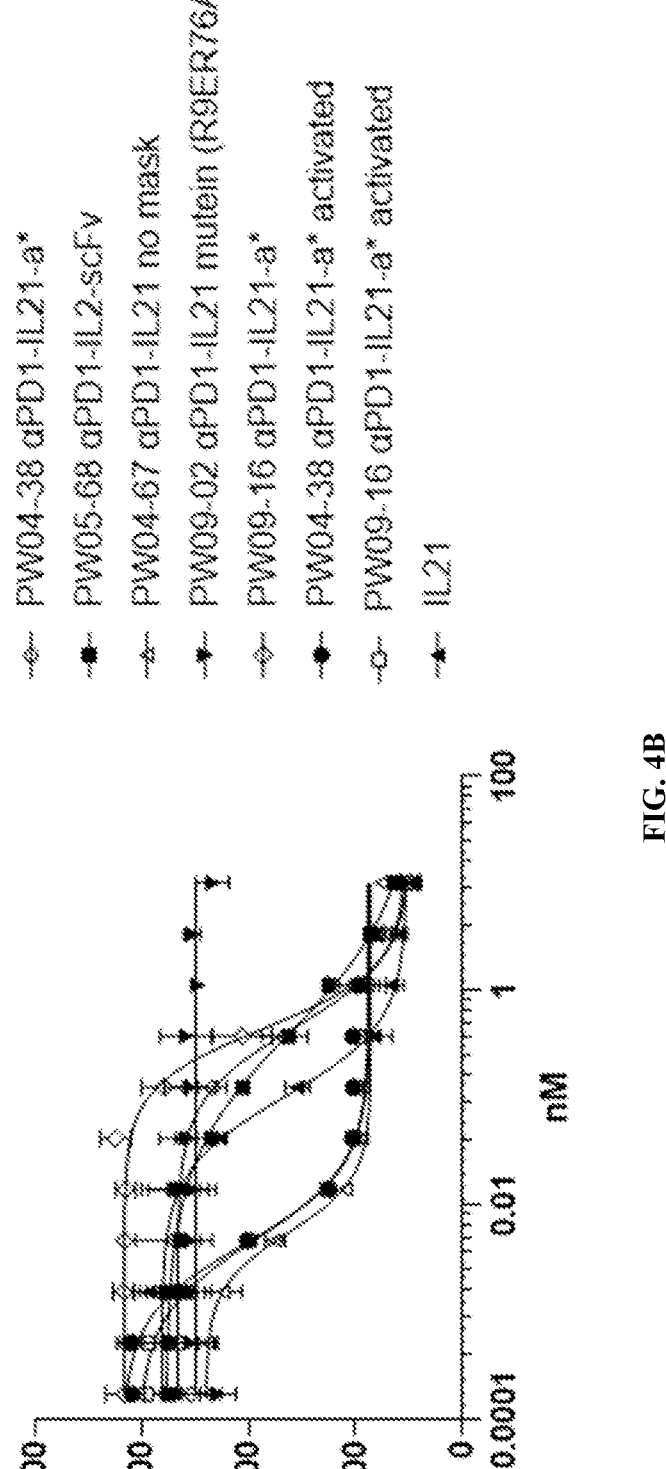
Figure 5A:
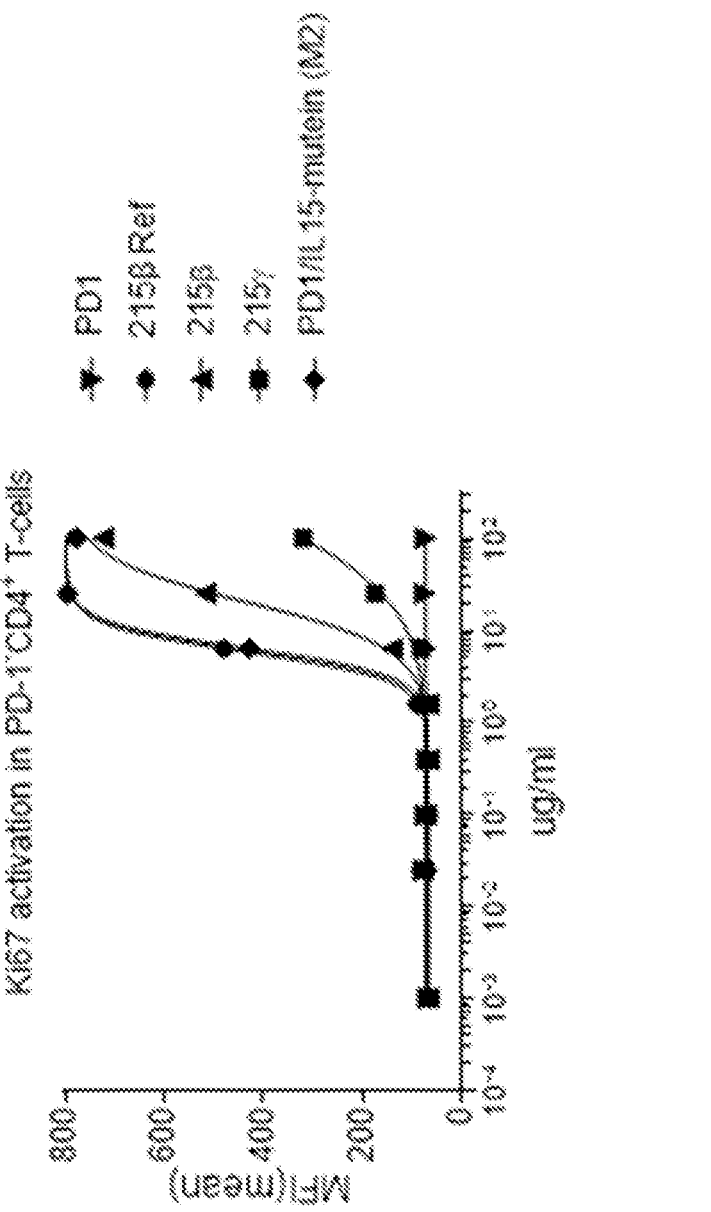
Figure 5B:
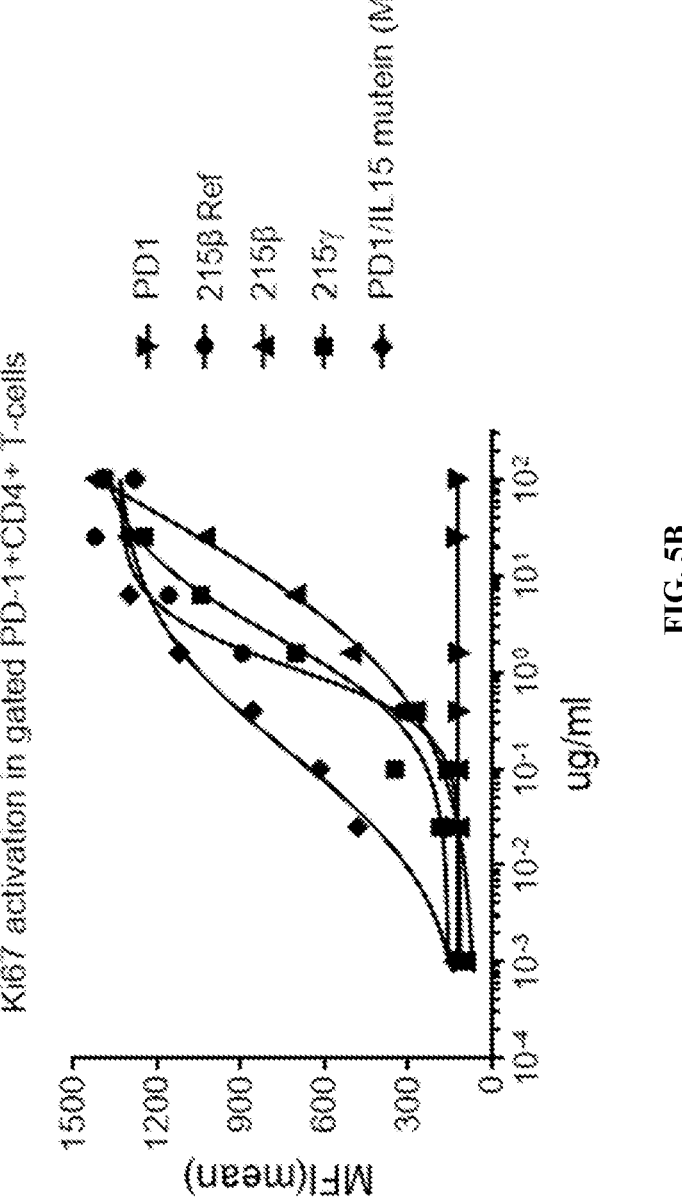

An Fc-based IL-21 prodrug molecule was not able to bind to cells such as Mino cells which expresses IL-21 receptors (FIG. 2), confirming that the cytokine moieties were masked. It was further shown that the masked molecules with PD-1 antibody as the carrier had minimum activities with the NK92 cells which do not express PD-1 (FIG. 3). It was a surprise to the inventors that the PD-1 antibody-based IL-21 prodrug molecules had meaningful activities with the Mino cells prior to activation (FIGS. 4A and 4B). Similar observations were made with an IL-2 prodrug (FIGS. 6A and 6B) and an IL-15 prodrug (FIGS. 5A-C). While not wishing to be bound by any theory, it is hypothesized that cis-binding of the PD-1 antibody to the antigen and the cytokine moiety to the cytokine receptors respectively, wherein both the antigen and the cytokine receptors are expressed on the same cell, led to the undoing of the masking effect of the masking moiety. It is therefore proposed that the prodrugs with the targeting moiety provides a significant selectivity to the cells expressing the antigens targeted by the carried moiety over the ones without the antigens. Surprisingly, it is feasible to construct prodrugs without the need of protease cleavage or removal of the masking moiety.

The present disclosure provides prodrugs which can be selectively activated at a disease site without the need of protease cleavage or removal of the masking moiety. In one aspect, the present disclosure provides novel cytokines prodrug comprising a cytokine moiety (a cytokine agonist polypeptide), a masking moiety, and a carrier moiety, wherein the masking moiety binds to the cytokine agonist polypeptide and inhibits an intended biological activity of the cytokine; the carrier moiety comprises an antigen binding moiety; the masking moiety is linked directly or indirectly to the carrier moiety through a non-cleavable peptide linker or without a peptide linker; and wherein the activity of the prodrug is higher in stimulating a cell which expresses both the antigen targeted by the carrier moiety and the receptor(s) of the cytokine than its activity in stimulating a cell which expresses the receptor(s) of the cytokine but not the antigen targeted by the carrier moiety.

In one aspect, the present disclosure provides novel cytokines prodrug comprising a cytokine moiety (a cytokine agonist polypeptide), a masking moiety, and a carrier moiety, wherein the masking moiety binds to the cytokine agonist polypeptide and inhibits an intended biological activity of the cytokine; the carrier moiety comprises an antigen binding moiety; the masking moiety is linked directly or indirectly to the carrier moiety through a non-cleavable peptide linker or without a peptide linker; and wherein the prodrug is activated at a disease site where there are cells expressing both the antigen targeted by the carrier moiety and the receptor(s) of the cytokine, or a biological activity of the prodrug is increased by at least 2 folds, at least 5 folds, or at least 10 folds at a disease site where there are cells expressing both the antigen targeted by the carrier moiety and the receptor(s) of the cytokine.

In some embodiments, the prodrug does not contain any cleavable peptide linker.

In some embodiments, the carrier moiety comprises an antigen-binding moiety, wherein the antigen is expressed on an immune cell. In some embodiments, the carrier moiety comprises an antigen-binding moiety, wherein the antigen is selected from PD-1, PD-L1, CTLA-4, TIGIT, TIM-3, LAG-3, CD25, CD16a, and CD16b.

In some embodiments, the cytokine moiety comprises a cytokine selected from an IL-2 agonist polypeptide, an IL-7 agonist polypeptide, an IL-9 agonist polypeptide, an IL-15 agonist polypeptide, and an IL-21 agonist polypeptide. In some embodiments, the cytokine is selected from an IL-1α agonist polypeptide, an IL-10 agonist polypeptide, an IL-4 agonist polypeptide, an IL-5 agonist polypeptide, an IL-β agonist polypeptide, an IL-8 agonist polypeptide, an IL-10 agonist polypeptide, an IL-12 agonist polypeptide, an IL-15 agonist polypeptide, an IL-17 agonist polypeptide, an IL-18 agonist polypeptide, an IL-22 agonist polypeptide, an IL-23 agonist polypeptide, an IL-31 agonist polypeptide, an IL-33 agonist polypeptide, an IL-36 agonist polypeptide, an Interferon-alpha agonist polypeptide, interferon gamma, 4-1BB ligand, OX-40 ligand, CD-40 ligand.

In some embodiments, the masking moiety is an extracellular domain (ECD) of a receptor of the cytokine. In some embodiments, the masking moiety comprises an antibody against the cytokine or a binding fragment of the antibody.

In some embodiments, the cytokine is an IL-21 agonist polypeptide; and wherein the masking moiety is the extracellular domain of IL-21 receptor α(IL-21Rα ECD) or a functional analog thereof. In some embodiments, the cytokine is an IL-2 agonist polypeptide or an IL-15 agonist polypeptide; and wherein the masking moiety is the extracellular domain of IL-2 receptor (IL-2Rβ ECD). In some embodiments, the cytokine is an IL-21 agonist polypeptide; and wherein the masking moiety is a Fab, a single chain Fv (scFv) or a single domain antibody against IL-21.

In some embodiments, the cytokine is an IL-2 agonist polypeptide; and wherein the masking moiety is a Fab, a single chain Fv (scFv), or a single domain antibody against IL-2.

In some embodiments, the cytokine is an IL-15 agonist polypeptide; and wherein the masking moiety is a Fab, a single chain Fv (scFv), or a single domain antibody against IL-15. In some embodiments, the cytokine moiety comprises an IL-15 agonist polypeptide, wherein the chimeric molecule further comprises the sushi domain of IL-15 receptor α(IL-15Rα sushi domain).

In some embodiments, the IL-21 agonist polypeptide comprises an amino acid sequence as SEQ ID NO: 1, or at least 90% identical as that of SEQ ID NO: 1. In some embodiments, the masking moiety is IL-21Rα-ECD or a functional analog thereof, which comprises an amino acid sequence selected from SEQ ID NO: 12, 63-72, and 73, or at least 90% identical as that of SEQ ID NO: 12. In some embodiments, the masking moiety is an scFv which binds to human IL-21; and wherein the scFv comprises an amino acid sequence of SEQ ID NO: 20 or 21.

In some embodiments, the IL-2 agonist polypeptide comprises an amino acid sequence of SEQ ID NO: 6, or 61, or at least 95% identical as that of SEQ ID NO: 6, or 61. In some embodiments, the masking moiety comprises the IL-2Rβ-ECD or a functional analog thereof; wherein the IL-2-Rβ-ECD comprises an amino acid sequence of SEQ ID NO: 11 or at least 95% identical as that of SEQ ID NO: 11. In some embodiments, the masking moiety is an scFv which binds to IL-2, wherein the scFv interferes with the interaction between IL-2 and IL-2Rα. In some embodiments, the masking moiety is an scFv which binds to IL-2, wherein the scFv interferes with the interaction between IL-2 and IL-2Rβ. In some embodiments, the masking moiety is scFv which binds to IL-2, wherein the scFv interferes with the interaction between IL-2 and IL-2Rγ. In some embodiments, the masking moiety is scFv which binds to IL-2, wherein the scFv comprises the same heavy chain and light chain CDRs as that of hybridoma 4E12B2D10. In some embodiments, the masking moiety is an scFv which binds to IL-2, wherein the scFv comprises an amino acid sequence of SEQ ID NO: 22, 23, or at least 95% identical as that of SEQ ID NO: 22, 23.

In some embodiments, the IL-15 agonist polypeptide comprises an amino acid sequence of SEQ ID NO: 7, or at least 95% identical as that of SEQ ID NO: 7. In some embodiments, the IL-15 prodrug further comprises a sushi domain, which comprises an amino acid sequence of SEQ ID NO: 8, or at least 95% identical as that of SEQ ID NO: 8. In some embodiments, the masking moiety comprises the IL-2Rβ-ECD or a functional analog thereof; wherein the IL-2-Rβ-ECD comprises an amino acid sequence of SEQ ID NO: 11 or at least 95% identical as that of SEQ ID NO: 11. In some embodiments, the masking moiety is an scFv which binds to IL-15, wherein the scFv interferes with the interaction between IL-15 and IL-2Rβ. In some the embodiments, the masking moiety is an scFv which binds to IL-15, wherein the scFv interferes with the interaction between IL-15 and IL-2Rγ. In some embodiments, the masking moiety is scFv which binds to IL-15, wherein the scFv comprises the same heavy chain and light chain CDRs as that of the IL-15 antibody 146B7, 146H5, or 404E4. In some embodiments, the masking moiety is scFv which binds to IL-15, wherein the scFv comprises an amino acid sequence of SEQ ID NO: 18 or 19.

In some embodiments, the human IL-21 agonist polypeptide comprises one or more mutations at position(s) selected from D18, Q19, E109, and K117 (numbering according to SEQ ID NO: 1). In particular embodiments, the human IL-21 agonist polypeptide comprises an amino acid sequence selected from SEQ ID NOs: 1, 2, 3, 4, and 5.

In some embodiments of the present prodrugs, the cytokine moieties and the masking moieties are fused to the carrier moieties through a noncleavable peptide linker, such as one selected from SEQ ID NOs: 27-34.

In some embodiments of the present prodrugs, the carrier moiety is an IgG1 antibody that comprises mutations L234A and L235A ("LALA") (EU numbering) or an IgG4 antibody that comprises mutations S228P/L234A/L235A (PAA). Other mutations which lead to the reduced Fc functionality, such as the ones described by Tam et al., Antibodies (2017) 6(12):1-34, can also be introduced when the Fc domain or the Fc of an antibody is used as the carrier moiety.

In particular embodiments, the carrier moiety is an antibody comprising knobs-into-holes mutations, wherein the cytokine moieties and the masking moieties are fused to the different heavy chains of the antibody. In certain embodiments, the knobs-into-holes mutations comprise a T366Y "knob" mutation on a polypeptide chain of the Fc domain or a heavy chain of the antibody, and a Y407T "hole" mutation in the other polypeptide of the Fc domain or the other heavy chain of the antibody (EU numbering). In certain embodiments, the knobs-into-holes mutations comprise Y349C and/or T366W mutations in the CH3 domain of the "knob chain" and E356C, T366S, L368A, and/or Y407V mutations in the CH3 domain of the "hole chain" (EU numbering).

In some embodiments, the carrier moiety is an antibody or an antigen-binding fragment thereof that specifically binds to one or more antigens selected from guanyl cyclase C (GCC), carbohydrate antigen 19-9 (CA19-9), glycoprotein A33 (gpA33), mucin 1 (MUC1), carcinoembryonic antigen (CEA), insulin-like growth factor 1 receptor (IGF1-R), human epidermal growth factor receptor 2 (HER2), human epidermal growth factor receptor 3 (HER3), delta-like protein 3 (DLL3), delta-like protein 4 (DLL4), epidermal growth factor receptor (EGFR), glypican-3 (GPC3), c-MET, vascular endothelial growth factor receptor 1 (VEGFR1), vascular endothelial growth factor receptor 2 (VEGFR2), Nectin-4, Liv-1, glycoprotein NMB (GPNMB), prostate specific membrane antigen (PSMA), Trop-2, carbonic anhydrase IX (CA9), endothelin B receptor (ETBR), six transmembrane epithelial antigen of the prostate 1 (STEAP1), folate receptor alpha (FR-α), SLIT and NTRK-like protein 6 (SLITRK6), carbonic anhydrase VI (CA6), ectonucleotide pyrophosphatase/phosphodiesterase family member 3 (ENPP3), mesothelin, trophoblast glycoprotein (TPBG), CD19, CD20, CD22, CD33, CD40, CD56, CD66e, CD70, CD74, CD79b, CD98, CD123, CD138, CD352, CD47, signal-regulatory protein alpha (SIRPα), PD1, Claudin 18.2, Claudin 6, 5T4, BCMA, PD-L1, PD-1, fibroblast activation protein alpha (FAPalpha), the melanoma-associated chondroitin sulfate proteoglycan (MCSP), and epithelial cellular adhesion molecule (EPCAM). In specific embodiments, the carrier moiety is an antibody or fragment thereof which binds to FAPalpha or 5T4.

In another aspect, the present disclosure provides polynucleotides encoding the present prodrugs or fusion molecules, expression vectors comprising the polynucleotides, and host cells (e.g., mammalian host cells such as CHO, NS0 cells, and 293T cells) comprising the expression vectors. The present disclosure also provides methods for making the present prodrugs or fusion molecules, comprising culturing the mammalian host cells under conditions that allow expression of the prodrugs or fusion molecules and isolating the prodrugs or fusion molecules.

The present disclosure also provides a method of treating a cancer or an infectious disease or stimulating the immune system in a patient (e.g., human patient) in need thereof, comprising administering to the patient a therapeutically effective amount of the cytokine prodrug, or the pharmaceutical composition of the present disclosure. The patient may have, for example, a viral infection (e.g., HIV, HBV, HCV, or HPV infection), or a cancer selected from the group consisting of breast cancer, lung cancer, pancreatic cancer, esophageal cancer, medullary thyroid cancer, ovarian cancer, uterine cancer, prostate cancer, testicular cancer, colorectal cancer, and stomach cancer. Also provided herein are cytokine prodrugs for use in treating a cancer or an infectious disease or stimulating the immune system in the present method; use of a cytokine prodrug for the manufacture of a medicament for treating a cancer or an infectious disease or stimulating the immune system in the present method; and articles of manufacture (e.g., kits) comprising one or more dosing units of the present cytokine prodrug.

Also provided herein are prodrugs for use in treating a cancer or an infectious disease or stimulating the immune system in the present method; use of a prodrug for the manufacture of a medicament for treating a cancer or an infectious disease or stimulating the immune system in the present method; and articles of manufacture (e.g., kits) comprising one or more dosing units of the present prodrugs.

Other features, objectives, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

BRIEF DESCRIPTIONS OF THE DRAWINGS

Figure 1A:
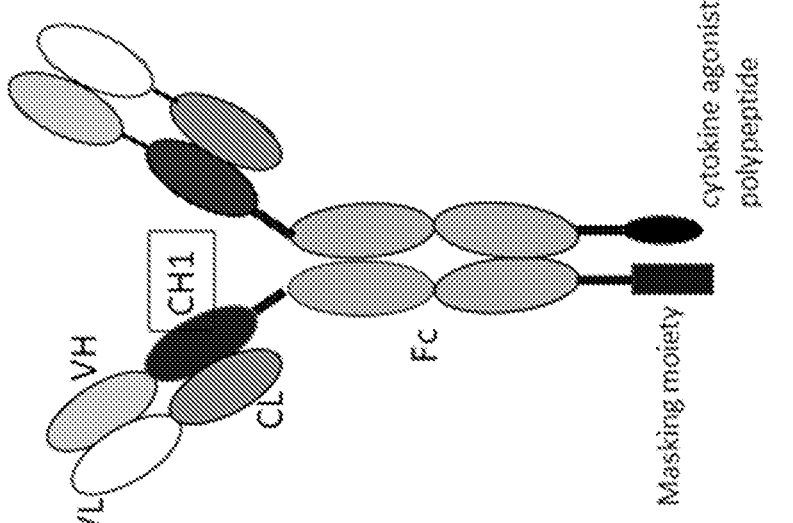
Figures 1C, 1D:
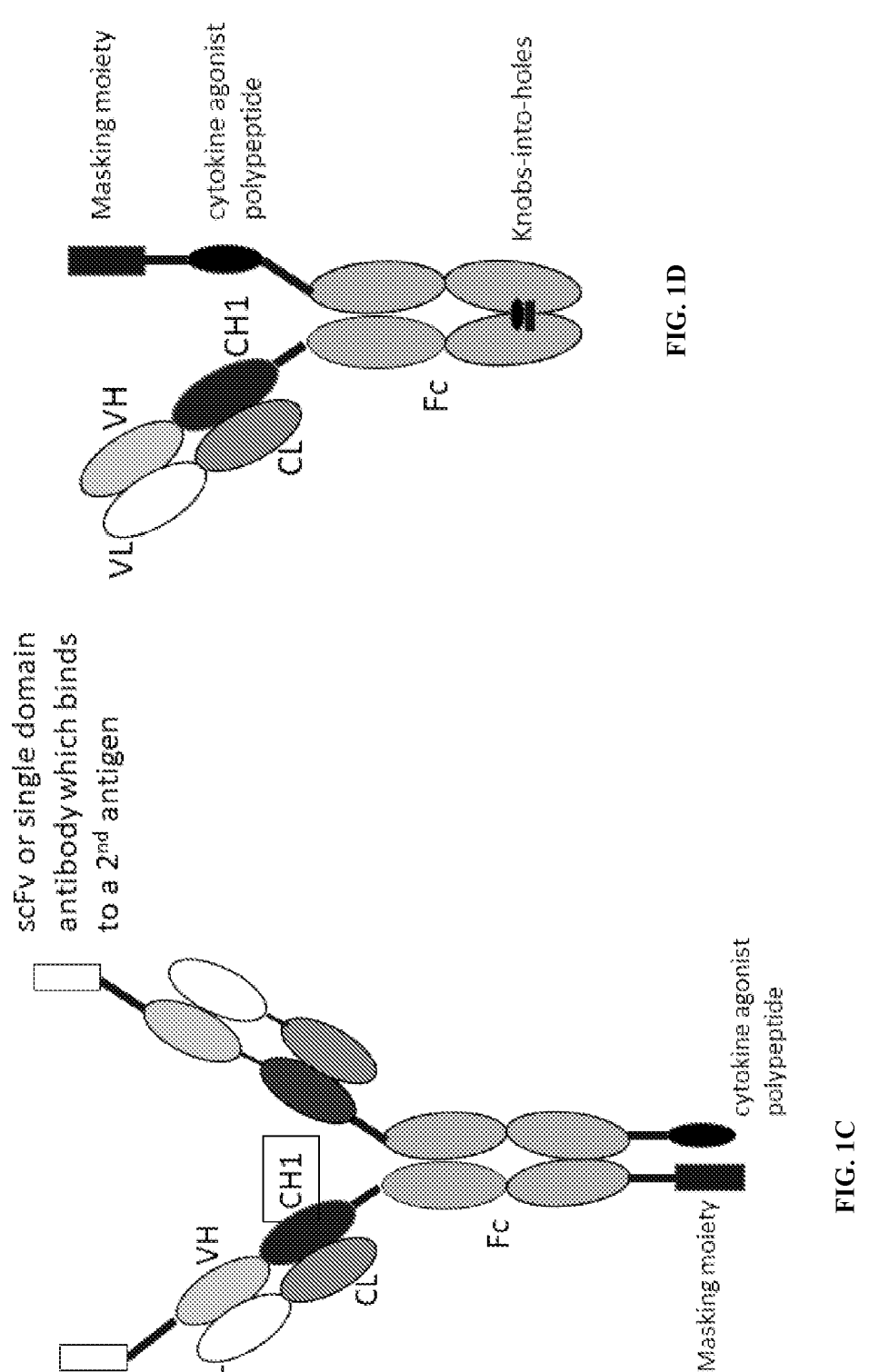
Figure 1E:
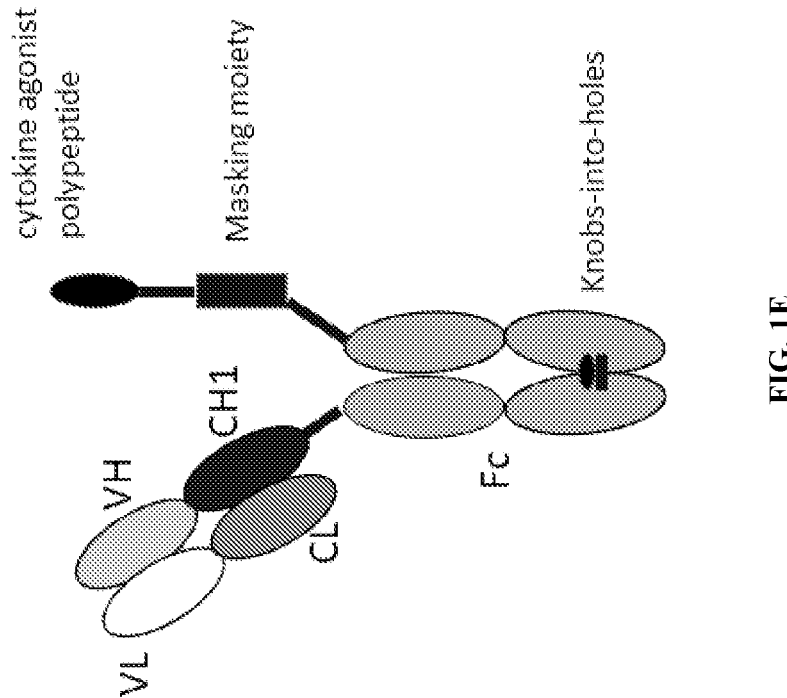

FIGS. 1A-E illustrate a heterodimeric cytokine prodrug wherein the carrier is an antibody. FIG. 1A illustrates a prodrug wherein the carrier is a typical antibody with two light chains and two heavy chains. FIG. 1B illustrates a prodrug with a bispecific antibody as the carrier, wherein each antigen-binding moiety is monomeric with one antigen-binding moiety comprising a Fab domain and the second antigen-binding moiety comprising an scFv or a single domain antibody. FIG. 1C illustrates a prodrug with a bispecific antibody as the carrier, wherein each antigen-binding moiety is dimeric. FIG. 1D illustrates a prodrug with a dimeric Fc domain fused to a Fab domain on one of its polypeptide chains and to a cytokine peptide on the other polypeptide chain. The cytokine is fused via its N-terminus to a masking moiety. FIG. 1E illustrates a prodrug with a dimeric Fc domain fused to a Fab domain on one of its polypeptide chains and to a cytokine peptide on the other polypeptide chain. The masking moiety is fused via its N-terminus to a cytokine peptide.

Figure 2:
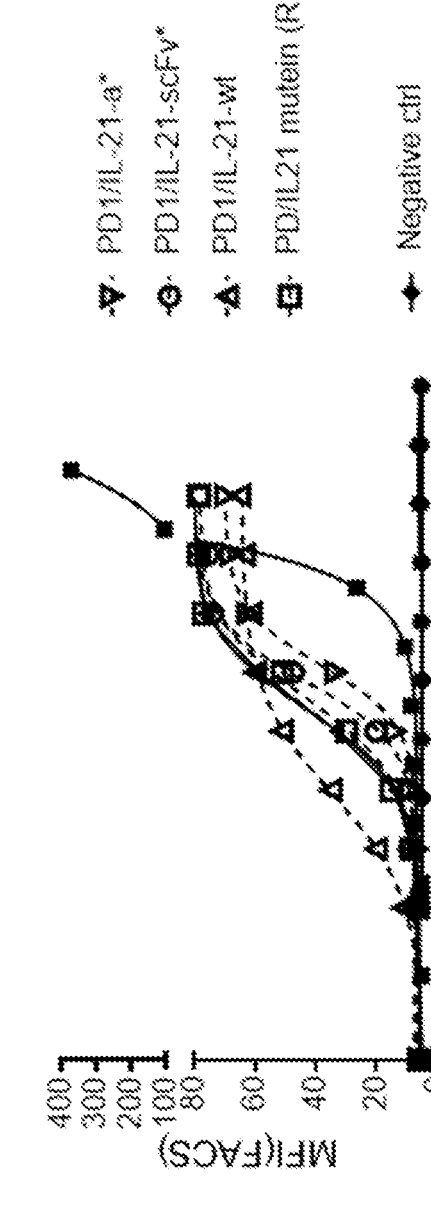

FIG. 2 shows the binding of PD-1 antibody and Fc-IL-21 fusion molecules and control molecules to Mino cells. The binding was analyzed by FACS.

FIG. 3 shows the results of a NK-92 cell-based biological activity assay of IL-21 prodrugs prior to and after activation by protease MMP2 and the control molecules. PW04-38 αPD1-IL21-a* and PW09-16 αPD1-IL21-a* are two batches of the same molecule, which is an anti-PD-1 antibody-based IL-21 with IL-21R α-ECD as the masking moiety; PW05-68 αPD1-IL21-scFv is a PD-1 antibody-based IL-21 prodrug with the scFv as the masking moiety. A first control molecule PW04-67 αPD1-IL21no mask is an anti-PD-1 antibody-IL-21 fusion molecule without a mask and having a wild-type IL-21. Another control molecule, PW09-02 αPD1-IL21muteinR9ER76A is an anti-PD-1 antibody-IL-21 fusion molecule without a mask and with an IL-21 mutein with R9E and R76A amino acid substitutions (numbering according to SEQ ID NO: 1). PW04-38 αPD1-IL21-a* activated and PW09-16 αPD1-IL21-a* activated are both the anti-PD-1 antibody-IL-21 wild type fusion molecule whose mask has been cleaved with a protease.

FIGS. 4A and 4B show the results of the Mino cell-based biological activity assay of PD-1-IL-21 prodrugs prior to and after activation by protease MMP2 and the control molecules. FIG. 4A shows the results after 72 hours of incubation of the cytokine fusion molecules with the Mino cells prior to the analysis. FIG. 4B shows the results after 120 hours of incubation prior to the analysis.

FIGS. 5A, 5B, and 5C show the results of Ki67 activation of the CD4+ T cells in PBMC after treated with an anti-PD-1 antibody (PD-1), an Fc-IL-15 fusion molecule masked with an scFv (215β), anti-PD1-antibody-IL-15 fusion molecule masked with an scFv (215γ), an Fc-IL-15 fusion molecule with no mask (215β ref), and an PD1-antibody-IL-15 fusion molecule with no mask (PD1/IL15 mutein (M2)). FIG. 5A shows the results of Ki67 activation of CD4+ T cells without PD-1 expression. FIG. 5B shows the results of Ki67 activation of CD4+ T cells with PD-1 expression. FIG. 5C shows the EC50 values of the testing articles with CD4+ T cells without and with PD-1 expression. It also shows the fold of changes of the EC50 values between the CD4+ T cells without and with PD-1 expression.

Figure 6A:
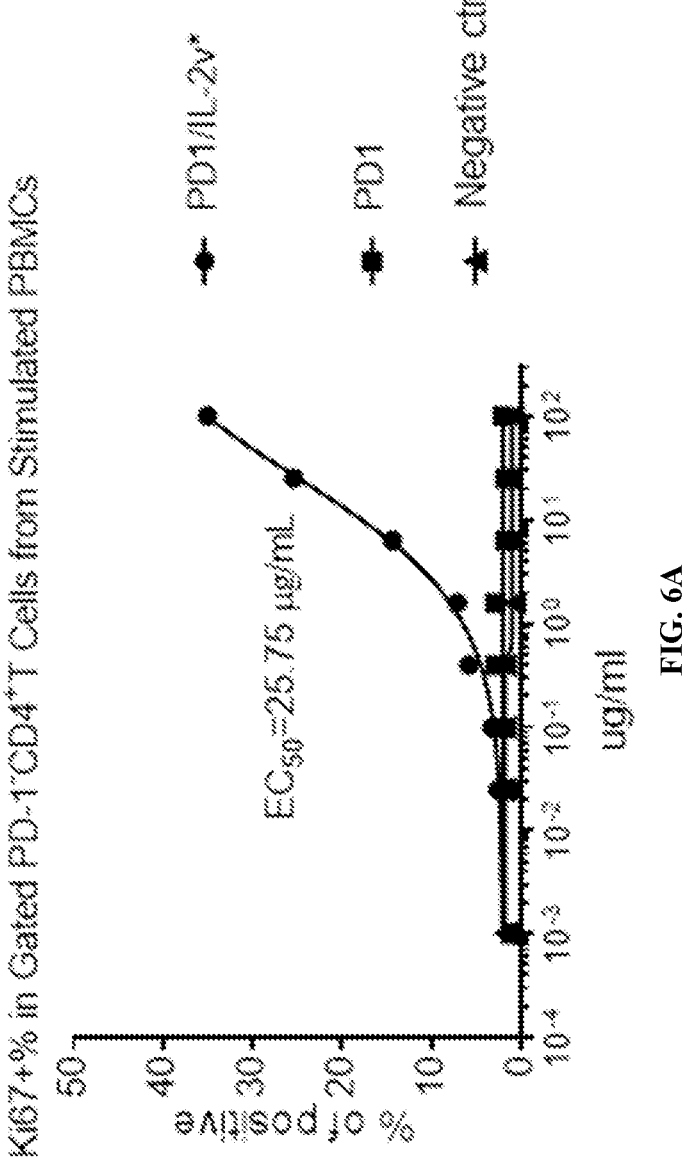
Figure 6B:
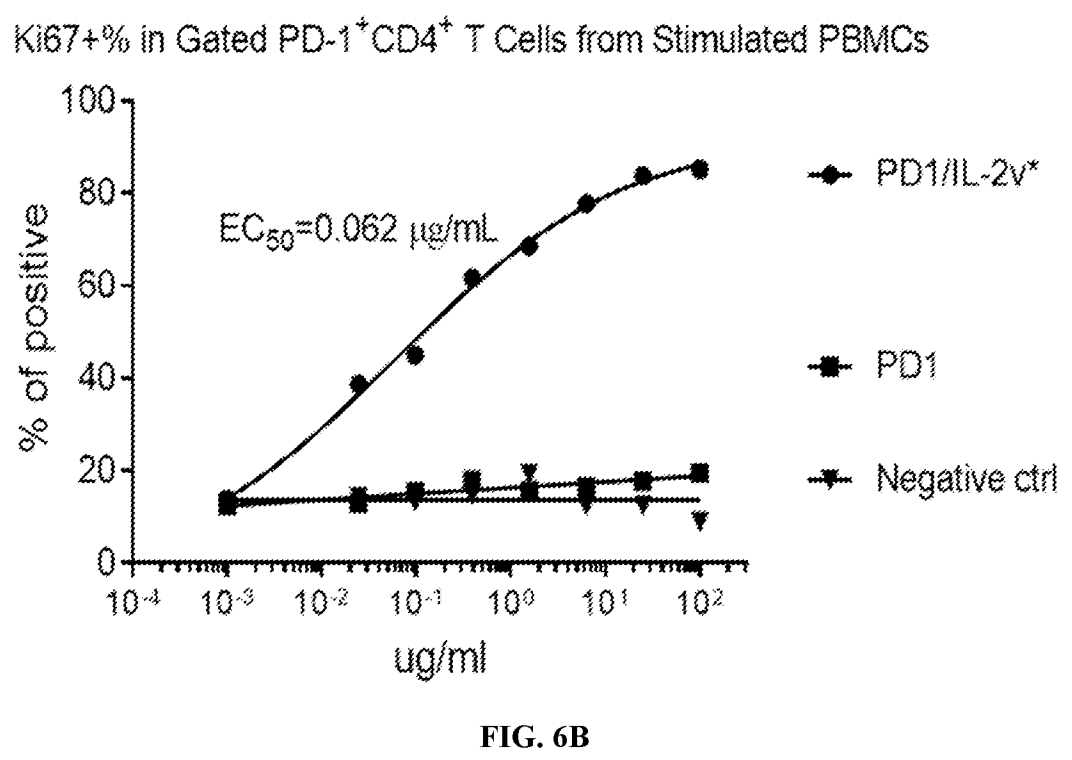

FIGS. 6A and 6B show the results of Ki67 activation of the CD4+ T cells in PBMC after treatment with an anti-PD-1 antibody (PD-1), a negative control (an IgG1 antibody), and an anti-PD1-antibody-IL-2 mutein fusion masked with IL-2 receptor β extracellular domain (IL-2β-ECD) (PD-1/IL2V*). FIG. 6A shows the results of Ki67 activation of CD4+ T cells without PD-1 expression. FIG. 6B shows the results of Ki67 activation of CD4+ T cells with PD-1 expression.

Figure 7:
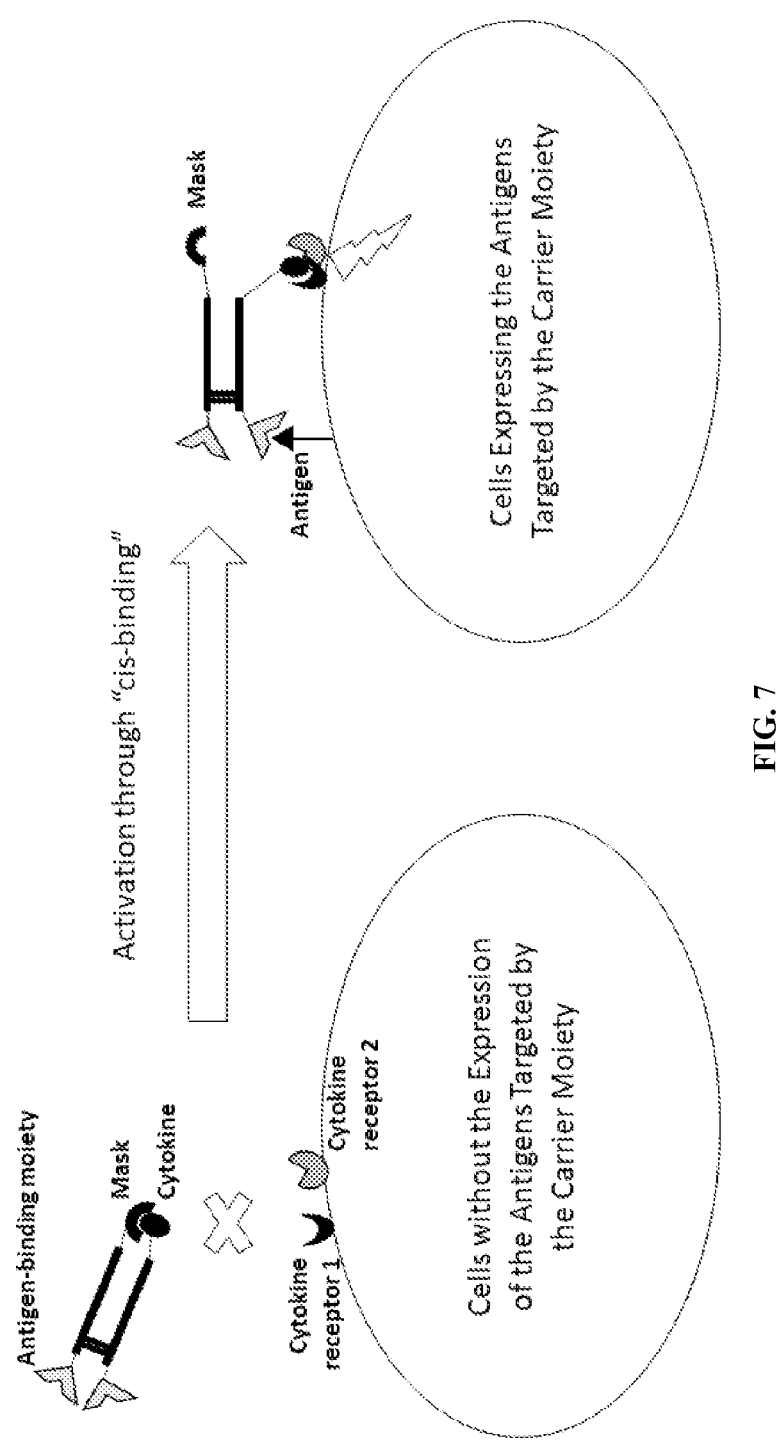

FIG. 7 illustrates a novel mechanism of prodrug activation through "cis-binding." The target cells (right) express both the antigen targeted by the carrier moiety and the receptor for the cytokine moiety. Binding of the prodrug to the antigen on the cell surface brings the prodrug to the proximity of the cytokine receptor on the cell, allowing the cytokine receptor to compete effectively with and displace the masking moiety, leading to cellular signaling by the bound cytokine receptor. No protease cleavage of the masking moiety is necessary to remove the mask and activate the prodrug. On cells expressing the cytokine receptor but not the antigen (left), the cytokine moiety of the prodrug remains masked and inactive.

DETAILED DESCRIPTION OF THE INVENTION

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X." Additionally, use of "about" preceding any series of numbers includes "about" each of the recited numbers in that series. For example, description referring to "about X, Y, or Z" is intended to describe "about X, about Y, or about Z."

The term "antigen-binding moiety" refers to a polypeptide or a set of interacting polypeptides that specifically bind to an antigen, and includes, but is not limited to, an antibody (e.g., a monoclonal antibody, a polyclonal antibody, a multi-specific antibody, a dual-specific or bispecific antibody, an anti-idiotypic antibody, or a bifunctional hybrid antibody) or an antigen-binding fragment thereof (e.g., a Fab, a Fab', a F(ab')$_2$, a Fv, a disulfide linked Fv, an scFv, a single domain antibody (dAb), or a diabody, a single chain antibody, and an Fc-containing polypeptide such as an immunoadhesin). In some embodiments, the antibody may be of any heavy chain isotype (e.g., IgG, IgA, IgM, IgE, or IgD) or subtype (e.g., IgG$_1$, IgG$_2$, IgG$_3$, or IgG$_4$). In some embodiments, the antibody may be of any light chain isotype (e.g., kappa or lambda). The antibody may be human, non-human (e.g., from mouse, rat, rabbit, goat, or another non-human animal), chimeric (e.g., with a non-human variable region and a human constant region), or humanized (e.g., with non-human CDRs and human framework and constant regions). In some embodiments, the antibody is a derivatized antibody.

As used herein, the phrase "against," "binding to," or "specifically binding to" in the context of the interaction between two molecules is intended to mean that the binding has a $K_D$ not more than 1000 nM (e.g., not more than 100, 10, or 1 nM; such as less than 1 nM, 1-10 nM, 10-100 nM, or 100-1000 nM) as measured by common methods in the art (e.g., surface plasmon resonance, ELISA, and the like).

The term "cytokine agonist polypeptide" refers to a wildtype cytokine, or an analog thereof. An analog of a wildtype cytokine has the same biological specificity (e.g., binding to the same receptor(s) and activating the same target cells) as the wildtype cytokine, although the activity level of the analog may be different from that of the wildtype cytokine. The analog may be, for example, a mutein (i.e., mutated polypeptide) of the wildtype cytokine, and may comprise at least one, at least two, at least three, at least four, at least five, at least six, at least seven, at least eight, at least nine, or at least ten mutations relative to the wildtype cytokine.

The term "cytokine antagonist," "masking moiety," or "cytokine mask" refers to a moiety (e.g., a polypeptide) that binds to a cytokine and thereby inhibits the cytokine from binding to its receptor on the surface of a target cell and/or exerting its biological functions while being bound by the antagonist or mask. Examples of a cytokine antagonist or mask include, without limitations, a polypeptide derived from an extracellular domain of the cytokine's natural receptor that makes contact with the cytokine.

The term "effective amount" or "therapeutically effective amount" refers to an amount of a compound or composition sufficient to treat a specified disorder, condition, or disease (e.g., ameliorate, palliate, lessen, and/or delay one or more of its symptoms). In reference to a disease such as cancer, an effective amount may be an amount sufficient to delay cancer development or progression (e.g., decrease tumor growth rate, and/or delay or prevent tumor angiogenesis, metastasis, or infiltration of cancer cells into peripheral organs), reduce the number of epithelioid cells, cause cancer regression (e.g., shrink or eradicate a tumor), and/or prevent or delay cancer occurrence or recurrence. An effective amount can be administered in one or more doses.

The term "functional analog" refers to a molecule that has the same biological specificity (e.g., binding to the same ligand) and/or activity (e.g., activating or inhibiting a target cell) as a reference molecule.

The term "fused" or "fusion" in reference to two polypeptide sequences refers to the joining of the two polypeptide sequences through a backbone peptide bond. Two polypeptides may be fused directly or through a peptide linker that is one or more amino acids long. A fusion polypeptide may be made by recombinant technology from a coding sequence containing the respective coding sequences for the two fusion partners, with or without a coding sequence for a peptide linker in between. In some embodiments, fusion encompasses chemical conjugation.

The term "pharmaceutically acceptable excipient" when used to refer to an ingredient in a composition means that the excipient is suitable for administration to a treatment subject, including a human subject, without undue deleterious side effects to the subject and without affecting the biological activity of the active pharmaceutical ingredient (API).

The term "prodrug" refers to a therapeutic molecule that is inactive or has low activity in vitro or in the circulation while its activity is increased at the site of a disease.

The term "subject" refers to a mammal and includes, but is not limited to, a human, a pet (e.g., a canine or a feline), a farm animal (e.g., cattle or horse), a rodent, or a primate.

As used herein, "treatment" or "treating" is an approach for obtaining beneficial or desired clinical results. Beneficial or desired clinical results include, but are not limited to, one or more of the following: alleviating one or more symptoms resulting from a disease, diminishing the extent of a disease, ameliorating a disease state, stabilizing a disease (e.g., preventing or delaying the worsening or progression of the disease), preventing or delaying the spread (e.g., metastasis) of a disease, preventing or delaying the recurrence of a disease, providing partial or total remission of a disease, decreasing the dose of one or more other medications required to treat a disease, increasing the patient's quality of life, and/or prolonging survival. The methods of the present disclosure contemplate any one or more of these aspects of treatment.

It is to be understood that one, some, or all the properties of the various embodiments described herein may be combined to form other embodiments of the present invention. The section headings used herein are for organizational purposes only and are not to be construed as limiting the subject matter described thereunder.

I. Cytokine Prodrugs

The present disclosure provides cytokine prodrugs that become more active at the site of a disease. The prodrugs comprise a cytokine agonist polypeptide (cytokine moiety) a carrier moiety, and a masking moiety. The cytokine moiety is linked, with or without a peptide linker (e.g., a noncleavable peptide linker), to the carrier moiety and is masked (bound) by the masking moiety. The masking moiety may be linked to the cytokine moiety or to the carrier moiety with or without a peptide linker (e.g., a noncleavable peptide linker). Alternatively, the cytokine moiety is linked, with or without a peptide linker (e.g., a noncleavable peptide linker), to the masking moiety, which in turn is linked, with or without a peptide linker (e.g., a noncleavable peptide linker), to the carrier moiety.

The carrier moiety comprises an antigen-binding domain that binds to an antigen on a target cell (e.g., a tumor cell or an immune cell). In some embodiments, the carrier comprises an antibody. See, e.g., FIG. 1A. In some embodiments, the carrier moiety comprises a bispecific antibody, which binds to two different antigens, as illustrated on FIGS. 1B and 1C.

The masking moiety may comprise, for example, an extracellular domain (ECD) of a cytokine receptor, where the ECD is linked to the cytokine moiety (see, e.g., FIGS. 1D and 1E) and/or to the carrier moiety through a non-cleavable linker (see, e.g., FIGS. 1A-C and 1E). The mask binds to and inhibits the cytokine moiety's biological functions. These prodrugs can engage the target cell via "cis-binding" of a cytokine receptor and an antigen expressed on the cell surface, leading to increased activity of the prodrug without cleavage and removal of the masking moiety. The cytokine moiety of the prodrugs may increase in activity at a target site (e.g., at a tumor site or the surrounding environment), where both the antigen targeted by the carrier and a receptor of the cytokine are expressed on the same cell. Examples of such prodrugs are illustrated in FIGS. 1A-E and the "cis-binding" mechanism of action is illustrated in FIG. 7.

A. Cytokine Moieties of the Prodrugs

In some embodiments, the cytokine moiety comprises an IL-2 agonist polypeptide. In some embodiments, the IL-2 agonist polypeptide is an IL-2 mutein having mutations R38S/F42A/Y45A/E62A or F42A/Y45A/L72G (numbering according to SEQ ID NO: 6). In some embodiments, the IL-2 mutein of the present disclosure may comprise a mutation at T3, D20, K35, R38, F42, F44, Y45, E62, E68, L72, A73, N88, N90, C125, and Q126 (numbering according to SEQ ID NO: 6). In certain embodiments, the novel IL-2 mutein comprises mutations at R38, F42, Y45, and A73 (numbering according to SEQ ID NO: 6).

In some embodiments, the cytokine moiety of the prodrug comprises an IL-15 agonist polypeptide. In some embodiments, the human IL-15 polypeptide comprises one or more mutations selected from N1A, N1D, N4A, N4D, I6T, S7A, D8A, D8T, D8E, D8N, K10A, K10D, K11A, K11D, E46, V49, L45, S51, L52, D61A, D61N, T62L, T62A, E64A, E64L, E64K, E64Q, N65A, N65L, N65D, L66D, L66E, I67D, I67E, I68S, I68E, L69S, L69E, N72A, N72D, V63E, V63D, L66E, L66D, I67E, I67D, Q108E, N112A, N1D/D61N, N1D/E64Q, N4D/D61N, N4D/E64Q, D8N/D61N, D8N/E64Q, D61N/E64Q, E64Q/Q108E, N1D/N4D/D8N, D61N/E64Q/N65D, N1D/D61N/E64Q, N1D/Q108E, N1D/D61N/E64Q/Q108E, N4D/D61N/E64Q/Q108E, and D30N/E64Q/N65D (numbering according SEQ ID NO: 7). In some embodiments, the IL-15 prodrug further comprises a sushi domain. In some embodiments, the sushi domain comprises an amino acid sequence of SEQ ID NO: 8 or at least 95% identical as that of SEQ ID NO: 8.

In some embodiments, the cytokine moiety comprises an IL-21 agonist polypeptide. In some embodiments, the IL-21 agonist polypeptide may be a wildtype IL-21 polypeptide such as a wildtype human IL-21 (e.g., SEQ ID NO: 1), or an IL-21 mutein derived from a human IL-21, e.g., one with an amino acid sequence selected from SEQ ID NOs: 2-5. The IL-21 mutein may have significantly reduced affinity for IL-21Rα or IL-21RαRβ, as compared to wild type IL-21. In some embodiments, the IL-21 mutein has a binding affinity for the high-affinity IL-2Rα that is 5 times, 10 times, 20 times, 50 times, 100 times, 300 times, 500 times, 1,000 times, or 10,000 times lower compared to wild type IL-21. Unless otherwise indicated, all residue numbers in IL-21 and IL-21 muteins described herein are in accordance with the numbering in SEQ ID NO: 1.

B. Masking Moieties of the Prodrugs

The masking moiety, in the present prodrug may comprise a peptide or an antibody or antibody fragment that binds to the cytokine moiety in the prodrug, masking the cytokine moiety and inhibiting its biological functions. In some embodiments, the masking moiety is operationally linked to the rest of the prodrug through a non-cleavable peptide linker.

By way of example, the prodrug comprises an IL-2 agonist polypeptide and the masking moiety comprises a peptide or antibody, or antigen-binding fragment thereof, that binds IL-2 and interferes with the binding of the IL-2 to its cognate receptors. In some embodiments, the masking moiety reduces biological activities of the IL-2 moiety while masked. In some embodiments, the IL-2 antagonist comprises an IL-2Rβ or IL-2Rγ extracellular domain or its functional analog, such as one derived from human IL-2Rβ or human IL-2Rγ (e.g., SEQ ID NO: 11 or 13). In some embodiments, the IL-2 masking moiety comprises a peptide identified through a peptide library screening. In some embodiments, the IL-2 masking moiety comprises an antibody or fragment thereof that blocks the binding of IL-2 or IL-2 muteins to an IL-2 receptor. In some embodiments, the masking moiety comprises an scFv of an antibody against IL-2. In some embodiments, the masking moiety comprises an amino acid sequence of SEQ ID NO: 22 or 23, or at least 95% identical as that of SEQ ID NO: 22 or 23.

By way of another example, the prodrug comprises an IL-21 agonist polypeptide and the masking moiety comprises a peptide or antibody, or antigen-binding fragment thereof, that binds IL-21 and interferes with the binding of the IL-21 to its cognate receptors. In some embodiments, the masking moiety reduces biological activities of the IL-21 moiety while masked. In some embodiments, the IL-21 antagonist comprises an IL-21Rα or IL-21Rγ extracellular domain or its functional analog, such as one derived from human IL-21Rα or human IL-21Rγ (e.g., SEQ ID NO: 12 or 13). In some embodiments, the IL-21 masking moiety comprises a peptide identified through a peptide library screening. In some embodiments, the IL-21 masking moiety comprises an antibody or fragment thereof that blocks the binding of IL-21 or IL-21 muteins to an IL-21 receptor. In some embodiments, the masking moiety comprises an scFv of an antibody against IL-21. In some embodiments, the masking moiety comprises an amino acid sequence of SEQ ID NO: 20 or 21, or at least 95% identical as that of SEQ ID NO: 20 or 21.

By way of another example, the prodrug comprises a masking moiety of any cytokine disclosed herein, including, but not limited to a cytokine selected from IL-7 agonist polypeptide, an IL-9 agonist polypeptide, an IL-15 agonist polypeptide, an IL-1a agonist polypeptide, an IL-1β agonist polypeptide, an IL-4 agonist polypeptide, an IL-5 agonist polypeptide, an IL-6 agonist polypeptide, an IL-8 agonist polypeptide, an IL-10 agonist polypeptide, an IL-12 agonist polypeptide, an IL-17 agonist polypeptide, an IL-18 agonist polypeptide, an IL-22 agonist polypeptide, an IL-23 agonist polypeptide, an IL-31 agonist polypeptide, an IL-33 agonist polypeptide, an IL-36 agonist polypeptide, an Interferon-alpha agonist polypeptide, an interferon gamma agonist polypeptide, a 4-1BB ligand, an OX-40 ligand, and a CD-40 ligand.

C. Carrier Moieties of the Prodrugs

The carrier moieties of the present prodrugs comprise an antigen-binding domain and optionally other domains. The carrier moiety improves the PK profiles such as serum half-life of the cytokine agonist polypeptide, and also targets the cytokine agonist polypeptide to a target site in the body, such as a tumor site.

1. Antigen-Binding Domains of Carrier Moieties

The carrier moiety comprises an antigen-binding domain and may be an antibody or an antigen-binding fragment thereof, or an immunoadhesin. In some embodiments, the antigen-binding carrier moiety is a full-length antibody with two heavy chains and two light chains, a Fab fragment, a Fab' fragment, a F(ab')₂ fragment, a Fv fragment, a disulfide linked Fv fragment, a single domain antibody, a nanobody, or a single-chain variable fragment (scFv). In some embodiments, the antigen-binding moiety is a bispecific antigen-binding moiety and can bind to two different antigens or two different epitopes on the same antigen. The antigen-binding moiety may provide additional and potentially synergetic therapeutic efficacy to the cytokine agonist polypeptide.

The cytokine agonist polypeptide and its mask may be fused to the N-terminus or C-terminus of the light chain(s) and/or heavy chain(s) of the antigen-binding moiety. By way of example, the IL-21 agonist polypeptide and its mask may be fused to the antibody heavy chain or an antigen-binding fragment thereof or to the antibody light chain or an antigen-binding fragment thereof. In some embodiments, one terminus of the IL-21 agonist polypeptide is fused to the C-terminus of one or both heavy chains of an antibody, and the IL-21 mask is fused to the other terminus of the IL-21 agonist polypeptide through a non-cleavable peptide linker. In some embodiments, the IL-21 agonist polypeptide is fused to the C-terminus of one of the heavy chains of an antibody, and the IL-21 mask is fused to the C-terminus of the other heavy chain of the antibody through a non-cleavable peptide linker, wherein the two heavy chains contain mutations that allow the specific pairing of the two different heavy chains.

Strategies for forming heterodimers are well known (see, e.g., Spies et al., Mol Imm. (2015) 67(2)(A):95-106). For example, the two heavy chain polypeptides in the prodrug may form stable heterodimers through "knobs-into-holes" mutations. "Knobs-into-holes" mutations are made to promote the formation of the heterodimers of the antibody heavy chains and are commonly used to make bispecific antibodies (see, e.g., U.S. Pat. No. 8,642,745). For example, the Fc domain of the antibody may comprise a T366W mutation in the CH3 domain of the "knob chain" and T366S, L368A, and/or Y407V mutations in the CH3 domain of the "hole chain." An additional interchain disulfide bridge between the CH3 domains can also be used, e.g., by introducing a Y349C mutation into the CH3 domain of the "knobs chain" and an E356C or S354C mutation into the CH3 domain of the "hole chain" (see, e.g., Merchant et al., Nature Biotech (1998) 16:677-81). In other embodiments, the antibody moiety may comprise Y349C and/or T366W mutations in one of the two CH3 domains, and E356C, T366S, L368A, and/or Y407V mutations in the other CH3 domain. In certain embodiments, the antibody moiety may comprise Y349C and/or T366W mutations in one of the two CH3 domains, and S354C (or E356C), T366S, L368A, and/or Y407V mutations in the other CH3 domain, with the additional Y349C mutation in one CH3 domain and the additional E356C or S354C mutation in the other CH3 domain, forming an interchain disulfide bridge (numbering always according to EU index of Kabat; Kabat et al., "Sequences of Proteins of Immunological Interest," 5th ed., Public Health Service, National Institutes of Health, Bethesda, Md. (1991)). Other knobs-into-holes technologies, such as those described in EP1870459A1, can be used alternatively or additionally. Thus, another example of knobs-into-holes mutations for an antibody moiety is having R409D/K370E mutations in the CH3 domain of the "knob chain" and D399K/E357K mutations in the CH3 domain of the "hole chain" (EU numbering).

In some embodiments, the antigen-binding moiety in the prodrug is an antibody that comprises L234A and L235A ("LALA") mutations in its Fc domain. The LALA mutations eliminate complement binding and fixation as well as Fcy dependent ADCC (see, e.g., Hezareh et al. J. Virol. (2001) 75(24):12161-8). In further embodiments, the LALA mutations are present in the antibody moiety in addition to the knobs-into-holes mutations.

In some embodiments, the antigen-binding moiety is an antibody that comprises the M252Y/S254T/T256E ("YTE") mutations in the Fc domain. The YTE mutations allow the simultaneous modulation of serum half-life, tissue distribution and activity of $IgG_1$ (see Dall'Acqua et al., J Biol Chem. (2006) 281:23514-24; and Robbie et al., Antimicrob Agents Chemother. (2013) 57(12):6147-53). In further embodiments, the YTE mutations are present in the antibody in addition to the knobs-into-holes mutations. In particular embodiments, the antibody has YTE, LALA and knobs-into-holes mutations or any combination thereof.

In particular embodiments, the antigen-binding moiety is an antibody, or antigen-binding fragment thereof, that binds to an antigen on the surface of a target cell, such as an immune cell. Immune cells are well known in the art. Non-limiting examples of immune cells include T cells, NK cells, and macrophages. The antigen-binding moiety may have the ability to activate the immune cell and enhance its anti-cancer activity. The antibody may or may not have ADCC activity. The antigen-binding moiety may also be further conjugated to a cytotoxic drug. In some embodiments, the antigen-binding moiety may bind to PD-1, LAG-3, TIM-3, TIGIT, CTLA-4, or TGF-beta. In other embodiments, the antigen-binding moiety may bind to an antigen on the surface of a target cell, such as a tumor cell. For example, the antigen-binding moiety may bind to FAP alpha, 5T4, Trop-2, PD-L1, HER-2, EGFR, Claudin 18.2, DLL-3, GCP3, or carcinoembryonic antigen (CEA).

In some embodiments, the antigen-binding moiety binds to guanyl cyclase C (GCC), carbohydrate antigen 19-9 (CA19-9), glycoprotein A33 (gpA33), mucin 1 (MUC1), insulin-like growth factor 1 receptor (IGF1-R), human epidermal growth factor receptor 2 (HER2), human epidermal growth factor receptor 3 (HER3), delta-like protein 3 (DLL3), delta-like protein 4 (DLL4), epidermal growth factor receptor (EGFR), glypican-3 (GPC3), c-MET, vascular endothelial growth factor receptor 1 (VEGFR1), vascular endothelial growth factor receptor 2 (VEGFR2), Nectin-4, Liv-1, glycoprotein NMB (GPNMB), prostates-specific membrane antigen (PSMA), Trop-2, carbonic anhydrase IX (CA9), endothelin B receptor (ETBR), six transmembrane epithelial antigen of the prostate 1 (STEAP1), folate receptor alpha (FR-α), SLIT and NTRK-like protein 6 (SLITRK6), carbonic anhydrase VI (CA6), ectonucleotide pyrophosphatase/phosphodiesterase family member 3 (ENPP3), mesothelin, trophoblast glycoprotein (TPBG), CD19, CD20, CD22, CD33, CD40, CD56, CD66e, CD70, CD74, CD79b, CD98, CD123, CD138, CD352, CD47, signal-regulatory protein alpha (SIRPα), Claudin 18.2, Claudin 6, BCMA, or EPCAM. In some embodiments, the antigen-binding moiety binds to an epidermal growth factor (EGF)—like domain of DLL3. In some embodiments, the antigen-binding moiety binds to a Delta/Serrate/Lag2 (DSL)—like domain of DLL3. In some embodiments, the antigen-binding moiety binds to an epitope located after the 374th amino acid of GPC3. In some embodiments, the antigen-binding moiety binds to a heparin sulfate glycan of GPC3. In some embodiments, the antigen-binding moiety binds to Claudin 18.2 and does not bind to Claudin 18.1. In some embodiments, the antigen-binding moiety binds to Claudin 18.1 with at least 10 times weaker binding affinity than to Claudin 18.2.

Exemplary antigen-binding moieties include trastuzumab, rituximab, brentuximab, cetuximab, panitumumab, GC33 (or a humanized version thereof), anti-EGFR antibody mAb806 (or a humanized version thereof), anti-dPNAG antibody F598, and antigen-binding fragments thereof. In some embodiments, the antigen-binding moiety has at least 90%, 91%, 92%, 93%, 94%, 95%, 96%, 97%, 98%, or 99% identity to trastuzumab, rituximab, brentuximab, cetuximab, or panitumumab, GC33 (or a humanized version thereof), anti-EGFR antibody mAb806 (or a humanized version thereof), anti-dPNAG antibody F598, or a fragment thereof. In some embodiments, the antigen-binding moiety comprises an antibody heavy chain with at least 90%, 91%, 92%, 93%, 94%, 95%, 96%, 97%, 98%, or 99% identity to the antibody heavy chain of trastuzumab, rituximab, brentuximab, cetuximab, panitumumab, GC33 (or a humanized version thereof), anti-EGFR antibody mAb806 (or a humanized version thereof), anti-dPNAG antibody F598, or a fragment thereof. In some embodiments, the antigen-binding moiety has an antibody light chain with at least 90%, 91%, 92%, 93%, 94%, 95%, 96%, 97%, 98%, or 99% identity to the antibody light chain of trastuzumab, rituximab, brentuximab, cetuximab, panitumumab, GC33 (or a humanized version thereof), anti-EGFR antibody mAb806 (or a humanized version thereof), anti-dPNAG antibody F598, or a fragment thereof. The antigen-binding moiety is fused to an IL-2 agonist polypeptide. In some embodiments, the antigen-binding moiety comprises the six complementarity-determining regions (CDRs) of trastuzumab, rituximab, brentuximab, cetuximab, panitumumab, GC33, anti-EGFR antibody mAb806, or anti-dPNAG antibody F598.

A number of CDR delineations are known in the art and are encompassed herein. A person of skill in the art can readily determine a CDR for a given delineation based on the sequence of the heavy or light chain variable region. The "Kabat" CDRs are based on sequence variability and are the most commonly used (Kabat et al., Sequences of Proteins of Immunological Interest, 5th Ed. Public Health Service, National Institutes of Health, Bethesda, Md. (1991)). "Chothia" CDRs refer to the location of the structural loops (Chothia & Lesk, J. Mol. Biol. (1987) 196:901-917). The "AbM" CDRs represent a compromise between the Kabat CDRs and Chothia structural loops, and are used by Oxford Molecular's AbM antibody modeling software. The "Contact" CDRs are based on an analysis of the available complex crystal structures. The residues from each of these CDRs are noted below in Table 1, in reference to common antibody numbering schemes. Unless otherwise specified herein, amino acid numbers in antibodies refer to the Kabat numbering scheme as described in Kabat et al., supra, including when CDR delineations are made in reference to Kabat, Chothia, AbM, or Contact schemes. Using this numbering system, the actual linear amino acid sequence may contain fewer or additional amino acids corresponding to a shortening of, or insertion into, a framework region (FR) or CDR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

TABLE 1

CDR Delineations According to Various Schemes

| CDR | Kabat | AbM | Chothia | Contact |
|---|---|---|---|---|
| VL-CDR1 | L24-L34 | L24-L34 | L26-L32 | L30-L36 |
| VL-CDR2 | L50-L56 | L50-L56 | L50-L52 | L46-L55 |
| VL-CDR3 | L89-L97 | L89-L97 | L91-L96 | L89-L96 |
| VH-CDR1 (Kabat nos.) | H31-H35B | H26-H35B | H26-H32 | H30-H35B |
| VH-CDR1 (Chothia nos.) | H31-H35 | H26-H35 | H26-H32 | H30-H35 |
| VH-CDR2 | H50-H65 | H50-H58 | H53-H55 | H47-H58 |
| VH-CDR3 | H95-H102 | H95-H102 | H95-H101 | H93-H101 |

In some embodiments, the CDRs are "extended CDRs," and encompass a region that begins or terminates according to a different scheme. For example, an extended CDR can be as follows: L24-L36, L26-L34, or L26-L36 (VL-CDR1); L46-L52, L46-L56, or L50-L55 (VL-CDR2); L91-L97 (VL-CDR3); H47-H55, H47-H65, H50-H55, H53-H58, or H53-H65 (VH-CDR2); and/or H93-H102 (VH-CDR3).

In some embodiments, the antigen-binding moiety binds to PDL1, and comprises a light chain having an amino acid sequence with at least 90%, 91%, 92%, 93%, 94%, 95%, 96%, 97%, 98%, or 99% identity to SEQ ID NO: 45, or a fragment thereof, and a heavy chain having an amino acid sequence with at least 90%, 91%, 92%, 93%, 94%, 95%, 96%, 97%, 98%, or 99% identity to SEQ ID NO: 46, or a fragment thereof. In some embodiments, the antigen-binding domain comprises CDR1, CDR2, and CDR3 from SEQ ID NO: 45, and CDR1, CDR2, and CDR3 from SEQ ID NO: 46.

In some embodiments, the antigen-binding moiety binds to PD-1, and comprises a light chain having an amino acid sequence with at least 90%, 91%, 92%, 93%, 94%, 95%, 96%, 97%, 98%, or 99% identity to SEQ ID NO: 44, or a fragment thereof, and a heavy chain having an amino acid sequence with at least 90%, 91%, 92%, 93%, 94%, 95%, 96%, 97%, 98%, or 99% identity to SEQ ID NO: 47, or a fragment thereof. In some embodiments, the antigen-binding domain comprises CDR1, CDR2, and CDR3 from SEQ ID NO: 44, and CDR1, CDR2, and CDR3 from SEQ ID NO: 47.

In some embodiments, the antigen-binding moiety binds to PD-1, and comprises a light chain having an amino acid sequence with at least 90%, 91%, 92%, 93%, 94%, 95%, 96%, 97%, 98%, or 99% identity to SEQ ID NO: 48, or a fragment thereof, and a heavy chain having an amino acid sequence with at least 90%, 91%, 92%, 93%, 94%, 95%, 96%, 97%, 98%, or 99% identity to SEQ ID NO: 49, or a fragment thereof. In some embodiments, the antigen-binding domain comprises CDR1, CDR2, and CDR3 from SEQ ID NO: 48, and CDR1, CDR2, and CDR3 from SEQ ID NO: 49.

In some embodiments, the antigen-binding moiety comprises one, two, or three antigen-binding domains. For example, the antigen-binding moiety is bispecific and binds to two different antigens selected from the group consisting of CD3, HER2, HER3, EGFR, 5T4, FAP alpha, Trop-2, GPC3, VEGFR2, Claudin 18.2 and PD-L1. In some embodiments, the bispecific antigen-binding moiety binds to two different epitopes of HER2. In other embodiments, the antigen-binding moiety is bispecific and binds to two different antigens selected from PD-1, PD-L1, CTLA-4, CD47, CD3, TIM-3, LAG-3 and TIGIT.

2. Other Domains of Carrier Moieties

The carrier moieties may also comprise other domains that are not antigen-binding. For example, an antibody Fc domain (e.g., a human $IgG_1$, $IgG_2$, $IgG_3$, or $IgG_4$ Fc), a polymer (e.g., PEG), an albumin (e.g., a human albumin) or a fragment thereof, or a nanoparticle can be used.

By way of example, the cytokine agonist polypeptide (e.g., IL-2, IL-21, IL-5, or any cytokine disclosed herein) and its antagonist may be fused to an antibody Fc domain, forming an Fc fusion protein. In some embodiments, the cytokine agonist polypeptide is fused (directly or through a peptide linker) to the C-terminus or N-terminus of one of the Fc domain polypeptide chains, and the cytokine mask is fused to the corresponding C-terminus or N-terminus of the other Fc domain polypeptide chain through a cleavable peptide linker, wherein the two Fc domain polypeptide chains contain mutations that allow the specific pairing of the two different Fc chains. In some embodiments, the Fc domain comprises the holes-into-holes mutations described above. In further embodiments, the Fc domain may comprise also the YTE and/or LALA mutations described above.

The carrier moiety of the prodrug may comprise an albumin (e.g., human serum albumin) or a fragment thereof. In some embodiments, the carrier moiety comprises an albumin fragment (e.g., a human serum albumin fragment) that is about 10 or more, 20 or more, 30 or more 40 or more, 50 or more, 60 or more, 70 or more, 80 or more, 90 or more, 100 or more, 120 or more, 140 or more, 160 or more, 180 or more, 200 or more, 250 or more, 300 or more, 350 or more, 400 or more, 450 or more, 500 or more, or 550 or more amino acids in length. In some embodiments, the albumin fragment is between about 10 amino acids and about 584 amino acids in length (such as between about 10 and about 20, about 20 and about 40, about 40 and about 80, about 80 and about 160, about 160 and about 250, about 250 and about 350, about 350 and about 450, or about 450 and about 550 amino acids in length). In some embodiments, the albumin fragment includes the Sudlow I domain or a fragment thereof, or the Sudlow II domain or the fragment thereof.

D. Linker Components of the Prodrugs

The cytokine agonist polypeptide may be fused to the carrier moiety with or without a peptide linker. The peptide linker is noncleavable. In some embodiments, the peptide linker is selected from SEQ ID NOs: 27-34. In particular embodiments, the peptide linker comprises the amino acid sequence GGGGSGGGGSGGGGS (SEQ ID NO: 30).

The masking moiety may be fused to the cytokine moiety or to the carrier through a non-cleavable linker or without a peptide linker.

II. Pharmaceutical Compositions

Pharmaceutical compositions comprising the prodrugs and muteins (i.e., the active pharmaceutical ingredient or API) of the present disclosure may be prepared by mixing the API having the desired degree of purity with one or more optional pharmaceutically acceptable excipients (see, e.g., *Remington's Pharmaceutical Sciences,* 16th Edition., Osol, A. Ed. (1980)) in the form of lyophilized formulations or aqueous solutions. Pharmaceutically acceptable excipients (or carriers) are generally nontoxic to recipients at the dosages and concentrations employed, and include, but are not limited to: buffers containing, for example, phosphate, citrate, succinate, histidine, acetate, or another inorganic or organic acid or salt thereof; antioxidants including ascorbic acid and methionine; preservatives (such as octadecyldim-ethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pen-tanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, gluta-mine, asparagine, histidine, arginine, or lysine; monosac-charides, disaccharides, and other carbohydrates including sucrose, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffers are used to control the pH in a range which optimizes the therapeutic effectiveness, especially if stability is pH dependent. Buffers are preferably present at concen-trations ranging from about 50 mM to about 250 mM. Suitable buffering agents for use with the present invention include both organic and inorganic acids and salts thereof, such as citrate, phosphate, succinate, tartrate, fumarate, gluconate, oxalate, lactate, and acetate. Additionally, buffers may comprise histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hex-amethonium chloride; benzalkonium halides (e.g., chloride, bromide, iodide), benzethonium chloride; thimerosal, phe-nol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter- and intramolecular interactions. Tonicity agents can be present in any amount between 0.1% to 25% by weight, or more preferably between 1% to 5% by weight, taking into account the relative amounts of the other ingre-dients. Preferred tonicity agents include polyhydric sugar alcohols, preferably trihydric or higher sugar alcohols, such as glycerin, erythritol, arabitol, xylitol, sorbitol and manni-tol.

Non-ionic surfactants or detergents (also known as "wet-ting agents") are present to help solubilize the therapeutic agent as well as to protect the therapeutic protein against agitation-induced aggregation, which also permits the for-mulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbi-tan monoethers (TWEEN®-20, TWEEN®-80, etc.), lauro-macrogol 400, polyoxyl 40 stearate, polyoxyethylene hydro-genated castor oil 10, 50 and 60, glycerol monostearate, sucrose fatty acid ester, methyl cellulose and carboxymethyl cellulose. Anionic detergents that can be used include sodium lauryl sulfate, dioctyle sodium sulfosuccinate and dioctyl sodium sulfonate. Cationic detergents include ben-zalkonium chloride or benzethonium chloride.

The choice of pharmaceutical carrier, excipient or diluent may be selected with regard to the intended route of admin-istration and standard pharmaceutical practice. Pharmaceu-tical compositions may additionally comprise any suitable binder(s), lubricant(s), suspending agent(s), coating agent(s) or solubilizing agent(s).

There may be different composition/formulation require-ments dependent on the different delivery systems. By way of example, pharmaceutical compositions useful in the pres-ent invention may be formulated to be administered using a mini-pump or by a mucosal route, for example, as a nasal spray or aerosol for inhalation or ingestible solution, or parenterally in which the composition is formulated by an injectable form, for delivery, by, for example, an intrave-nous, intramuscular or subcutaneous route.

In some embodiments, the pharmaceutical composition of the present disclosure is a lyophilized protein formulation. In other embodiments, the pharmaceutical composition may be an aqueous liquid formulation.

III. Methods of Treatment

The cytokine prodrug and fusion molecules can be used to treat a disease, depending on the antigen bound by the antigen-binding domain. In some embodiments, the cyto-kine prodrug or fusion molecule is used to treat cancer. In some embodiments, the cytokine prodrug or fusion molecule is used to treat an infection.

In some embodiments, a method of treating a disease (such as cancer, a parasitic infection, a viral infection, or a bacterial infection) in a subject comprises administering to the subject an effective amount of a cytokine prodrug or a fusion molecule.

In some embodiments, the cancer is a solid cancer. In some embodiments, the cancer is a blood cancer or a solid tumor. Exemplary cancers that may be treated include, but are not limited to, leukemia, lymphoma, kidney cancer, bladder cancer, urinary tract cancer, cervical cancer, brain cancer, head and neck cancer, skin cancer, uterine cancer, testicular cancer, esophageal cancer, liver cancer, colorectal cancer, stomach cancer, squamous cell carcinoma, prostate cancer, pancreatic cancer, lung cancer such as non-small cell lung cancer, cholangiocarcinoma, breast cancer, and ovarian cancer.

In some embodiments, the cytokine prodrug or fusion molecule is used to treat a viral infection. In some embodi-ments, the virus causing the viral infection is hepatitis C virus (HCV), hepatitis B virus (HBV), human immunode-ficiency virus (HIV), or human papilloma virus (HPV). In some embodiments, the antigen-binding moiety binds to a viral antigen.

In some embodiments, the cytokine prodrug or fusion molecule is used to treat a bacterial infection such as sepsis. In some embodiments, the bacteria causing the bacterial infection is drug-resistant bacteria. In some embodiments, the antigen-binding moiety binds to a bacterial antigen.

Generally, dosages and routes of administration of the present pharmaceutical compositions are determined according to the size and conditions of the subject, according to standard pharmaceutical practice. In some embodiments, the pharmaceutical composition is administered to a subject through any route, including orally, transdermally, by inha-lation, intravenously, intra-arterially, intramuscularly, direct application to a wound site, application to a surgical site, intraperitoneally, by suppository, subcutaneously, intrader-mally, transcutaneously, by nebulization, intrapleurally, intraventricularly, intra-articularly, intraocularly, intracranially, or intraspinally. In some embodiments, the composition is administered to a subject intravenously.

In some embodiments, the dosage of the pharmaceutical composition is a single dose or a repeated dose. In some embodiments, the doses are given to a subject once per day, twice per day, three times per day, or four or more times per day. In some embodiments, about 1 or more (such as about 2, 3, 4, 5, 6, or 7 or more) doses are given in a week. In some embodiments, the pharmaceutical composition is administered weekly, once every 2 weeks, once every 3 weeks, once every 4 weeks, weekly for two weeks out of 3 weeks, or weekly for 3 weeks out of 4 weeks. In some embodiments, multiple doses are given over the course of days, weeks, months, or years. In some embodiments, a course of treatment is about 1 or more doses (such as about 2, 3, 4, 5, 7, 10, 15, or 20 or more doses).

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. It is understood that aspects and variations of the invention described herein include "consisting" and/or "consisting essentially of" aspects and variations. All publications and other references mentioned herein are incorporated by reference in their entirety. Although a number of documents are cited herein, this citation does not constitute an admission that any of these documents forms part of the common general knowledge in the art.

IV. Exemplary Embodiments

Further, particular embodiments of the present disclosure are described as follows. These embodiments are intended to illustrate the compositions and methods described in the present disclosure and are not intended to limit the scope of the present disclosure.

1. A prodrug comprising a cytokine moiety, a masking moiety, and a carrier moiety, wherein:

a) the masking moiety binds to the cytokine moiety and inhibits an intended biological activity of the cytokine;

b) the carrier moiety comprises an antigen binding moiety which binds to an antigen expressed on the surface of a cell; and c) the masking moiety is linked directly or indirectly to the carrier moiety through a noncleavable peptide linker or without a peptide linker;

and wherein the activity of the prodrug is higher in stimulating a cell which expresses both the antigen targeted by the carrier moiety and the receptor(s) of the cytokine than its activity in stimulating a cell which expresses the receptor(s) of the cytokine but not the antigen targeted by the carrier moiety.

2. A prodrug comprising a cytokine moiety, a masking moiety, and a carrier moiety, wherein:

a) the masking moiety binds to the cytokine moiety and inhibits an intended biological activity of the cytokine;

b) the carrier moiety comprises an antigen binding moiety which binds to an antigen expressed on the surface of a cell; and c) the masking moiety is linked directly or indirectly to the carrier moiety through a noncleavable peptide linker or without a peptide linker;

and wherein the prodrug is activated at a disease site where there are cells expressing both the antigen targeted by the carrier moiety and the receptor(s) of the cytokine, or a biological activity of the prodrug is increased by at least 2 folds, at least 5 folds, or at least 10 folds at a disease site where there are cells expressing both the antigen targeted by the carrier moiety and the receptor(s) of the cytokine.

3. The prodrug of embodiment 1 or 2, wherein the receptor of the cytokine moiety comprises two or more subunits.

4. The prodrug of embodiment 1 or 2, wherein the carrier comprises an antigen-binding moiety, wherein the antigen is expressed on an immune cell.

5. The prodrug of embodiment 1 or 2, wherein the carrier moiety comprises an antigen-binding moiety, wherein the antigen is selected from PD-1, PD-L1, CTLA-4, TIGIT, TIM-3, LAG-3, CD25, CD16a, CD16b, NKG2D, NKP44, NKP30, CD19, CD20, CD38, and BCMA.

6. The prodrug of any of embodiments 1-5, wherein the cytokine moiety comprises a cytokine selected from an IL-2 agonist polypeptide, an IL-7 agonist polypeptide, an IL-9 agonist polypeptide, an IL-15 agonist polypeptide, and an IL-21 agonist polypeptide.

7. The prodrug of any of embodiments 1-5, wherein the cytokine is selected from an IL-la agonist polypeptide, an IL-10 agonist polypeptide, an IL-4 agonist polypeptide, an IL-5 agonist polypeptide, an IL-6 agonist polypeptide, an IL-8 agonist polypeptide, an IL-10 agonist polypeptide, an IL-12 agonist polypeptide, an IL-17 agonist polypeptide, an IL-18 agonist polypeptide, an IL-22 agonist polypeptide, an IL-23 agonist polypeptide, an IL-31 agonist polypeptide, an IL-33 agonist polypeptide, an IL-36 agonist polypeptide, an Interferon-alpha agonist polypeptide, an interferon gamma agonist polypeptide, a 4-1BB ligand, an OX-40 ligand, and a CD-40 ligand.

8. The prodrug of any of embodiments 1-7, wherein the masking moiety is an extracellular domain (ECD) of a receptor of the cytokine.

9. The prodrug of any of embodiments 1-6, wherein the cytokine is an IL-7 agonist polypeptide; and wherein the masking moiety is the extracellular domain of IL-7 receptor α(IL-7Rα ECD) or a functional analog thereof.

10. The prodrug of any of embodiments 1-6, wherein the cytokine is an IL-21 agonist polypeptide; and wherein the masking moiety is the extracellular domain of IL-21 receptor α(IL-21Rα ECD) or a functional analog thereof.

11. The prodrug of any of embodiments 1-6, wherein the cytokine is an IL-2 agonist polypeptide or an IL-15 agonist polypeptide; and wherein the masking moiety is the extracellular domain of IL-2 receptor β(IL-2R13 ECD).

12. The prodrug of any of embodiments 1-6, wherein the cytokine is an IL-21 agonist polypeptide; and wherein the masking moiety is a Fab, a single chain Fv (scFv) or a single domain antibody against IL-21.

13. The prodrug of any of embodiments 1-6, wherein the cytokine is an IL-2 agonist polypeptide; and wherein the masking moiety is a Fab, a single chain Fv (scFv), or a single domain antibody against IL-2.

14. The prodrug of any of embodiments 1-6, wherein the cytokine is an IL-15 agonist polypeptide; and wherein the masking moiety is a Fab, a single chain Fv (scFv), or a single domain antibody against IL-15.

15. The prodrug of any of embodiments 1-6, 11 and 14, wherein the cytokine moiety comprises an IL-15 agonist polypeptide, wherein the fusion molecule further comprises the sushi domain of IL-15 receptor α(IL-15Rα sushi domain).

16. The prodrug of any of embodiment 10 or 12, wherein the IL-21 agonist polypeptide comprises an amino acid sequence as SEQ ID NO: 1, or at least 90% identical as that of SEQ ID NO: 1.

17. The prodrug of embodiment 10 or 16, wherein the masking moiety is IL-21Rα-ECD or a functional analog thereof, which comprises an amino acid sequence selected from SEQ ID NO: 12, 63-72, and 73, or at least 90% identical as that of SEQ ID NO: 12.

18. The prodrug of embodiment 12 or 16, wherein the masking moiety is an scFv which binds to human IL-21; and wherein the scFv comprises an amino acid sequence of SEQ ID NO: 20 or 21.

19. The prodrug of embodiment 11 or 13, wherein the IL-2 agonist polypeptide comprises an amino acid sequence of SEQ ID NO: 6, or 61, or at least 95% identical as that of SEQ ID NO: 6, or 61.

20. The prodrug of embodiment 11 or 14, wherein the IL-15 agonist polypeptide comprises an amino acid sequence of SEQ ID NO: 7, or at least 95% identical as that of SEQ ID NO: 7.

21. The prodrug of embodiment 11, 19, or 20, wherein the masking moiety comprises the IL-2Rβ-ECD or a functional analog thereof; wherein the IL-2-Rβ-ECD comprises an amino acid sequence of SEQ ID NO: 11 or at least 95% identical as that of SEQ ID NO: 11.

22. The prodrug of any of embodiments 6, 13 or 19, wherein the masking moiety is an scFv which binds to IL-2, wherein the scFv inhibits or interferes with the interaction between IL-2 and IL-2Rα, the interaction between IL-2 and IL-2Rβ, and/or the interaction between IL-2 and IL-2Rγ.

23. The prodrug of any of embodiments 6, 14, 15 or 20, wherein the masking moiety is an scFv which binds to IL-15, wherein the scFv inhibits or interferes with the interaction between IL-15 and IL-2Rβ, and/or IL-2 and IL-2Rγ.

24. The prodrug of any of embodiments 6, 12 or 16, wherein the masking moiety is an scFv which binds to IL-21, wherein the scFv inhibits or interferes with the interaction between IL-21 and IL-21Rα, and/or IL-21 and IL-2Rγ.

25. The prodrug of embodiment 6, wherein the masking moiety is an scFv which binds to a cytokine selected from IL-2, IL-7, IL-9, IL-15, or IL-21; wherein the scFv inhibits or interferes with the interaction between the cytokine and IL-2Rγ; and wherein the prodrug has a half-life in a non-human primate or a human that is at least 20 times, at least 50 times, at least 100 times, at least 150 times, or at least 200 times longer than that of the corresponding wild type cytokine.

26. A prodrug which comprises a carrier moiety, a cytokine moiety, and a masking moiety; wherein:

a) the cytokine moiety is selected from an IL-2 agonist polypeptide, an IL-7 agonist polypeptide, an IL-9 agonist polypeptide, an IL-15 agonist polypeptide, or an IL-21 agonist polypeptide;

b) the masking moiety is an scFv which binds to the cytokine moiety;

c) the scFv inhibits or interferes with the interaction between the cytokine and IL-2Rγ; and d) wherein the prodrug has a half-life in a non-human primate or a human that is at least 20 times, at least 50 times, at least 100 times, at least 150 times, or at least 200 times longer than that of the wild type cytokine.

27. The prodrug of any of embodiments 22-25, wherein the scFv binds to the cytokine with a $K_D$ of 1-10 nM.

28. The prodrug of any of embodiments 22-25, wherein the scFv binds to the cytokine with a $K_D$ of 10-100 nM.

29. The prodrug of any of embodiments 22-25, wherein the scFv binds to the cytokine with a $K_D$ of 100-1000 nM.

30. The prodrug of embodiment 13 or 19, wherein the masking moiety is scFv which binds to IL-2, wherein the scFv comprises the same heavy chain and light chain CDRs as that of hybridoma 4E12B2D10.

31. The prodrug of embodiment 13 or 19, wherein the masking moiety is scFv which binds to IL-2, wherein the scFv comprises an amino acid sequence of SEQ ID NO: 22 or 23, or at least 95% identical as that of SEQ ID NO: 22 or 23.

32. The prodrug of embodiment 14 or 20, wherein the masking moiety is scFv which binds to IL-15, wherein the scFv comprises the same heavy chain and light chain CDRs as that of the IL-15 antibody 146B7, 146H5, or 404E4.

33. The prodrug of embodiment 14 or 20, wherein the masking moiety is scFv which binds to IL-15, wherein the scFv comprises an amino acid sequence of SEQ ID NO: 18 or 19.

34. The prodrug of any of the embodiments 1-32, wherein the prodrug does not contain a cleavable peptide linker.

35. The prodrug of embodiment 1, wherein the prodrug comprises two light chains with an amino acid sequence of SEQ ID NO: 44, and two heavy chain polypeptide chains whose amino acid sequences respectively comprise
SEQ ID NOs: 35 and 36,
SEQ ID NOs: 37 and 36,
SEQ ID NOs: 37 and 38,
SEQ ID NOs: 39 and 41, or
SEQ ID NOs: 42 and 43.

36. The prodrug of embodiment 1, wherein the prodrug comprises two light chains with an amino acid sequence of SEQ ID NO: 50, and two heavy chain polypeptide chains whose amino acid sequences respectively comprise
SEQ ID NOs: 51 and 54,
SEQ ID NOs: 51 and 55,
SEQ ID NOs: 51 and 56,
SEQ ID NOs: 52 and 54,
SEQ ID NOs: 53 and 58,
SEQ ID NOs: 53 and 59, or
SEQ ID NOs: 52 and 57.

37. A pharmaceutical composition comprising the prodrug of any one of the embodiments 1-36 and a pharmaceutically acceptable excipient.

38. A polynucleotide or polynucleotides encoding the prodrug of any one of embodiments 1-36.

39. An expression vector or vectors comprising the polynucleotide or polynucleotides of embodiment 38.

40. A host cell comprising the vector(s) of embodiment 39.

41. A method of making the prodrug of any one of embodiments 1-36, comprising culturing the host cell of embodiment 46 under conditions that allow expression of the prodrug, wherein the host cell is a mammalian cell, and isolating the prodrug.

42. A method of treating a cancer, an autoimmune disease, or an infectious disease, or stimulating the immune system, in a patient in need thereof, comprising administering to the patient a therapeutically effective amount of the pharmaceutical composition of embodiment 37.

43. A prodrug of any one of embodiments 1-36, for use in treating a cancer, an autoimmune disease or an infectious disease, or stimulating the immune system, in a patient in need thereof.

44. Use of a prodrug of any one of embodiments 1-36, for the manufacture of a medicament for treating a cancer, an autoimmune disease, or an infectious disease, or stimulating the immune system, in a patient in need thereof.

45. The method of embodiment 41, the prodrug for use of embodiment 42 or the fusion molecule for use of embodiment 43, or the use of embodiment 44, wherein the patient has HIV, HBV, HCV, or HPV infection; an autoimmune disease selected from lupus, type I diabetes, psoriasis, dermatomyositis, GvHD, or rheumatoid arthritis; or a cancer selected from the group consisting of breast cancer, lung cancer, pancreatic cancer, esophageal cancer, medullary thyroid cancer, ovarian cancer, uterine cancer, prostate cancer, testicular cancer, colorectal cancer, and stomach cancer.

46. A prodrug which comprises a carrier moiety, a cytokine moiety, and a masking moiety; wherein:

a) the cytokine moiety is selected from an IL-2 agonist polypeptide, an IL-7 agonist polypeptide, an IL-9 agonist polypeptide, an IL-15 agonist polypeptide, or an IL-21 agonist polypeptide;

b) the masking moiety is an scFv which binds to the cytokine moiety;

c) the scFv inhibits or interferes with the interaction between the cytokine and IL-2Rγ; and d) wherein the prodrug has an area under curve (AUC) in a non-human primate or a human that is at least 20 times, at least 50 times, at least 100 times, at least 150 times, or at least 200 times longer than that of the wild type cytokine.

In order that this invention may be better understood, the following examples are set forth. These examples are for purposes of illustration only and are not to be construed as limiting the scope of the invention in any manner.

EXAMPLES

The materials and methods for the experiments described in Examples 1 and 2 are as follows.

SEC-HPLC Analysis

SEC-HPLC was carried out using an Agilent 1100 Series of HPLC system with a TSKgel G3000SWXL column (7.8 mmIDX 30 cm, 5 μm particle size) ordered from Tosoh Bioscience. A sample of up to 100 μl was loaded. The column was run with a buffer containing 200 mM $K_3PO_4$, 250 mM KCl, pH 6.5. The flow rate was 0.5 ml/min. The column was run at room temperature.

Proteolytic Treatment

The proteases, human MMP2, human MMP9, mouse MMP2 and mouse MMP9 were purchased from R&D systems. The protease digestion was carried out by incubating 10 μg-50 μg of prodrugs with 1 μg of human MMP2, human MMP9 mouse MMP2 or mouse MMP2 or mouse MMP9 in the HBS buffer (20 mM HEPES, 150 mM $NaCl_2$, pH 7.4) containing 2 mM CaCl2 and 10 μM $ZnCl_2$ at 37° C. for 12 hours.

Cell-Based Activity Assay

The prodrugs prior to the protease digestion and the control samples were tested by the cell-based activity assay. Briefly, NK92 cells were grown in the RPMI-1640 medium supplemented with L-glutamine, 10% fetal bovine serum, 10% non-essential amino acids, 10% sodium pyruvate, and 55 μM beta-mercaptoethanol. NK92 cells were non-adherent and maintained at $1\times10^5$–$1\times10^6$ cells/ml in medium with 100 ng/ml of IL-2. Generally, cells were split twice per week. For bioassays, it was best to use cells no less than 48 hours after passage. IL-21 functional activity was determined by culturing NK92 cells at $5\times10^4$ cells/well with serial dilutions of the samples in the presence of a constant amount of IL-2 for 2 days. Supernatants were then assayed for interferon-γ by ELISA.

Mino IL-21 Viability Assay

The Mino cell viability assay is carried out following the protocol below:

a) Perform serial dilutions of test articles in 50 uL assay medium (RPMI 1640, 10% Fetal Bovine Serum, NEAA, sodium pyruvate, 55 μM b-mercaptoethanol) in 96 well tissue culture plate.

b) Add 20,000 Mino cells/well in 50 μL assay medium.

c) Culture for 3 or 5 days.

d) Add 100 μL/well Cell Titer Glo (Promega). Cell Titer-Glo provides a measure of cell viability by providing a quantitative assessment of ATP.

e) Measure luminescence.

Ki67 Activation Assay with PBMC Primary Cells

Human PBMCs were stimulated with anti-CD3 antibody, OKT3 at 100 ng/mL for 2 days, followed by three-time washes, then were rested for 3 days in regular cell culture medium in 37° C., 5% $CO_2$ incubator. After that stimulated/rested PBMCs were seeded at 200K cells/well of 96-well plates and were treated with test articles as indicated at various concentrations for 5 days before subject to cell staining and flow cytometry analysis for Ki67 in PD-1$^+$ CD4$^+$ and PD-1-CD4+ cell populations (all Abs used for cell staining were purchased from BD).

Example 1: Construction of Anti-PD-1 Antibody-IL-21 Prodrug Fusion Molecules An anti-PD-1 antibody-based IL-21 prodrug was constructed with two identical light chains (with an amino acid sequence as shown in SEQ ID NO: 44). A first heavy chain polypeptide chain (with an amino acid sequence as shown in SEQ ID NO: 42) and a second heavy chain polypeptide chain (with an amino acid sequence as shown SEQ ID NO: 76). The molecule was transiently expressed and purified (lot #PW04-38).

A second PD-1 antibody-based IL-21 prodrug with the scFv as the masking moiety was also expressed and purified (Lot #PW05-68).

In addition, as a control, the anti-PD-1 antibody-IL-21 fusion molecule without the mask was also expressed and purified (Lot #PW05-67).

Further, a second control, the anti-PD-1 antibody-IL-21 mutein (R9ER76A) fusion molecule without the mask was also expressed and purified (Lot #PW09-02).

Example 2: Biological Activities of Anti-PD-1 Antibody-IL-21 Prodrug Fusion Molecules The binding of the prodrug molecules and several control molecules to the Mino cells were tested by FACS. The results on FIG. 2 show that both the PD-1 antibody and the Fc-IL-21 fusion molecule were able to bind to the Mino cells, indicating that the Mino cells express both the PD-1 and the receptors for IL-21. The results showed that both of the Fc-based IL-21 prodrug molecules had no binding to the cells, suggesting the IL-21 cytokine moieties have been masked by the corresponding masking moiety. However, the PD-1 antibody-based IL-21 prodrug molecules and fusion molecules were able to bind to the Mino cells.

Cell-based activity of the molecules were assessed using NK92 cells, a natural killer (NK) cell line. The results are shown in FIG. 3. The data show that without activation, the prodrug molecule with the IL-21a ECD as the masking moiety (Lot #PW04-38) had minimum activity while the prodrug with an scFv as the masking moiety (Lot #PW05-68) had an activity ~1000 times lower than the one without the masking moiety (PW04-67). The data show that the bioassay activities of the prodrugs were significantly enhanced by the protease MMP2 treatment.

To test the tumor killing activity of the fusion molecules, Mino cells were used. Mino cells are a mantle cell lymphoma cell line that expresses both PD-1 and receptors for IL-21 (Harington et al., *Leuk Lymphoma* (2019) 60(10): 2498-2507 and Gelebart et al., *Leukemia* (2009) 23:1836-1846). The Mino viability assay results are shown in FIGS. 4A and 4B. Surprisingly, the anti-PD-1 antibody-based IL-21 prodrugs (Lots #PW04-38 and PW05-68) had significant activities prior to activation, while the control molecule (PD-1 antibody-IL-21R9E/R76A fusion molecule, Lot #PW09-02) had no or little activity. The results demonstrate that the Anti-PD-1 IL-21 fusion molecule was activated through "cis-biding," i.e., through binding to both the PD-1 and the IL-21 receptor(s). Cis-binding of the PD-1 antibody to the PD-1 antigen on the cell surface and the cytokine to its receptor on the same cell surface may have unraveled the masking effect of the masking moiety. It is therefore expected that prodrugs without cleavable peptide linker may be "activated" in a disease site such as a tumor because the local immune cells may express both the antigen targeted by the carrier and the receptor(s), which bind the cytokine moiety (e.g., IL-21).

Example 3: Construction of Anti-PD-1 Antibody-IL-15 Prodrug Fusion Molecules A series of anti-PD-1 antibody-based IL-15 prodrugs were constructed, where the IL-15 moiety (i) was masked with an scFv 215β, (ii) was masked an scFv 215γ, (iii) had no mask (215β Ref), or (iv) had mutations but no mask (PD1/IL15 mutein (M2)). The anti-PD-1 antibody in these prodrugs comprises two identical light chains with an amino acid sequence of SEQ ID NO: 44 and two identical heavy chains with an amino acid sequence of SEQ ID NO: 47.

The Fc-based prodrug 215β is a heterodimer comprising amino acid sequence ID NOs: 16 and 17.

The anti-PD-1 antibody-based prodrug 215γ comprises two identical light chains (SEQ ID NO: 44), a first heavy chain fusion polypeptide chain with an amino acid sequence of SEQ ID NO: 37 and a second heavy chain fusion polypeptide chain with an amino acid sequence of SEQ ID NO: 77.

215β Ref is an IL-15 mutein(D30N/E64Q/N65D)—Fc fusion molecule.

PD1/IL15 mutein (M2) is an anti-PD-1-antibody fused with an IL-15 mutein wherein the IL-15 agonist comprises mutations E46G, V49R, E64Q, D30N, and N1G.

All the samples were expressed by CHO cells and purified using a Protein A affinity chromatography followed by additional chromatography steps.

Example 4: Biological Activities of Anti-PD-1 Antibody-IL-15 Prodrug Fusion Molecules The IL-15 prodrugs were assessed for their ability to stimulate Ki67 expression in PBMC cells obtained from human donors. FIGS. 5A-5C show the results of Ki67 activation of the CD4⁺ T cells in PBMC after treatment. FIG. 5A shows the results of Ki67 activation of CD4+ T cells without PD-1 expression. FIG. 5B shows the results of Ki67 activation of CD4+ T cells with PD-1 expression. FIG. 5C shows the $EC_{50}$ values of the testing articles with CD4+ T cells without and with PD-1 expression. It also showed the fold of changes of the EC50 values between the CD4+ T cells without and with PD-1 expression. Surprisingly, the data showed that 215γ had significantly higher Ki67 activity with CD4⁺ cells expressing PD-1 than the ones without PD-1 expression, indicating that the prodrug 215γ was able to be activated without protease cleavage when it was acting with the cells expressing both the antigen PD-1 and the receptors for the cytokine IL-15.

Example 5: Anti-PD-1 Antibody-IL-2 Prodrug Fusion Molecules

An anti-PD-1 antibody-based IL-2 prodrugs was similarly constructed. The prodrug, PD-1/IL-2v*, comprises two identical light chains (SEQ ID NO: 44) and two heavy chain fusion polypeptides (SEQ ID NOs: 24 and 25, respectively). The IL-2 moiety is an IL-2 mutein, and the mask in the prodrug is an IL-2 receptor β extracellular domain. The IL-2 prodrug was assessed for its ability to stimulate Ki67 expression in PBMC cells obtained from human donors.

FIGS. 6A and 6B show the results of Ki67 activation in the CD4⁺ T cells from PBMC after treatment with an anti-PD-1 antibody (PD-1), a negative control, or PD-1/IL-2v*. The negative control was an IgG₁ antibody against human Claudin 18.2. All the samples were expressed by CHO cells and purified using a Protein A affinity chromatography followed by additional chromatography steps. FIG. 6A shows the results of Ki67 activation in CD4⁺ T cells without PD-1 expression. FIG. 6B shows the results of Ki67 activation in CD4⁺ T cells with PD-1 expression. Surprisingly, the data showed that the prodrug PD-1/IL2V* had significantly higher Ki67-inducing activity on CD4⁺ cells expressing PD-1 than on those without PD-1 expression. These results indicate that PD-1/IL-2v* was able to be activated without protease cleavage when it was acting on cells expressing both the antigen PD-1 and the receptors for the cytokine IL-2.

Collectively the above data indicate that the cytokine prodrugs were able to be activated at a site where there were cells were expressing both the receptors for the cytokines and the antigens targeted by the carrier moiety. It was surprising that the prodrugs with carriers having antigen-binding moieties were able to be activated without protease cleavage. While not wishing to be bound by theory, we expect that the antigen-binding domain of the carrier moiety targets the prodrug molecules to the surface of the cells expressing the antigens and this allows the cytokine receptors on the cell surface to compete effectively with the mask moiety of the prodrug. This process culminates in protease cleavage-free activation of the prodrug via displacement of the masking moiety the cytokine receptors on the cell surface, as illustrated in FIG. 7.

Cells like exhausted Teff cells express both the antigen (e.g., PD-1) and the receptors for the cytokine (e.g., IL-2Rβ and IL-2Rγ). Exhausted Teff cells are in general localized at tumor microenvironment but in the normal tissues. This differential distribution of the cells expressing the antigens and the cytokine receptors provides the disease site-specific activation of the prodrugs. Such target specificity would also result in enhanced safety for the cytokine therapeutics.

SEQUENCES
human IL-21
                                                                          SEQ ID NO: 1
QGQDRHMIRM RQLIDIVDQL KNYVNDLVPE FLPAPEDVET NCEWSAFSCF QKAQLKSANT

GNNERIINVS IKKLKRKPPS TNAGRRQKHR LTCPSCDSYE KKPPKEFLER FKSLLQKMIH

QHLSSRTHGS EDS

IL-21 Mutein A
                                                                          SEQ ID NO: 2
QGQDRHMIRM RQLIDIVAQL KNYVNDLVPE FLPAPEDVET NCEWSAFSCF QKAQLKSANT

GNNERIINVS IKKLKRKPPS TNAGRRQKHR LTCPSCDSYE KKPPKEFLER FKSLLQKMIH

QHLSSRTHGS EDS

IL-21 Mutein B
                                                                          SEQ ID NO: 3
QGQDRHMIRM RQLIDIVKQL KNYVNDLVPE FLPAPEDVET NCEWSAFSCF QKAQLKSANT

GNNERIINVS IKKLKRKPPS TNAGRRQKHR LTCPSCDSYE KKPPKEFLER FKSLLQKMIH

QHLSSRTHGS EDS

IL-21 Mutein C
                                                                          SEQ ID NO: 4
QGQDRHMIRM RQLIDIVDQL KNYVNDLVPE FLPAPEDVET NCEWSAFSCF QKAQLKSANT

GNNERIINVS IKKLKRKPPS TNAGRRQKHR LTCPSCDSYE KKPPKEFLRR FKSLLQKMIH

QHLSSRTHGS EDS

IL-21 Mutein D
                                                                          SEQ ID NO: 5
QGQDRHMIRM RQLIDIVDKL KNYVNDLVPE FLPAPEDVET NCEWSAFSCF QKAQLKSANT

GNNERIINVS IKKLKRKPPS TNAGRRQKHR LTCPSCDSYE KKPPKEFLRR FKSLLQKMIH

QHLSSRTHGS EDS

Human IL-2
                                                                          SEQ ID NO: 6
APTSSSTKKT QLQLEHLLLD LQMILNGINN YKNPKLTRML TFKFYMPKKA TELKHLQCLE

EELKPLEEVL NLAQSKNFHL RPRDLISNIN VIVLELKGSE TTFMCEYADE TATIVEFLNR

WITFCQSIIS TLT

Human IL-15
                                                                          SEQ ID NO: 7
NWVNVISDLK KIEDLIQSMH IDATLYTESD VHPSCKVTAM KCFLLELQVI SLESGDASIH

DTVENLIILA NNSLSSNGNV TESGCKECEE LEEKNIKEFL QSFVHIVQMF INT

Human IL-15 Rα sushi domain
                                                                          SEQ ID NO: 8
ITCPPPMSVE HADIWVKSYS LYSRERYICN SGFKRKAGTS SLTECVLNKA TNVAHWTTPS

LKCIRDPALV HQRPA

Human IL-7
                                                                          SEQ ID NO: 9
DCDIEGKDGK QYESVLMVSI DQLLDSMKEI GSNCLNNEFN FFKRHICDAN KEGMFLFRAA

RKLRQFLKMN STGDFDLHLL KVSEGTTILL NCTGQVKGRK PAALGEAQPT KSLEENKSLK

EQKKLNDLCF LKRLLQEIKT CWNKILMGTK EH

Human IL-9
                                                                          SEQ ID NO: 10
QGCPTLAGIL DINFLINKMQ EDPASKCHCS ANVTSCLCLG IPSDNCTRPC FSERLSQMTN

TTMQTRYPLI FSRVKKSVEV LKNNKCPYFS CEQPCNQTTA GNALTFLKSL LEIFQKEKMR

GMRGKI

-continued

IL-2Rβ ECD

SEQ ID NO: 11

AVNGTSQFTC FYNSRANISC VWSQDGALQD TSCQVHAWPD RRRWNQTCEL LPVSQASWAC

NLILGAPDSQ KLTTVDIVTL RVLCREGVRW RVMAIQDFKP FENLRLMAPI SLQVVHVETH

RCNISWEISQ ASHYFERHLE FEARTLSPGH TWEEAPLLTL KQKQEWICLE TLTPDTQYEF

QVRVKPLQGE FTTWSPWSQP LAFRTKPAAL GKDT

IL-21Rα ECD (source: uniprot.org/uniprot/Q9HBE5)

SEQ ID NO: 12

CPDLVCYTDY LQTVICILEM WNLHPSTLTL TWQDQYEELK DEATSCSLHR SAHNATHATY

TCHMDVFHFM ADDIFSVNIT DQSGNYSQEC GSFLLAESIK PAPPFNVTVT FSGQYNISWR

SDYEDPAFYM LKGKLQYELQ YRNRGDPWAV SPRRKLISVD SRSVSLLPLE FRKDSSYELQ

VRAGPMPGSS YQGTWSEWSD PVIFQTQSEE LKE

Human IL-21Rγ ECD

SEQ ID NO: 13

LNTTILTPNG NEDTTADFFL TTMPTDSLSV STLPLPEVQC FVFNVEYMNC TWNSSSEPQP

TNLTLHYWYK NSDNDKVQKC SHYLFSEEIT SGCQLQKKEI HLYQTFVVQL QDPREPRRQA

TQMLKLQNLV IPWAPENLTL HKLSESQLEL NWNNRFLNHC LEHLVQYRTD WDHSWTEQSV

DYRHKFSLPS VDGQKRYTFR VRSRFNPLCG SAQHWSEWSH PIHWGSNTSK ENPFLFALEA

IL-7α receptor ECD (Source: https://www.uniprot.org/uniprot/P16871)

SEQ ID NO: 14

ESGYAQNGDL EDAELDDYSF SCYSQLEVNG SQHSLTCAFE DPDVNITNLE FEICGALVEV

KCLNFRKLQE IYFIETKKFL LIGKSNICVK VGEKSLTCKK IDLTTIVKPE APFDLSWYR

EGANDFVVTF NTSHLQKKYV KVLMHDVAYR QEKDENKWTH VNLSSTKLTL LQRKLQPAAM

YEIKVRSIPD HYFKGFWSEW SPSYYFRTPE INNSSGEMD

IL-9α receptor ECD (source:)

SEQ ID NO: 15

SVTGEGQGPR SRTFTCLTNN ILRIDCHWSA PELGQGSSPW LLFTSNQAPG GTHKCILRGS

ECTVVLPPEA VLVPSDNFTI TFHHCMSGRE QVSLVDPEYL PRRHVKLDPP SDLQSNISSG

HCILTWSISP ALEPMTTLLS YELAFKKQEE AWEQAQHRDH IVGVTWLILE AFELDPGFIH

EARLRVQMAT LEDDVVEEER YTGQWSEWSQ PVCFQAPQRQ GPLIPPWGWP

Fc-scFv2 against IL-15

SEQ ID NO: 16

DKTHTCPPCP APEAAGGPSV FLFPPKPKDT LYITREPEVT CVVVDVSHED PEVKFNWYVD

GVEVHNAKTK PREEQYNSTY RVVSVLTVLH QDWLNGKEYK CKVSNKALPA PIEKTISKAK

GQPREPQVCT LPPSREEMTK NQVSLSCAVK GFYPSDIAVE WESNGQPENN YKTTPPVLDS

DGSFFLVSKL TVDKSRWQQG NVFSCSVMHE ALHNHYTQKS LSLSPGAGGG GSVHMPLGFL

GPRQARVVNG GGGGSGGGGS EIVLTQSPGT LSLSPGERAT LSCRASQSVS SSYLAWYQQK

PGQAPRLLIY GASRRATGIP DRFSGSGSGT DFTLTISRLE PEDFAVYYCQ RYGSSHTFGQ

GTKLEISGGG GSGGGGSGGG GSEVQLVQSG AEVKKPGESL KISCKVSGYF FTTYWIGWVR

QMPGKGLEYM GIIYPGDSDT RYSPSFQGQV TISADKSIST AYLQWSSLKA SDTAMYYCAR

GGNWNCFDYW GQGTLVTVSS

Fc-IL-15 N65D

SEQ ID NO: 17

DKTHTCPPCP APEAAGGPSV FLFPPKPKDT LYITREPEVT CVVVDVSHED PEVKFNWYVD

GVEVHNAKTK PREEQYNSTY RVVSVLTVLH QDWLNGKEYK CKVSNKALPA PIEKTISKAK

GQPREPQVYT LPPCREEMTK NQVSLWCLVK GFYPSDIAVE WESNGQPENN YKTTPPVLDS

DGSFFLYSKL TVDKSRWQQG NVFSCSVMHE ALHNHYTQKS LSLSPGAGGG GSGGGGSGGG

GSITCPPPMS VEHADIWVKS YSLYSRERYI CNSGFKRKAG TSSLTECVLN KATNVAHWTT

PSLKCIRGGG GSGGGSGGGG SAAGGGGSGG GGSGGGGSNW VNVISDLKKI EDLIQSMHID

ATLYTESDVH PSCKVTAMKC FLLELQVISL ESGDASIHDT VEDLIILANN SLSSNGNVTE

SGCKECEELE EKNIKEFLQS FVHIVQMFIN TS

Anti-IL-15 scFv1 (italic: VH and VL)

SEQ ID NO: 18

*EVQLVQSGAE VKKPGESLKI SCKVSGYFFT TYWIGWVRQM PGKGLEYMGI IYPGDSDTRY*

*SPSFQGQVTI SADKSISTAY LQWSSLKASD TAMYYCARGG NWNCFDYWGQ GTLVTVSSGG*

*GGSGGGGSGG GGSGIVLTQS PGTLSLSPGE RATLSCRASQ SVSSSYLAWY QQKPGQAPRL*

*LIYGASRRAT GIPDRFSGSG SGTDFTLTIS RLEPEDFAVY YCQRYGSSHT FGQGTKLEIS*

Anti-IL-15 scFv2 (italic: VL and VH)

SEQ ID NO: 19

*EIVLTQSPGT LSLSPGERAT LSCRASQSVS SSYLAWYQQK PGQAPRLLIY GASRRATGIP*

*DRFSGSGSGT DFTLTISRLE PEDFAVYYCQ RYGSSHTFGQ GTKLEISGGG GSGGGGSGGG*

*GSEVQLVQSG AEVKKPGESL KISCKVSGYF FTTYWIGWVR QMPGKGLEYM GIIYPGDSDT*

*RYSPSFQGQV TISADKSIST AYLQWSSLKA SDTAMYYCAR GGNWNCFDYW GQGTLVTVSS*

Anti-IL-21 scFv1 (italic: VH and VL)

SEQ ID NO: 20

*QVQLVESGGG WQPGRSLRL SCAASGFTFS SYGMHWVRQA PGKGLEWVAF IWYDGSDKYY*

*ADSVKGRFTI SRDNSKNTLY LQMNSLRAED TAVYYCARDG DSSDWYGDYY FGMDVWGQGT*

*TVTVSSGGGG SGGGGSGGGG SEIVLTQSPG TLSLSPGERA TLSCRASQSV SSSYLAWYQQ*

*KPGQAPRLLI YGASSRATGI PDRFSGSGSG TDFTLTISRL EPEDFAVYYC QQYGSWTFGQ*

*GTKVEIK*

Anti-IL-21 scFv2 (italic: VL and VH)

SEQ ID NO: 21

*EIVLTQSPGT LSLSPGERAT LSCRASQSVS SSYLAWYQQK PGQAPRLLIY GASSRATGIP*

*DRFSGSGSGT DFTLTISRLE PEDFAVYYCQ QYGSWTFGQG TKVEIKGGGG SGGGGSGGGG*

*SQVQLVESGG GVVQPGRSLR LSCAASGFTF SSYGMHWVRQ APGKGLEWVA FIWYDGSDKY*

*YADSVKGRFT ISRDNSKNTL YLQMNSLRAE DTAVYYCARD GDSSDWYGDY YFGMDVWGQG*

*TTVTVSS*

Anti-IL-2 scFv1 (underlined: HCDR1-3 and LCDR1-3;
italic: VH and VL)

SEQ ID NO: 22

*QVQLVQSGAE VKKPGSSVKV SCKASG<u>GTFS SYAIS</u>WVRQA PGQGLEWMGG <u>IIPIFGTANY</u>*

*AQKFQGRVTI TADESTSTAY MELSSLRSED TAVYYCAR<u>VD RYYNWNYFLG SFDY</u>WGQGTL*

*VTVSSGGGGS GGGGSGGGGS SYVLTQPPSV SVAPGKTARI TC<u>GGNNIRSK SVHW</u>YQQKPG*

*QAPVVVIY<u>YD SDRPS</u>GIPER ISGSNSGNTA TLTISRVEAG DEADYFC<u>QVW DSSSDHHV</u>FG*

*GGTKLTVL*

Anti-IL-2 scFv2 (underlined: LCDR1-3 and HCDR1-3;
italic: VL and VH)

SEQ ID NO: 23

*SYVLTQPPSV SVAPGKTARI TC<u>GGNNIRSK SVHW</u>YQQKPG QAPWVIYY<u>D SDRPS</u>GIPER*

*ISGSNSGNTA TLTISRVEAG DEADYFC<u>QVW DSSSDHHV</u>FG GGTKLTVLGG GGSGGGGSGGG*

*GSQVQLVQSG AEVKKPGSSV KVSCKASG<u>GT FSSYA</u>ISWVR QAPGQGLEWM GG<u>IIPIFGTA</u>*

*<u>NYA</u>QKFQGRV TITADESTST AYMELSSLRS EDTAVYYCAR <u>VDRYYNWNYF LGSFDY</u>WGQG*

*TLVTVSS*

-continued

PD1-HC-IL-2V (CX3.58.1)

SEQ ID NO: 24

QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPCQEE MTKNQVSLWC

LVKGFYPSDI AVEWESNGQP ENNYKTTPPV LDSDGSFFLY SRLTVDKSRW QEGNVFSCSV

MHEALHNHYT QKSLSLSLGK GGGGSGGGGS GGGGSAPASS STKKTQLQLE HLLLDLQMIL

NGINNYKNPK LTSMLTAKFA MPKKATELKH LQCLEEALKP LEEVLNLAQS KNFHLRPRDL

ISNINVIVLE LKGSETTFMC EYADETATIV EFLNRWITFS QSIISTLT

PD1-HC-IL-2Rβ-ECD (CX3.58.1)

SEQ ID NO: 25

QVQLVESGGG VVQPGRSLRL DCKASGITFS NSGMHWVRQA PGKGLEWVAV VSSASTKGPS

ADSVKGRFTI SRDNSKNTLF LQMNSLRAED TAVYYCATND DYWGQGTLVT QSSGLYSLSS

VFPLAPCSRS TSESTAALGC LVKDYFPEPV TVSWNSGALT SGVHTFPAVL PSVFLFPPKP

VVTVPSSSLG TKTYTCNVDH KPSNTKVDKR VESKYGPPCP PCPAPEFLGG STYRVVSVLT

KDTLMISRTP EVTCVVVDVS QEDPEVQFNW YVDGVEVHNA KTKPREEQFN MTKNQVSLSC

VLHQDWLNGK EYKCKVSNKG LPSSIEKTIS KAKGQPREPQ VCTLPPSQEE QEGNVFSCSV

AVKGFYPSDI AVEWESNGQP ENNYKTTPPV LDSDGSFFLV SRLTVDKSRW CFYNSRANIS

MHEALHNHYT QKSLSLSLGK GGGGSGPLGV RGGGGSGGGG SAVNGTSQFT QKLTTVDIVT

CVWSQDGALQ DTSCQVHAWP DRRRWNQTCE LLPVSQASWA CNLILGAPDS QASHYFERHL

LRVLCREGVR WRVMAIQDFK PFENLRLMAP ISLQVVHVET HRCNISWEIS EFTTWSPWSQ

EFEARTLSPG HTWEEAPLLT LKQKQEWICL ETLTPDTQYE FQVRVKPLQG

PLAFRTKPAA LGKDT

PD1-HC-IL-21Rα ECD WITH NON-CLEAVABLI : PEPTIDE LINKER

SEQ ID NO: 26

MGVKVLFALI CIAVAEAQVQ LVESGGGVVQ PGRSLRLDCK ASGITFSNSG MHWVRQAPGK

GLEWVAVIWY DGSKRYYADS VKGRFTISRD NSKNTLFLQM NSLRAEDTAV YYCATNDDYW

GQGTLVTVSS ASTKGPSVFP LAPCSRSTSE STAALGCLVK DYFPEPVTVS WNSGALTSGV

HTFPAVLQSS GLYSLSSVVT VPSSSLGTKT YTCNVDHKPS NTKVDKRVES KYGPPCPPCP

APEFLGGPSV FLFPPKPKDT LMISRTPEVT CVVVDVSQED PEVQFNWYVD GVEVHNAKTK

PREEQFNSTY RVVSVLTVLH QDWLNGKEYK CKVSNKGLPS SIEKTISKAK GQPREPQVYT

LPPSQEEMTK NQVSLTCLVK GFYPSDIAVE WESNGQPENN YKTTPPVLDS DGSFFLYSRL

TVDKSRWQEG NVFSCSVMHE ALHNHYTQKS LSLSLGAGGG GSGGGGGSAAG GGGSGGGGSC

PDLVCYTDYL QTVICILEMW NLHPSTLTLT WQDQYEELKD EATSCSLHRS AHNATHATYT

CHMDVFHFMA DDIFSVNITD QSGNYSQECG SFLLAESIKP APPFNVTVTF SGQYNISWRS

DYEDPAFYML KGKLQYELQY RNRGDPWAVS PRRKLISVDS RSVSLLPLEF RKDSSYELQV

RAGPMPGSSY QGTWSEWSDP VIFQTQSEEL KE

-continued

SEQ ID NO: 27-34 Peptide Linker (SEQ ID NO: 27)

(GGGGS)_n,
wherein n = 1, 2, 3, and 4

(SEQ ID NO: 28)

GGGGS (SEQ ID NO: 29)

GGGGSGGGGS (SEQ ID NO: 30)

GGGGSGGGGSGGGGS (SEQ ID NO: 31)

GGGGSGGGGSXXGGGGSGGGGS,
X = A or N (SEQ ID NO: 32)

GGGGSGGGGSGGGGSXXGGGGSGGGGS,
X = A or N (SEQ ID NO : 33)

GGGGSGGGGSGGGGSXXGGGGSGGGGSGGGGS,
X = A or N (SEQ ID NO: 34)

GGGGSGGGGXGGGGYGGGGS,
X = S, A or N, and Y = A or N

PD1-HC-IL-2V

SEQ ID NO: 35

QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLA (GGGGS)_{n1}X_1X_2(GGGGS)_{n2}APX_{aa3}SSSTKKTQL QLEHLLLDLQ

MILNGINNYK NPX_{aa35}LTRMLTX_{aa42}KFX_{aa45}M PKKATELKH LQCLEEELKP

LEEVLNX_{aa72}X_{aa73}QSKNFHLR PRDLISNINV IVLELKGSET TFMCEYADET ATIVEFLNRW

ITFX_{aa125}QSIIS TLT
wherein X_{aa3} is N or A;
wherein X_{aa125} is A or S;
wherein X_{aa35} is selected from K and N;
wherein X_{aa42} is selected from A, G, S, T, Q, E, N, D, R, and K;
wherein X_{aa45} is selected from A, G, S, T, Q, E, N, D, R, and K;
wherein X_{aa72} is selected from A, G, S, T, Q, E, N, D, R, and K;
wherein X_{aa73} is selected from A and T;
wherein n_1 = 0, 1, 2, or 3;
n_2 = 0, 1, 2, or 3;
and
X_1 is an amino acid Alanine or deleted; and
X_2 is an amino acid Alanine or deleted.

PD1-HC-IL-2Rβ-ECD

SEQ ID NO: 36

QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

-continued

```
MHEALHNHYT QKSLSLSLGA(GGGGS)n1X1X2(GGGGS)n2AV NGTSQFTCFY NSRANISCVW

SQDGALQDTS CQVHAWPDRR RWNQTCELLP VSQASWACNL ILGAPDSQKL TTVDIVTLRV

LCREGVRWRV MAIQDFKPFE NLRLMAPISL QVVHVETHRC NISWEISQAS HYFERHLEFE

ARTLSPGHTW EEAPLLTLKQ KQEWICLETL TPDTQYEFQV RVKPLQGEFT TWSPWSQPLA

FRTKPAALGK DT
```
Wherein $n_1$ = 0, 1, 2, or 3; $n_2$ = 0, 1, 2, or 3; $X_1$ is an amino acid
Alanine or deleted; and $X_2$ is an amino acid Alanine or deleted.

PD1-HC with-SUSHI-IL-15V

SEQ ID NO: 37
```
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLGA GGGGSGGGGS GGGGSITCPP PMSVEHADIW VKSYSLYSRE

RYICNSGFKR KAGTSSLTEC VLNKATNVAH WTTPSLKCIR GGGGSGGGSG GGGSAAGGGG

SGGGGSGGGG SNWVNVISDL KKIEDLIQSM HIDATLYTES DVHPSCKVTA MKCFLLELQV

ISLESGDASI HDTVEDLIIL ANNSLSSNGN VTESGCKECE ELEEKNIKEF LQSFVHIVQM

PINTS
```

PD1-HC-SCFV2 AGAINST IL-15

SEQ ID NO: 38
```
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLGA(GGGGS)n1X1X2(GGGGS)n2EIVLTQSPGTLS LSPGERATLS

CRASQSVSSS YLAWYQQKPG QAPRLLIYGA SRRATGIPDR FSGSGSGTDF TLTISRLEPE

DFAVYYCQRY GSSHTFGQGT KLEISGGGGS GGGGSGGGGS EVQLVQSGAE VKKPGESLKI

SCKVSGYFFT TYWIGWVRQM PGKGLEYMGI IYPGDSDTRY SPSFQGQVTI SADKSISTAY

LQWSSLKASD TAMYYCARGG NWNCFDYWGQ GTLVTVSS
```
Wherein $n_1$ = 0, 1, 2, or 3; $n_2$ = 0, 1, 2, or 3; $X_1$ is an amino acid
Alanine or deleted; and $X_2$ is an amino acid Alanine or deleted.

PD1-HC-IL-21

SEQ ID NO: 39
```
MGVKVLFALI CIAVAEAQVQ LVESGGGVVQ PGRSLRLDCK ASGITFSNSG MHWVRQAPGK

GLEWVAVIWY DGSKRYYADS VKGRFTISRD NSKNTLFLQM NSLRAEDTAV YYCATNDDYW

GQGTLVTVSS ASTKGPSVFP LAPCSRSTSE STAALGCLVK DYFPEPVTVS WNSGALTSGV

HTFPAVLQSS GLYSLSSVVT VPSSSLGTKT YTCNVDHKPS NTKVDKRVES KYGPPCPPCP

APEFLGGPSV FLFPPKPKDT LMISRTPEVT CVVVDVSQED PEVQFNWYVD GVEVHNAKTK

PREEQFNSTY RVVSVLTVLH QDWLNGKEYK CKVSNKGLPS SIEKTISKAK GQPREPQVYT
```

-continued

```
LPPSQEEMTK NQVSLTCLVK GFYPSDIAVE WESNGQPENN YKTTPPVLDS DGSFFLYSRL

TVDKSRWQEG NVFSCSVMHE ALHNHYTQKS LSLSLGAGGG GSGGGGSGGG GSQGQDRHMI

RMRQLIDIVD QLKNYVNDLV PEFLPAPEDV ETNCEWSAFS CFQKAQLKSA NTGNNERIIN

VSIKKLKRKP PSTNAGRRQK HRLTCPSCDS YEKKPPKEFL ERFKSLLQKM IHQHLSSRTH

GSEDS
```

PD1-HC-IL-21Rα ECD WITH CLEAVABLE PEPTIDE LINKER

SEQ ID NO: 40

```
MGVKVLFALK CIAVAEAQVQ LVESGGGVVQ PGRSLRLDCK ASGITFSNSG MHWVRQAPGK

QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLGA GGGGSGGGGS GPLGVRGGGG SCPDLVCYTD YLQTVICILE

MWNLHPSTLT LTWQDQYEEL KDEATSCSLH RSAHNATHAT YTCHMDVFHF MADDIFSVNI

TDQSGNYSQE CGSFLLAESI KPAPPFNVTV TFSGQYNISW RSDYEDPAFY MLKGKLQYEL

QYRNRGDPWA VSPRRKLISV DSRSVSLLPL EFRKDSSYEL QVRAGPMPGS SYQGTWSEWS

DPVIFQTQSE ELKE
```

PD1-HC-SCFV2 AGAINST IL-21

SEQ ID NO: 41

```
MGVKVLFALI CIAVAEAQVQ LVESGGGVV QPGRSLRLDC KASGITFSNS GMHWVRQAPG

KGLEWVAVIW YDGSKRYYAD SVKGRFTIS RDNSKNTLFL QMNSLRAEDT AVYYCATNDD

YWGQGTLVTV SSASTKGPSV FPLAPCSRS TSESTAALGC LVKDYFPEPV TVSWNSGALT

SGVHTFPAVL QSSGLYSLSS VVTVPSSSL GTKTYTCNVD HKPSNTKVDK RVESKYGPPC

PPCPAPEFLG GPSVFLFPPK PKDTLMISR TPEVTCVVVD VSQEDPEVQF NWYVDGVEVH

NAKTKPREEQ FNSTYRVVSV LTVLHQDWL NGKEYKCKVS NKGLPSSIEK TISKAKGQPR

EPQVYTLPPS QEEMTKNQVS LTCLVKGFY PSDIAVEWES NGQPENNYKT TPPVLDSDGS

FFLYSRLTVD KSRWQEGNVF SCSVMHEAL HNHYTQKSLS LSLGAGGGGS GGGGSAAGGG

GSGGGGGSEIV LTQSPGTLSL SPGERATLS CRASQSVSSS YLAWYQQKPG QAPRLLIYGA

SSRATGIPDR FSGSGSGTDF TLTISRLEP EDFAVYYCQQ YGSWTFGQGT KVEIKGGGGS

GGGGSGGGGS QVQLVESGGG VVQPGRSLR LSCAASGFTF SSYGMHWVRQ APGKGLEWVA

FIWYDGSDKY YADSVKGRFT ISRDNSKNT LYLQMNSLRA EDTAVYYCAR DGDSSDWYGD

YYFGMDVWGQ GTTVTVSS
```

PD1-HC with knob mutations-IL-21

SEQ ID NO: 42

```
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPCQEE MTKNQVSLWC

LVKGFYPSDI AVEWESNGQP ENNYKTTPPV LDSDGSFFLY SRLTVDKSRW QEGNVFSCSV
```

-continued

```
MHEALHNHYT QKSLSLSLGA GGGGSGGGGS GGGGSQGQDR HMIRMRQLID IVDQLKNYVN

DLVPEFLPAP EDVETNCEWS AFSCFQKAQL KSANTGNNER IINVSIKKLK RKPPSTNAGR

RQKHRLTCPS CDSYEKKPPK EFLERFKSLL QKMIHQHLSS RTHGSEDS
```

PD1-HC with hole mutations-IL-21Rα ECD

SEQ ID NO: 43

```
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VCTLPPSQEE MTKNQVSLSC

AVKGFYPSDI AVEWESNGQP ENNYKTTPPV LDSDGSFFLV SRLTVDKSRW QEGNVFSCSV

MHEALHNHYT QKSLSLSLGA GGGGSGGGGS AAGGGGSGGG GSCPDLVCYT DYLQTVICIL

EMWNLHPSTL TLTWQDQYEE LKDEATSCSL HRSAHNATHA TYTCHMDVFH FMADDIFSVN

ITDQSGNYSQ ECGSFLLAES IKPAPPFNVT VTFSGQYNIS WRSDYEDPAF YMLKGKLQYE

LQYRNRGDPW AVSPRRKLIS VDSRSVSLLP LEFRKDSSYE LQVRAGPMPG SSYQGTWSEW

SDPVIFQTQS EELKE
```

PD1-LC

SEQ ID NO: 44

```
EIVLTQSPAT LSLSPGERAT LSCRASQSVS SYLAWYQQKP GQAPRLLIYD ASNRATGIPA

RFSGSGSGTD FTLTISSLEP EDFAVYYCQQ SSNWPRTFGQ GTKVEIKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGEC
```

Anti-PDL1 atezolizumab LC

SEQ ID NO: 45

```
DIQMTQSPSS LSASVGDRVT ITCRASQDVS TAVAWYQQKP GKAPKLLIYS ASFLYSGVPS

RFSGSGSGTD FTLTISSLQP EDFATYYCQQ YLYHPATFGQ GTKVEIKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGEC
```

Anti-PDL1 atezolizumab HC

SEQ ID NO: 46

```
EVQLVESGGG LVQPGGSLRL SCAASGFTFS DSWIHWVRQA PGKGLEWVAW ISPYGGSTYY

ADSVKGRFTI SADTSKNTAY LQMNSLRAED TAVYYCARRH WPGGFDYWGQ GTLVTVSSAS

TKGPSVFPLA PSSKSTSGGT AALGCLVKDY FPEPVTVSWN SGALTSGVHT FPAVLQSSGL

YSLSSVVTVP SSSLGTQTYI CNVNHKPSNT KVDKKVEPKS CDKTHTCPPC PAPELLGGPS

VFLFPPKPKD TLMISRTPEV TCVVVDVSHE DPEVKFNWYV DGVEVHNAKT KPREEQYAST

YRVVSVLTVL HQDWLNGKEY KCKVSNKALP APIEKTISKA KGQPREPQVY TLPPSREEMT

KNQVSLTCLV KGFYPSDIAV EWESNGQPEN NYKTTPPVLD SDGSFFLYSK

GNVFSCSVMH EALHNHYTQK SLSLSPGK
```

Anti-PD-1 Nivolumab HC

SEQ ID NO: 47

```
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP
```

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLGK

Anti-PD-1 Pembrolizumab LC

SEQ ID NO: 48

EIVLTQSPAT LSLSPGERAT LSCRASKGVS TSGYSYLHWY TFGGGTKVEI KRTVAAPSVF

GVPARFSGSG SGTDFTLTIS SLEPEDFAVY YCQHSRDLPL GNSQESVTEQ DSKDSTYSLS

IFPPSDEQLK SGTASVVCLL NNFYPREAKV QWKVDNALQS GNSQESVTEQ DSKDSTYSLS

STLTLSKADY EKHKVYACEV THQGLSSPVT KSFNRGEC

Anti-PD-1 Pembrolizumab HC

SEQ ID NO: 49

QVQLVQSGVE VKKPGASVKV SCKASGYTFT NYYMYWVRQA PGQGLEWMGG INPSNGGTNF

QVQLVQSGVE VKKPGASVKV SCKASGYTFT NYYMYWVRQA YRFDMGFDYW GQGTTVTVSS

NEKFKNRVTL TTDSSTTTAY MELKSLQFDD TAVYYCARRD WNSGALTSGV HTFPAVLQSS

ASTKGPSVFP LAPCSRSTSE STAALGCLVK DYFPEPVTVS KYGPPCPPCP APEFLGGPSV

GLYSLSSVVT VPSSSLGTKT YTCNVDHKPS NTKVDKRVES GVEVHNAKTK PREEQFNSTY

FLFPPKPKDT LMISRTPEVT CVVVDVSQED PEVQFNWYVD GQPREPQVYT LPPSQEEMTK

RVVSVLTVLH QDWLNGKEYK CKVSNKGLPS SIEKTISKAK DGSFFLYSRL TVDKSRWQEG

NQVSLTCLVK GFYPSDIAVE WESNGQPENN YKTTPPVLDS DGSFFLYSRL TVDKSRWQEG

NVFSCSVMHE ALHNHYTQKS LSLSLGK

SEQ ID NO: 50

EIVLTQSPGT LSLSPGERAT LSCRASQSVG SSYLAWYQQK PGQAPRLLIY GAFSRATGIP

DRFSGSGSGT DFTLTISRLE PEDFAVYYCQ QYGSSPWTFG QGTKVEIKRT VAAPSVFIFP

PSDEQLKSGT ASVVCLLNNF YPREAKVQWK VDNALQSGNS QESVTEQDSK DSTYSLSSTL

TLSKADYEKH KVYACEVTHQ GLSSPVTKSF NRGEC

CTLA-4 antibody Ipilimumab HC-IL2v

SEQ ID NO: 51

QVQLVESGGG VVQPGRSLRL SCAASGFTFS SYTMHWVRQA PGKGLEWVTF ISYDGNNKYY

ADSVKGRFTI SRDNSKNTLY LQMNSLRAED TAIYYCARTG WLGPFDYWGQ GTLVTVSSAS

TKGPSVFPLA PSSKSTSGGT AALGCLVKDY FPEPVTVSWN SGALTSGVHT FPAVLQSSGL

YSLSSVVTVP SSSLGTQTYI CNVNHKPSNT KVDKRVEPKS CDKTHTCPPC PAPELLGGPS

VFLFPPKPKD TLMISRTPEV TCVVVDVSHE DPEVKFNWYV DGVEVHNAKT KPREEQYNST

YRVVSVLTVL HQDWLNGKEY KCKVSNKALP APIEKTISKA KGQPREPQVY TLPPSRDELT

KNQVSLTCLV KGFYPSDIAV EWESNGQPEN NYKTTPPVLD SDGSFFLYSK LTVDKSRWQQ

GNVFSCSVMH EALHNHYTQK SLSLSPGA(GGGGS)$_{n1}$X$_1$X$_2$(GGGGS)$_{n2}$APX$_{aa3}$ SSSTKKTQLQ

LEHLLLDLQM ILNGINNYKN PX$_{aa35}$LTRMLTX$_{aa42}$KFX$_{aa45}$M PKKATELKHLQ CLEEELKPLE

EVLNX$_{aa72}$X$_{aa73}$QSKNFHLRPR DLISNINVIV LELKGSETTF MCEYADETATI VEFLNRWITF

X$_{aa125}$QSIIST LT
wherein X$_{aa3}$ is N or A;
wherein X$_{aa125}$ is A or S;
wherein X$_{aa35}$ is selected from K and N;
wherein X$_{aa42}$ is selected from A, G, S, T, Q, E, N, D, R, and K;
wherein X$_{aa45}$ is selected from A, G, S, T, Q, E, N, D, R, and K;
wherein X$_{aa72}$ is selected from A, G, S, T, Q, E, N, D, R, and K;
wherein X$_{aa73}$ is selected from A and T;
wherein n$_1$ = 0, 1, 2, or 3;
n$_2$ = 0, 1, 2, or 3; and
X$_1$ is an amino acid Alanine or deleted; and
X$_2$ is an amino acid Alanine or deleted.

-continued

CTLA-4 antibody Ipilimumab HC-IL15v

SEQ ID NO: 52

QVQLVESGGG VVQPGRSLRL SCAASGFTFS SYTMHWVRQA PGKGLEWVTF ISYDGNNKYY

ADSVKGRFTI SRDNSKNTLY LQMNSLRAED TAIYYCARTG WLGPFDYWGQ GTLVTVSSAS

TKGPSVFPLA PSSKSTSGGT AALGCLVKDY FPEPVTVSWN SGALTSGVHT FPAVLQSSGL

YSLSSVVTVP SSSLGTQTYI CNVNHKPSNT KVDKRVEPKS CDKTHTCPPC PAPELLGGPS

VFLFPPKPKD TLMISRTPEV TCVVVDVSHE DPEVKFNWYV DGVEVHNAKT KPREEQYNST

YRVVSVLTVL HQDWLNGKEY KCKVSNKALP APIEKTISKA KGQPREPQVY TLPPSRDELT

KNQVSLTCLV KGFYPSDIAV EWESNGQPEN NYKTTPPVLD SDGSFFLYSK LTVDKSRWQQ

GNVFSCSVMH EALHNHYTQK SLSLSPGAGG GGSGGGGSGG GGSITCPPPM SVEHADIWVK

SYSLYSRERY ICNSGFKRKA GTSSLTECVL NKATNVAHWT TPSLKCIRGG GGSGGGGSGG

GSAAGGGGSG GGGSGGGGSN WVNVISDLKK IEDLIQSMHI DATLYTESDV HPSCKVTAMK

CFLLELQVIS LESGDASIHD TVEDLIILAN NSLSSNGNVT ESGCKECEEL EEKNIKEFLQ

SFVHIVQMFI NTS

CTLA-4 antibody Ipilimumab HC- IL-21

SEQ ID NO: 53

QVQLVESGGG VVQPGRSLR LSCAASGFTF SSYTMHWVRQ APGKGLEWVT FISYDGNNKYY

ADSVKGRFTI SRDNSKNTL YLQMNSLRAE DTAIYYCART GWLGPFDYWG QGTLVTVSSAS

TKGPSVFPLA PSSKSTSGG TAALGCLVKD YFPEPVTVSW NSGALTSGVH TFPAVLQSSGL

YSLSSVVTVP SSSLGTQTY ICNVNHKPSN TKVDKRVEPK SCDKTHTCPP CPAPELLGGPS

VFLFPPKPKD TLMISRTPE VTCVVVDVSH EDPEVKFNWY VDGVEVHNAK TKPREEQYNST

YRVVSVLTVL HQDWLNGKE YKCKVSNKAL PAPIEKTISK AKGQPREPQV YTLPPSRDELT

KNQVSLTCLV KGFYPSDIA VEWESNGQPE NNYKTTPPVL DSDGSFFLYS KLTVDKSRWQQ

GNVFSCSVMH EALHNHYTQ KSLSLSPGA (GGGGS)$_{n1}$X$_1$X$_2$(GGGGS)$_{n2}$QGQDRHMIRM RQLI

DIVDQLKNYV NDLVPEFLP APEDVETNCE WSAFSCFQKA QLKSANTGNN ERIINVSIKKL

KRKPPSTNAG RRQKHRLTC PSCDSYEKKP PKEFLERFKS LLQKMIHQHL SSRTHGSEDS
Wherein n$_1$ = 0, 1, 2, or 3; n$_2$ = 0, 1, 2, or 3; X$_1$ is an amino acid
Alanine or deleted; and X$_2$ is an amino acid Alanine or deleted.

CTLA-4 antibody Ipilimumab HC-IL-2Rβ-ECD

SEQ ID NO: 54

QVQLVESGGG VVQPGRSLRL SCAASGFTFS SYTMHWVRQA PGKGLEWVTF ISYDGNNKYY

ADSVKGRFTI SRDNSKNTLY LQMNSLRAED TAIYYCARTG WLGPFDYWGQ GTLVTVSSAS

TKGPSVFPLA PSSKSTSGGT AALGCLVKDY FPEPVTVSWN SGALTSGVHT FPAVLQSSGL

YSLSSVVTVP SSSLGTQTYI CNVNHKPSNT KVDKRVEPKS CDKTHTCPPC PAPELLGGPS

VFLFPPKPKD TLMISRTPEV TCVVVDVSHE DPEVKFNWYV DGVEVHNAKT KPREEQYNST

YRVVSVLTVL HQDWLNGKEY KCKVSNKALP APIEKTISKA KGQPREPQVY TLPPSRDELT

KNQVSLTCLV KGFYPSDIAV EWESNGQPEN NYKTTPPVLD SDGSFFLYSK LTVDKSRWQQ

GNVFSCSVMH EALHNHYTQK SLSLS PGA (GGGGS)$_{n1}$X$_1$X$_2$(GGGGS)$_{n2}$ AVNG TSQFTCFYNS

RANISCVWSQ DGALQDTSCQ VHAWPDRRRW NQTCELLPVS QASWACNLIL GAPDSQKLTT

VDIVTLRVLC REGVRWRVMA IQDFKPFENL RLMAPISLQV VHVETHRCNI SWEISQASHY

FERHLEFEAR TLSPGHTWEE APLLTLKQKQ EWICLETLTP DTQYEFQVRV KPLQGEFTTW

SPWSQPLAFR TKPAALGKDT
Wherein n$_1$ = 0, 1, 2, or 3; n$_2$ = 0, 1, 2, or 3;
X$_1$ is an amino acid Alanine or deleted;
and X$_2$ is an amino acid Alanine or deleted.

-continued

CTLA-4 antibody Ipilimumab HC-scFv1 against IL-2 (in
the scFV, underlined: HCDR1-3 and LCDR1-3; italic: VH and VL)
SEQ ID NO: 55
QVQLVESGGG VVQPGRSLRL SCAASGFTFS SYTMHWVRQA PGKGLEWVTF ISYDGNNKYY

ADSVKGRFTI SRDNSKNTLY LQMNSLRAED TAIYYCARTG WLGPFDYWGQ GTLVTVSSAS

TKGPSVFPLA PSSKSTSGGT AALGCLVKDY FPEPVTVSWN SGALTSGVHT FPAVLQSSGL

YSLSSVVTVP SSSLGTQTYI CNVNHKPSNT KVDKRVEPKS CDKTHTCPPC PAPELLGGPS

VFLFPPKPKD TLMISRTPEV TCVVVDVSHE DPEVKFNWYV DGVEVHNAKT KPREEQYNST

YRVVSVLTVL HQDWLNGKEY KCKVSNKALP APIEKTISKA KGQPREPQVY TLPPSRDELT

KNQVSLTCLV KGFYPSDIAV EWESNGQPEN NYKTTPPVLD SDGSFFLYSK LTVDKSRWQQ

GNVFSCSVMH EALHNHYTQK SLSLSPGA(GGGGS)$_{n1}$X$_1$X$_2$(GGGGS)$_{n2}$QVQ LVQSGAEVEE

*PGSSVKVSCK ASG*GTFSSYA *ISWVRQAPGQ GLEWMGG*IIP IFGTANYAQK *LVQSGAEVKK*

*ESTSSAYMEL SSLRSEDTAV YYCAR*VDRYY NWNYFLGSFD *YWGQGTLVTV SSGGGGSGGG*

*GSGGGGSSYV LTQPPSVSVA PGKTARITCG* GNNIRSKSVH *WYQQKPGQAP VVVIY*YDSDR

*PSGIPERISG SBSGNTATLITSRVEAGDEADYFCQVWDSSSDHHVFGGGTKLTVL;*
Wherein n$_1$ = 0, 1, 2, or 3; n$_2$ = 0, 1, 2, or 3; X$_1$ is an amino acid
Alanine or deleted; and X$_2$ is an amino acid Alanine or deleted.

CTLA-4 antibody Ipilimumab HC- scFv2 against IL-2
(underlined: LCDR1-3 and HCDR1-3; italic: VL and VH)
SEQ ID NO: 56
QVQLVESGGG VVQPGRSLRL SCAASGFTFS SYTMHWVRQA PGKGLEWVTF ISYDGNNKYY

ADSVKGRFTI SRDNSKNTLY LQMNSLRAED TAIYYCARTG WLGPFDYWGQ GTLVTVSSAS

TKGPSVFPLA PSSKSTSGGT AALGCLVKDY FPEPVTVSWN SGALTSGVHT FPAVLQSSGL

YSLSSVVTVP SSSLGTQTYI CNVNHKPSNT KVDKRVEPKS CDKTHTCPPC PAPELLGGPS

VFLFPPKPKD TLMISRTPEV TCVVVDVSHE DPEVKFNWYV DGVEVHNAKT KPREEQYNST

YRVVSVLTVL HQDWLNGKEY KCKVSNKALP APIEKTISKA KGQPREPQVY TLPPSRDELT

KNQVSLTCLV KGFYPSDIAV EWESNGQPEN NYKTTPPVLD SDGSFFLYSK LTVDKSRWQQ

GNVFSCSVMH EALHNHYTQK SLSLSPGA (GGGGS)$_{n1}$X$_1$X$_2$ (GGGGS)$_{n2}$SYVL TQPPSVSVAP

*GKTARITCGG* NNIRSKSVHW *YQQKPGQAPV VVIY*YDSDRP *SGIPERISGS NSGNTATLTI*

*SRVEAGDEAD YFCQVWDSSS DHHVFGGGTK LTVL*GGGGSG GGGSGGGGSQ *VQLVQSGAEV*

*KKPGSSVKVS CKASG*GTFSS YAISWVRQAP *GQGLEWMGGI* IPIFGTANYA *QKFQGRVTIT*

*ADESTSTAYM ELSSLRSEDT AVYYCAR*VDR YYNWNYFLGS FDY*WGQGTLV TVSS;*
Wherein n$_1$ = 0, 1, 2, or 3; n$_2$ = 0, 1, 2, or 3; X$_1$ is an amino acid
Alanine or deleted; and X$_2$ is an amino acid Alanine or deleted.

CTLA-4 antibody Ipilimumab HC- scFv2 against IL-15
SEQ ID NO: 57
QVQLVESGGG VVQPGRSLRL SCAASGFTFS SYTMHWVRQA PGKGLEWVTF ISYDGNNKYY

ADSVKGRFTI SRDNSKNTLY LQMNSLRAED TAIYYCARTG WLGPFDYWGQ GTLVTVSSAS

TKGPSVFPLA PSSKSTSGGT AALGCLVKDY FPEPVTVSWN SGALTSGVHT FPAVLQSSGL

YSLSSVVTVP SSSLGTQTYI CNVNHKPSNT KVDKRVEPKS CDKTHTCPPC PAPELLGGPS

VFLFPPKPKD TLMISRTPEV TCVVVDVSHE DPEVKFNWYV DGVEVHNAKT KPREEQYNST

YRVVSVLTVL HQDWLNGKEY KCKVSNKALP APIEKTISKA KGQPREPQVY TLPPSRDELT

KNQVSLTCLV KGFYPSDIAV EWESNGQPEN NYKTTPPVLD SDGSFFLYSK LTVDKSRWQQ

GNVFSCSVMH EALHNHYTQK SLSLSPGA (GGGGS)$_{n1}$X$_1$X$_2$ (GGGGS)n2EIVL TQSPGTLSLS

PGERATLSCR ASQSVSSSYL AWYQQKPGQA PRLLIYGASR RATGIPDRFS GSGSGTDFTL

TISRLEPEDF AVYYCQRYGS SHTFGQGTKL EISGGGGSGG GGSGGGGSEV QLVQSGAEVK

KPGESLKISC KVSGYFFTTY WIGWVRQMPG KGLEYMGIIY PGDSDTRYSP SFQGQVTISA

```
DKSISTAYLQ WSSLKASDTA MYYCARGGNW NCFDYWGQGT LVTVSS
Wherein n₁ = 0, 1, 2, or 3; n₂ = 0, 1, 2, or 3; X₁ is an amino acid
Alanine or deleted; and X₂ is an amino acid Alanine or deleted.
```

CTLA-4 antibody Ipilimumab HC- IL-21R-ECD

SEQ ID NO: 58

```
QVQLVESGGG VVQPGRSLRL SCAASGFTFS SYTMHWVRQA PGKGLEWVTF ISYDGNNKYY

ADSVKGRFTI SRDNSKNTLY LQMNSLRAED TAIYYCARTG WLGPFDYWGQ GTLVTVSSAS

TKGPSVFPLA PSSKSTSGGT AALGCLVKDY FPEPVTVSWN SGALTSGVHT FPAVLQSSGL

YSLSSVVTVP SSSLGTQTYI CNVNHKPSNT KVDKRVEPKS CDKTHTCPPC PAPELLGGPS

VFLFPPKPKD TLMISRTPEV TCVVVDVSHE DPEVKFNWYV DGVEVHNAKT KPREEQYNST

YRVVSVLTVL HQDWLNGKEY KCKVSNKALP APIEKTISKA KGQPREPQVY TLPPSRDELT

KNQVSLTCLV KGFYPSDIAV EWESNGQPEN NYKTTPPVLD SDGSFFLYSK LTVDKSRWQQ

GNVFSCSVMH EALHNHYTQK SLSLSPGAGG GGSGGGGSAA GGGGSGGGGS CPDLVCYTDY

LQTVICILEM WNLHPSTLTL TWQDQYEELK DEATSCSLHR SAHNATHATY TCHMDVFHFM

ADDIFSVNIT DQSGNYSQEC GSFLLAESIK PAPPFNVTVT FSGQYNISWR SDYEDPAFYM

LKGKLQYELQ YRNRGDPWAV SPRRKLISVD SRSVSLLPLE FRKDSSYELQ VRAGPMPGSS

YQGTWSEWSD PVIFQTQSEE LKE
```

CTLA-4 antibody Ipilimumab HC- scFv2 against IL-21

SEQ ID NO: 59

```
QVQLVESGGG VVQPGRSLRL SCAASGFTFS SYTMHWVRQA PGKGLEWVTF ISYDGNNKYY

ADSVKGRFTI SRDNSKNTLY LQMNSLRAED TAIYYCARTG WLGPFDYWGQ GTLVTVSSAS

TKGPSVFPLA PSSKSTSGGT AALGCLVKDY FPEPVTVSWN SGALTSGVHT FPAVLQSSGL

YSLSSVVTVP SSSLGTQTYI CNVNHKPSNT KVDKRVEPKS CDKTHTCPPC PAPELLGGPS

VFLFPPKPKD TLMISRTPEV TCVVVDVSHE DPEVKFNWYV DGVEVHNAKT KPREEQYNST

YRVVSVLTVL HQDWLNGKEY KCKVSNKALP APIEKTISKA KGQPREPQVY TLPPSRDELT

KNQVSLTCLV KGFYPSDIAV EWESNGQPEN NYKTTPPVLD SDGSFFLYSK LTVDKSRWQQ

GNVFSCSVMH EALHNHYTQK SLSLSPGAGG GGSGGGGSAA GGGGSGGGGS EIVLTQSPGT

LSLSPGERAT LSCRASQSVS SSYLAWYQQK PGQAPRLLIY GASSRATGIP DRFSGSGSGT

DFTLTISRLE PEDFAVYYCQ QYGSWTFGQG TKVEIKGGGG SGGGGSGGGG SQVQLVESGG

GVVQPGRSLR LSCAASGFTF SSYGMHWVRQ APGKGLEWVA FIWYDGSDKY YADSVKGRFT

ISRDNSKNTL YLQMNSLRAE DTAVYYCARD GDSSDWYGDY YFGMDVW-GQGTTVTVSS
```

4E12B2D10 anti-IL2 HC variable domain (underlined:
HCDR1-3)

SEQ ID NO: 60

```
EVQLQQSGAE LVRPGASVKL SCTASGFNIK DDYLHWVRQR PEQGLEWIGR IDPANGNTKY

APKFQDKATI TADTSSNTAY LQLSILTSED TAVYYCAARF GYFYGSSFYA VAYWGQGTSV

TVSS
```

4E12B2D10 anti-IL2 LC variable domain (underlined:
LCDR1-3)

SEQ ID NO: 61

```
QIVLTQSPAI MSASPGEKVT MTCSASSSVS YMHWYQQKSG TSPKRWIYDT SKLASGVPAR

FSGSGSGTSY SLTISSMEAE DAATYYCQQW SSNPYTFGGGTKLEIK
```

-continued

IL-2 agonist polypeptide
                                                                              SEQ ID NO: 62
APX$_{aa3}$SSSTK KTQLQLEHLL LDLQMILNGI NNYKNPX$_{aa35}$LTRMLTX$_{aa4}$ZKFX$_{aa4}$SMPKKATEL KHLQCLEEEL KPLEEVLNX$_{aa72}$X$_{aa73}$QSKNFH LRPRDLISNI NVIVLELKGSE TTFMCEYADE TATIVEFLNR WITFX$_{aa125}$QS IISTLT
wherein X$_{aa3}$ is N or A; wherein X$_{aa125}$ is C, A or S; wherein X$_{aa35}$ is
selected from K and N; wherein X$_{aa42}$ is selected from A, G, S, T, Q,
E, N, D, R, and K; wherein X$_{aa45}$ is selected from A, G, S, T, Q, E, N,
D, R, and K; wherein X$_{aa72}$ is selected from A, G, S, T, Q, E, N, D, R,
and K; and wherein X$_{aa73}$ is selected from A and T.

IL-21 receptor alpha ECD mutant ver1 (mutations
underlined)
                                                                              SEQ ID NO: 63
CPDLVCYTDY LQTVICILEM WNLHPSTLTL TWQDQYEELK DEATSCSLHR SAHNATHATY

TCHMDVFHFM ADDIFSVNIT DQSGNYSQEC GSFLLAESIK PAPPFNVTVT FSGQYNISWR

SDYEDPAFYM LKGKLQYELQ YRNRGDGSGV SPRRKLISVD SRSVSLLPLE FRKDSSYELQ

VRAGPMPGSS YQGTWSEWSD PVIFQTQSEE LKE

IL-21 receptor alpha ECD mutant ver2 (mutations
underlined)
                                                                              SEQ ID NO: 64
CPDLVCYTDY LQTVICILEM WNLHPSTLTL TWQDQYEELK DEATSCSLHR SAHNATHATY

TCHMDVFHFM ADDIFSVNIT DQSGNYSQEC GSFLLAESIK PAPPFNVTVT FSGQYNISWR

SDYEDPAFYM LKGKLQYELQ YRNRGDNASV SPRRKLISVD SRSVSLLPLE FRKDSSYELQ

VRAGPMPGSS YQGTWSEWSD PVIFQTQSEE LKE

IL-21 receptor alpha ECD mutant ver3 (mutations
underlined)
                                                                              SEQ ID NO: 65
CPDLVCYTDY LQTVICILEM WNLHPSTLTL TWQDQYEELK DEATSCSLHR SAHNATHATY

TCHMDVFHFM ADDIFSVNIT DQSGNYSQEC GSFLLAESIK PAPPFNVTVT FSGQYNISWR

SDYEDPAFYM LKGKLQYELQ YRNRGDNGSV SPRRKLISVD SRSVSLLPLE FRKDSSYELQ

VRAGPMPGSS YQGTWSEWSD PVIFQTQSEE LKE

TL-21 receptor alpha ECD mutant ver4 (mutations
underlined)
                                                                              SEQ ID NO: 66
LQTVICILEM WNLHPSTLTL TWQDQYEELK DEATSCSLNR SAHNATHATY CPDLVCYTDY

TCHMDVFHFM ADDIFSVNIT DQSGNYSQEC GSFLLAESIK PAPPFNVTVT FSGQYNISWR

SDYEDPAFYM LKGKLQYELQ YRNRGDNASV SPRRKLISVD SRSVSLLPLE FRKDSSYELQ

VRAGPMPGSS YQGTWSEWSD PVIFQTQSEE LKE

IL-21 receptor alpha ECD mutant ver5 (mutations
underlined)
                                                                              SEQ ID NO: 67
CPDLVCYTDY LQTVICILEM WNLHPSTLTL TWQDQYEELK DEATSCSLHR SAHNATHATY

TCHMDVFHFM ADDIFSVNIT DQSGNYSQEC GSFLLAESIK PAPPFNVTVT FSGQYNISWR

SDYEDPAFYM LKGKLQYELQ YRNRGDPSAV SPRRKLISVD SRSVSLLPLE FRKDSSYELQ

VRAGPMPGSS YQGTWSEWSD PVIFQTQSEE LKE

IL-21 receptor alpha ECD mutant ver6 (mutations
underlined)
                                                                              SEQ ID NO: 68
CPDLVCYTDY LQTVICILEM WNLHPSTLTL TWQDQYEELK DEATSCSLHR SAHNATHATY

TCHMDVFHFM ADDIFSVNIT DQSGNYSQEC GSFLLAESIK PAPPFNVTVT FSGQYNISWR

SDYEDPAFYM LKGKLQYELQ YRNRGDPSGV SPRRKLISVD SRSVSLLPLE FRKDSSYELQ

VRAGPMPGSS YQGTWSEWSD PVIFQTQSEE LKE

-continued

IL-21 receptor alpha ECD mutant ver7 (mutations
underlined)
SEQ ID NO: 69
CPDLVCYTDY LQTVICILEM WNLHPSTLTL TWQDQYEELK DEATSCSLHR SAHNATHATY

TCHMDVFHFM ADDIFSVNIT DQSGNYSQEC GSFLLAESIK PAPPFNVTVT FSGQYNISWR

SAYEDPAFYM LKGKLQYELQ YRNRGDGSGV SPRRKLISVD SRSVSLLPLE FRKDSSYELQ

VRAGPMPGSS YQGTWSEWSD PVIFQTQSEE LKE

IL-21 receptor alpha ECD mutant ver8 (mutations
underlined)
SEQ ID NO: 70
CPDLVCYTDY LQTVICILEM WNLHPSTLTL TWQDQYEELK DEATSCSLHR SAHNATHATY

TCHMDVFHFM ADDIFSVNIT DQSGNYSQEC GSFLLAESIK PAPPFNVTVT FSGQYNISWR

SIYEDPAFYM LKGKLQYELQ YRNRGDGSGV SPRRKLISVD SRSVSLLPLE FRKDSSYELQ

VRAGPMPGSS YQGTWSEWSD PVIFQTQSEE LKE

IL-21 receptor alpha ECD mutant ver9 (mutations
underlined)
SEQ ID NO: 71
CPDLVCYTDY LQTVICILEM WNLHPSTLTL TWQDQYEELK DEATSCSLHR SAHNATHATY

TCHMDVFHFM ADDIFSVNIT DQSGNYSQEC GSFLLAESIK PAPPFNVTVT FSGQYNISWR

SWYEDPAFYM LKGKLQYELQ YRNRGDGSGV SPRRKLISVD SRSVSLLPLE FRKDSSYELQ

VRAGPMPGSS YQGTWSEWSD PVIFQTQSEE LKE

IL-21 receptor alpha ECD mutant ver10 (mutations
underlined)
SEQ ID NO: 72
CPDLVCYTDY LQTVICILEM WNLHPSTLTL TWQDQYEELK DEATSCSLHR SAHNATHAT

TCHMDVFHFM ADDIFSVNIT DQSGNYSQEC GSFLLAESIK PAPPFNVTVT FSGQYNISWR

SFYEDPAFYM LKGKLQYELQ YRNRGDGSGV SPRRKLISVD SRSVSLLPLE FRKDSSYELQ

VRAGPMPGSS YQGTWSEWSD PVIFQTQSEE LKE

IL-21 receptor alpha ECD mutant ver11
SEQ ID NO: 73
CPDLVCYTDY LQTVICILEM WNLHPSTLTL TWQDQYEELK DEATSCSLHR SAHNATHATY

TCHMDVFHFM ADDIFSVNIT DQSGNYSQEC GSFLLAESIK PAPPFNVTVT FSGQYNISWR

SYYEDPAFYM LKGKLQYELQ YRNRGDGSGV SPRRKLISVD SRSVSLLPLE FRKDSSYELQ

VRAGPMPGSS YQGTWSEWSD PVIFQTQSEE LKE

PD1-HC with hole mutations IL-21Rα ECD
SEQ ID NO: 74
QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VCTLPPSQEE MTKNQVSLSC

AVKGFYPSDI AVEWESNGQP ENNYKTTPPV LDSDGSFFLV SRLTVDKSRW QEGNVFSCSV

MHEALHNHYT QKSLSLSLGA GGGGSGGGGS GPLGVRGGGG SCPDLVCYTD YLQTVICILE

MWNLHPSTLT LTWQDQYEEL KDEATSCSLH RSAHNATHAT YTCHMDVFHF MADDIFSVNI

TDQSGNYSQE CGSFLLAESI KPAPPFNVTV TFSGQYNISW RSDYEDPAFY MLKGKLQYEL

QYRNRGDPWA VSPRRKLISV DSRSVSLLPL EFRKDSSYEL QVRAGPMPGS SYQGTWSEWS

DPVIFQTQSE ELKE

-continued

PD1-HC fusion polypeptide with scFv2 against IL-15

SEQ ID NO: 75

QVQLVESGGG VVQPGRSLRL DCKASGITFS NSGMHWVRQA PGKGLEWVAV IWYDGSKRYY

ADSVKGRFTI SRDNSKNTLF LQMNSLRAED TAVYYCATND DYWGQGTLVT VSSASTKGPS

VFPLAPCSRS TSESTAALGC LVKDYFPEPV TVSWNSGALT SGVHTFPAVL QSSGLYSLSS

VVTVPSSSLG TKTYTCNVDH KPSNTKVDKR VESKYGPPCP PCPAPEFLGG PSVFLFPPKP

KDTLMISRTP EVTCVVVDVS QEDPEVQFNW YVDGVEVHNA KTKPREEQFN STYRVVSVLT

VLHQDWLNGK EYKCKVSNKG LPSSIEKTIS KAKGQPREPQ VYTLPPSQEE MTKNQVSLTC

LVKGFYPSDI AVEWESNGQP ENNYKTTPPV LDSDGSFFLY SRLTVDKSRW QEGNVFSCSV

MHEALHNHYT QKSLSLSLGA GGGGSGGGGS GPLGVRGGGG SGGGGSEIVL TQSPGTLSLS

PGERATLSCR ASQSVSSSYL AWYQQKPGQA PRLLIYGASR RATGIPDRFS GSGSGTDFTL

TISRLEPEDF AVYYCQRYGS SHTFGQGTKL EISGGGGSGG GGSGGGGSEV QLVQSGAEVK

KPGESLKISC KVSGYFFTTY WIGWVRQMPG KGLEYMGIIY PGDSDTRYSP SFQGQVTISA

DKSISTAYLQ WSSLKASDTA MYYCARGGNW NCFDYWGQGT LVTVSS

Anti-IL-15 antibody 146B7 HC CDR1 (protein sequence

SEQ ID NO: 76

TYWIG

Anti-IL-15 antibody 146B7 HC CDR2 (protein sequence

SEQ ID NO: 77

IIYPGDSDTR YSPSFQG

Anti-IL-15 antibody 146B7 HC CDR3 (protein sequence

SEQ ID NO: 78

GNWNCFDY

Anti-IL-15 antibody 146B7 LC CDR1 (protein sequence

SEQ ID NO: 79

RASQSVSSSYLA

Anti-IL-15 antibody 146B7 LC CDR2 (protein sequence

SEQ ID NO: 80

GASRRAT

Anti-IL-15 antibody 146B7 LC CDR3 (protein sequence

SEQ ID NO: 81

QRYGSSHT

Anti-IL-15 antibody 146B7 HC CDR3 ver2 (protein Sequence)

SEQ ID NO: 82

GNWNSFDY

Anti-IL-15 antibody 146B7 HC variable domain
(underlined: HCDR1-3)

SEQ ID NO: 83

EVQLVQSGAE VKKPGESLKI SCKVSGYFFT TYWIGWVRQM PGKGLEYMGI IYPGDSDTRY

SPSFQGQVTI SADKSISTAY LQWSSLKASD TAMYYCARGG NWNCFDYWGQ GTLVTVSS

Anti-IL-15 antibody 146B7 LC variable domain
(underlined: LCDR1-3)

SEQ ID NO: 84

EIVLTQSPGT LSLSPGREAT LSCRASQSVS SSYLAWYQQK PGQAPRLLIY GASRRATGIP

DRFSGSGSGT DFTLTISRLE PEDFAVYYCQ RYGSSHTFGQ GTKLEISRTV AAPSVFIFP

The invention claimed is:

1. A prodrug comprising a cytokine moiety, a masking moiety, and a carrier moiety, wherein:
   a) the masking moiety binds to the cytokine moiety and inhibits a biological activity of the cytokine, wherein the masking moiety comprises a single chain variable fragment (scFv) against the cytokine moiety or comprises an extracellular domain (ECD) of a receptor for the cytokine moiety;
   b) the carrier moiety comprises an antigen-binding moiety, wherein the antigen-binding moiety binds to an antigen expressed on the surface of a target immune cell; and
   c) the masking moiety is linked directly or indirectly to the carrier moiety;
   wherein the target immune cell expresses on its surface a cytokine receptor for the cytokine moiety such that when the prodrug binds to the antigen on the target immune cell through the antigen-binding moiety, the cytokine moiety binds to the cytokine receptor on the target immune cell and exerts the biological activity on the target immune cell,
   wherein the cytokine moiety comprises an IL-2 polypeptide, an IL-7 polypeptide, or an IL-21 polypeptide.

2. The prodrug of claim 1, wherein the receptor for the cytokine moiety comprises two or more subunits.

3. The prodrug of claim 1, wherein the antigen is selected from Programmed Cell Death 1 (PD-1), Programmed Cell Death Ligand 1 (PD-L1), Cytotoxic T-lymphocyte Associated Protein 4 (CTLA-4), T-cell Immunoreceptor with Ig and ITIM Domains (TIGIT), T-cell Immunoglobulin and Mucin Domain containing-3 (TIM-3), Lymphocyte Activation Gene 3 (LAG-3), Cluster of Differentiation 25 (CD25), Cluster of Differentiation 16a (CD16a), Cluster of Differentiation 16b (CD16b), Natural Killer Group 2 Member D (NKG2D), Natural Killer Cell P44-related protein (NKP44), Natural Killer Cell Proliferation-associated Gene P30 (NKP30), Cluster of Differentiation 19 (CD19), Cluster of Differentiation 20 (CD20), Cluster of Differentiation 30 (CD30), Cluster of Differentiation 38 (CD38), B-cell Maturation Antigen (BCMA), and signal regulatory protein alpha (SIRP alpha).

4. The prodrug of claim 1, wherein the cytokine moiety comprises an IL-2 polypeptide.

5. The prodrug of claim 1, wherein the immune cell is a T cell, the antigen is PD-1, and the cytokine moiety comprises an IL-2.

6. The prodrug of claim 1, wherein
   i) the cytokine moiety comprises an IL-7 polypeptide and the masking moiety comprises an extracellular domain (ECD) of IL-7 receptor α (IL-7Rα ECD),
   ii) the cytokine moiety comprises an IL-21 polypeptide and the masking moiety comprises an ECD of IL-21 receptor α (IL-21Rα ECD),
   iii) the cytokine moiety comprises an IL-2 polypeptide and the masking moiety comprises an ECD of IL-2 receptor β (IL-2Rβ ECD),
   iv) the cytokine moiety comprises an IL-21 polypeptide and the masking moiety comprises an scFv against IL-21, or
   v) the cytokine moiety comprises an IL-2 polypeptide and the masking moiety comprises an scFv against IL-2.

7. The prodrug of claim 6, wherein the cytokine moiety comprises an IL-2 polypeptide comprising SEQ ID NO: 6 or SEQ ID NO: 62.

8. The prodrug of claim 6, wherein the cytokine moiety comprises an IL-2 polypeptide comprising an amino acid sequence that is at least 95% identical to SEQ ID NO: 6 or SEQ ID NO: 62.

9. The prodrug of claim 6, wherein the cytokine moiety comprises an IL-2 polypeptide and the masking moiety comprises an IL-2Rβ ECD, wherein the IL-2-Rβ ECD comprises SEQ ID NO: 11, or an amino acid sequence that is at least 95% identical thereto.

10. The prodrug of claim 6, wherein the cytokine moiety comprises an IL-2 polypeptide and the masking moiety comprises an scFv against IL-2, and wherein the scFv comprises:
   a) a heavy chain complementarity-determining region 1 (HCDR1), a heavy chain complementarity-determining region 2 (HCDR2), a heavy chain complementarity-determining region 3 (HCDR3), a light chain complementarity-determining region 1 (LCDR1), a light chain complementarity-determining region 2 (LCDR2), and a light chain complementarity-determining region 3 (LCDR3) of an scFv sequence set forth in SEQ ID NO: 22 or SEQ ID NO: 23,
   b) the heavy and light chain variable domains of an scFv sequence set forth in SEQ ID NO: 22 or SEQ ID NO: 23, or
   c) an HCDR1, an HCDR2, and an HCDR3 of a heavy chain variable domain sequence set forth in SEQ ID NO: 60 and a LCDR1, a LCDR2 and a LCDR3 of a light chain variable domain sequence set forth in SEQ ID NO: 61.

11. The prodrug of claim 6, wherein the cytokine moiety comprises an IL-2 polypeptide and the masking moiety comprises an scFv against IL-2, wherein the scFv comprises:
   a) SEQ ID NO: 22 or SEQ ID NO: 23, or an amino acid sequence that is at least 95% identical thereto; or
   b) SEQ ID NOs: 60 and 61.

12. The prodrug of claim 6, wherein the cytokine moiety comprises an IL-21 polypeptide comprising any one of SEQ ID NOs: 1-5, or an amino acid sequence that is at least 95% identical thereto.

13. The prodrug of claim 6, wherein the cytokine moiety comprises an IL-21 polypeptide and the masking moiety comprises an IL-21Ra ECD, or an IL-21Ry ECD, wherein the masking moiety comprises any one of SEQ ID NOs: 12, 13, and 63-73, or an amino acid sequence that is at least 95% identical thereto.

14. The prodrug of claim 6, wherein the cytokine moiety comprises an IL-21 polypeptide and the masking moiety comprises an scFv against human IL-21, wherein the scFv comprises:

a) an HCDR1, an HCDR2, an HCDR3, a LCDR1, a LCDR2, and a LCDR3 of an scFv sequence set forth in SEQ ID NO: 20 or SEQ ID NO: 21, b) the heavy and light chain variable domains of an scFv sequence set forth in SEQ ID NO: 20 or SEQ ID NO: 21, or c) SEQ ID NO: 20 or SEQ ID NO: 21, or an amino acid sequence that is at least 95% identical thereto.

15. The prodrug of claim 1, wherein the masking moiety comprises an ECD of a receptor α or γ of the cytokine.

16. The prodrug of claim 1, wherein the prodrug comprises an anti-PD-1 antibody moiety, wherein the anti-PD-1 antibody moiety comprises two light chains each comprising SEQ ID NO: 44, and two heavy chains comprising respectively:

SEQ ID NOs: 24 and 25,
SEQ ID NOs: 35 and 36,
SEQ ID NOs: 39 and 41,
SEQ ID NOs: 42 and 43, or
SEQ ID NOs: 42 and 74.

17. The prodrug of claim 1, wherein the prodrug comprises an anti-CTLA4 antibody moiety, wherein the anti-CTLA4 antibody moiety comprises two light chains each comprising SEQ ID NO: 50, and two heavy chains comprising respectively:

SEQ ID NOs: 51 and 54,
SEQ ID NOs: 51 and 55,
SEQ ID NOs: 51 and 56,
SEQ ID NOs: 53 and 58, or
SEQ ID NOs: 53 and 59.

18. A pharmaceutical composition comprising the prodrug of claim 1 and a pharmaceutically acceptable excipient.

19. The prodrug of claim 1, wherein the immune cell is a T cell, the antigen is PD-1, and the cytokine moiety comprises an IL-21 polypeptide.

* * * * *

SEQUENCE LISTING

<160> NUMBER OF SEQ ID NOS: 84

<210> SEQ ID NO 1
<211> LENGTH: 133
<212> TYPE: PRT
<213> ORGANISM: Homo sapiens

```
<400> SEQUENCE: 1

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 2
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 2

Gln Gly Gln Asp Arg His Met Ile Arg Met Arg Gln Leu Ile Asp Ile
1               5                   10                  15

Val Ala Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 3
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 3
```

```
Gln Gly Gln Asp Arg His Met Ile Arg Met Arg Gln Leu Ile Asp Ile
1               5                   10                  15

Val Lys Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser
        130
```

```
<210> SEQ ID NO 4
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4
```

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Arg Arg Phe Lys
                100                 105                 110

Ser Leu Leu Gln Lys Met Ile His Gln His Leu Ser Ser Arg Thr His
            115                 120                 125

Gly Ser Glu Asp Ser
        130
```

```
<210> SEQ ID NO 5
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5
```

-continued

```
Gln Gly Gln Asp Arg His Met Ile Arg Met Arg Gln Leu Ile Asp Ile
1               5                   10                  15

Val Asp Lys Leu Lys Asn Tyr Val Asn Asp Leu Val Pro Glu Phe Leu
        20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Arg Arg Phe Lys
                100                 105                 110

Ser Leu Leu Gln Lys Met Ile His Gln His Leu Ser Ser Arg Thr His
                115                 120                 125

Gly Ser Glu Asp Ser
        130
```

```
<210> SEQ ID NO 6
<211> LENGTH: 133
<212> TYPE: PRT
<213> ORGANISM: Homo sapiens

<400> SEQUENCE: 6
```

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
        20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
        130
```

```
<210> SEQ ID NO 7
<211> LENGTH: 113
<212> TYPE: PRT
<213> ORGANISM: Homo sapiens

<400> SEQUENCE: 7
```

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
        20                  25                  30

Pro Ser Cys Lys Val Thr Ala Met Lys Cys Phe Leu Leu Glu Leu Gln
        35                  40                  45
```

-continued

```
Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr
```

```
<210> SEQ ID NO 8
<211> LENGTH: 75
<212> TYPE: PRT
<213> ORGANISM: Homo sapiens

<400> SEQUENCE: 8

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Ala Leu Val His Gln Arg Pro Ala
65                  70                  75
```

```
<210> SEQ ID NO 9
<211> LENGTH: 152
<212> TYPE: PRT
<213> ORGANISM: Homo sapiens

<400> SEQUENCE: 9

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
                100                 105                 110

Leu Glu Glu Asn Lys Ser Leu Lys Glu Gln Lys Lys Leu Asn Asp Leu
            115                 120                 125

Cys Phe Leu Lys Arg Leu Leu Gln Glu Ile Lys Thr Cys Trp Asn Lys
        130                 135                 140

Ile Leu Met Gly Thr Lys Glu His
145                 150
```

```
<210> SEQ ID NO 10
<211> LENGTH: 126
<212> TYPE: PRT
```

<213> ORGANISM: Homo sapiens

<400> SEQUENCE: 10

```
Gln Gly Cys Pro Thr Leu Ala Gly Ile Leu Asp Ile Asn Phe Leu Ile
1               5                   10                  15

Asn Lys Met Gln Glu Asp Pro Ala Ser Lys Cys His Cys Ser Ala Asn
            20                  25                  30

Val Thr Ser Cys Leu Cys Leu Gly Ile Pro Ser Asp Asn Cys Thr Arg
        35                  40                  45

Pro Cys Phe Ser Glu Arg Leu Ser Gln Met Thr Asn Thr Thr Met Gln
    50                  55                  60

Thr Arg Tyr Pro Leu Ile Phe Ser Arg Val Lys Lys Ser Val Glu Val
65                  70                  75                  80

Leu Lys Asn Asn Lys Cys Pro Tyr Phe Ser Cys Glu Gln Pro Cys Asn
                85                  90                  95

Gln Thr Thr Ala Gly Asn Ala Leu Thr Phe Leu Lys Ser Leu Leu Glu
            100                 105                 110

Ile Phe Gln Lys Glu Lys Met Arg Gly Met Arg Gly Lys Ile
            115                 120                 125
```

<210> SEQ ID NO 11
<211> LENGTH: 214
<212> TYPE: PRT
<213> ORGANISM: Homo sapiens

<400> SEQUENCE: 11

```
Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
            115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
            195                 200                 205

Ala Leu Gly Lys Asp Thr
    210
```

<210> SEQ ID NO 12
<211> LENGTH: 213
<212> TYPE: PRT
<213> ORGANISM: Homo sapiens

<400> SEQUENCE: 12

```
Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
            20                  25                  30

Gln Asp Gln Tyr Glu Glu Leu Lys Asp Glu Ala Thr Ser Cys Ser Leu
        35                  40                  45

His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
            100                 105                 110

Gly Gln Tyr Asn Ile Ser Trp Arg Ser Asp Tyr Glu Asp Pro Ala Phe
        115                 120                 125

Tyr Met Leu Lys Gly Lys Leu Gln Tyr Glu Leu Gln Tyr Arg Asn Arg
    130                 135                 140

Gly Asp Pro Trp Ala Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
            180                 185                 190

Gly Thr Trp Ser Glu Trp Ser Asp Pro Val Ile Phe Gln Thr Gln Ser
        195                 200                 205

Glu Glu Leu Lys Glu
    210
```

<210> SEQ ID NO 13
<211> LENGTH: 240
<212> TYPE: PRT
<213> ORGANISM: Homo sapiens

<400> SEQUENCE: 13

```
Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
```

-continued

```
            115                 120                 125
Leu Val Ile Pro Trp Ala Pro Glu Asn Leu Thr Leu His Lys Leu Ser
    130                 135                 140
Glu Ser Gln Leu Glu Leu Asn Trp Asn Asn Arg Phe Leu Asn His Cys
145                 150                 155                 160
Leu Glu His Leu Val Gln Tyr Arg Thr Asp Trp Asp His Ser Trp Thr
                165                 170                 175
Glu Gln Ser Val Asp Tyr Arg His Lys Phe Ser Leu Pro Ser Val Asp
                180                 185                 190
Gly Gln Lys Arg Tyr Thr Phe Arg Val Arg Ser Arg Phe Asn Pro Leu
                195                 200                 205
Cys Gly Ser Ala Gln His Trp Ser Glu Trp Ser His Pro Ile His Trp
    210                 215                 220
Gly Ser Asn Thr Ser Lys Glu Asn Pro Phe Leu Phe Ala Leu Glu Ala
225                 230                 235                 240

<210> SEQ ID NO 14
<211> LENGTH: 219
<212> TYPE: PRT
<213> ORGANISM: Homo sapiens

<400> SEQUENCE: 14

Glu Ser Gly Tyr Ala Gln Asn Gly Asp Leu Glu Asp Ala Glu Leu Asp
1               5                   10                  15
Asp Tyr Ser Phe Ser Cys Tyr Ser Gln Leu Glu Val Asn Gly Ser Gln
                20                  25                  30
His Ser Leu Thr Cys Ala Phe Glu Asp Pro Asp Val Asn Ile Thr Asn
            35                  40                  45
Leu Glu Phe Glu Ile Cys Gly Ala Leu Val Glu Val Lys Cys Leu Asn
    50                  55                  60
Phe Arg Lys Leu Gln Glu Ile Tyr Phe Ile Glu Thr Lys Lys Phe Leu
65                  70                  75                  80
Leu Ile Gly Lys Ser Asn Ile Cys Val Lys Val Gly Glu Lys Ser Leu
                85                  90                  95
Thr Cys Lys Lys Ile Asp Leu Thr Thr Ile Val Lys Pro Glu Ala Pro
            100                 105                 110
Phe Asp Leu Ser Val Val Tyr Arg Glu Gly Ala Asn Asp Phe Val Val
            115                 120                 125
Thr Phe Asn Thr Ser His Leu Gln Lys Lys Tyr Val Lys Val Leu Met
    130                 135                 140
His Asp Val Ala Tyr Arg Gln Glu Lys Asp Glu Asn Lys Trp Thr His
145                 150                 155                 160
Val Asn Leu Ser Ser Thr Lys Leu Thr Leu Leu Gln Arg Lys Leu Gln
                165                 170                 175
Pro Ala Ala Met Tyr Glu Ile Lys Val Arg Ser Ile Pro Asp His Tyr
                180                 185                 190
Phe Lys Gly Phe Trp Ser Glu Trp Ser Pro Ser Tyr Tyr Phe Arg Thr
                195                 200                 205
Pro Glu Ile Asn Asn Ser Ser Gly Glu Met Asp
    210                 215

<210> SEQ ID NO 15
<211> LENGTH: 230
<212> TYPE: PRT
<213> ORGANISM: Homo sapiens
```

```
<400> SEQUENCE: 15

Ser Val Thr Gly Glu Gly Gln Gly Pro Arg Ser Arg Thr Phe Thr Cys
1               5                   10                  15

Leu Thr Asn Asn Ile Leu Arg Ile Asp Cys His Trp Ser Ala Pro Glu
            20                  25                  30

Leu Gly Gln Gly Ser Ser Pro Trp Leu Leu Phe Thr Ser Asn Gln Ala
        35                  40                  45

Pro Gly Gly Thr His Lys Cys Ile Leu Arg Gly Ser Glu Cys Thr Val
    50                  55                  60

Val Leu Pro Pro Glu Ala Val Leu Val Pro Ser Asp Asn Phe Thr Ile
65                  70                  75                  80

Thr Phe His His Cys Met Ser Gly Arg Glu Gln Val Ser Leu Val Asp
                85                  90                  95

Pro Glu Tyr Leu Pro Arg Arg His Val Lys Leu Asp Pro Pro Ser Asp
            100                 105                 110

Leu Gln Ser Asn Ile Ser Ser Gly His Cys Ile Leu Thr Trp Ser Ile
            115                 120                 125

Ser Pro Ala Leu Glu Pro Met Thr Thr Leu Leu Ser Tyr Glu Leu Ala
    130                 135                 140

Phe Lys Lys Gln Glu Glu Ala Trp Glu Gln Ala Gln His Arg Asp His
145                 150                 155                 160

Ile Val Gly Val Thr Trp Leu Ile Leu Glu Ala Phe Glu Leu Asp Pro
                165                 170                 175

Gly Phe Ile His Glu Ala Arg Leu Arg Val Gln Met Ala Thr Leu Glu
            180                 185                 190

Asp Asp Val Val Glu Glu Glu Arg Tyr Thr Gly Gln Trp Ser Glu Trp
            195                 200                 205

Ser Gln Pro Val Cys Phe Gln Ala Pro Gln Arg Gln Gly Pro Leu Ile
    210                 215                 220

Pro Pro Trp Gly Trp Pro
225                 230

<210> SEQ ID NO 16
<211> LENGTH: 500
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

-continued

```
Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Ala Gly Gly Gly Gly Ser Val His Met Pro Leu Gly Phe Leu
225                 230                 235                 240

Gly Pro Arg Gln Ala Arg Val Val Asn Gly Gly Gly Gly Ser Gly
                245                 250                 255

Gly Gly Gly Ser Glu Ile Val Leu Thr Gln Ser Pro Gly Thr Leu Ser
                260                 265                 270

Leu Ser Pro Gly Glu Arg Ala Thr Leu Ser Cys Arg Ala Ser Gln Ser
            275                 280                 285

Val Ser Ser Ser Tyr Leu Ala Trp Tyr Gln Gln Lys Pro Gly Gln Ala
    290                 295                 300

Pro Arg Leu Leu Ile Tyr Gly Ala Ser Arg Arg Ala Thr Gly Ile Pro
305                 310                 315                 320

Asp Arg Phe Ser Gly Ser Gly Ser Gly Thr Asp Phe Thr Leu Thr Ile
                325                 330                 335

Ser Arg Leu Glu Pro Glu Asp Phe Ala Val Tyr Tyr Cys Gln Arg Tyr
            340                 345                 350

Gly Ser Ser His Thr Phe Gly Gln Gly Thr Lys Leu Glu Ile Ser Gly
            355                 360                 365

Gly Gly Gly Ser Gly Gly Gly Gly Ser Gly Gly Gly Gly Ser Glu Val
    370                 375                 380

Gln Leu Val Gln Ser Gly Ala Glu Val Lys Lys Pro Gly Glu Ser Leu
385                 390                 395                 400

Lys Ile Ser Cys Lys Val Ser Gly Tyr Phe Phe Thr Thr Tyr Trp Ile
            405                 410                 415

Gly Trp Val Arg Gln Met Pro Gly Lys Gly Leu Glu Tyr Met Gly Ile
            420                 425                 430

Ile Tyr Pro Gly Asp Ser Asp Thr Arg Tyr Ser Pro Ser Phe Gln Gly
            435                 440                 445

Gln Val Thr Ile Ser Ala Asp Lys Ser Ile Ser Thr Ala Tyr Leu Gln
    450                 455                 460

Trp Ser Ser Leu Lys Ala Ser Asp Thr Ala Met Tyr Tyr Cys Ala Arg
465                 470                 475                 480

Gly Gly Asn Trp Asn Cys Phe Asp Tyr Trp Gly Gln Gly Thr Leu Val
                485                 490                 495

Thr Val Ser Ser
            500
```

<210> SEQ ID NO 17
<211> LENGTH: 452

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Ala Gly Gly Gly Gly Ser Gly Gly Gly Ser Gly Gly Gly
225                 230                 235                 240

Gly Ser Ile Thr Cys Pro Pro Pro Met Ser Val Glu His Ala Asp Ile
            245                 250                 255

Trp Val Lys Ser Tyr Ser Leu Tyr Ser Arg Glu Arg Tyr Ile Cys Asn
            260                 265                 270

Ser Gly Phe Lys Arg Lys Ala Gly Thr Ser Ser Leu Thr Glu Cys Val
            275                 280                 285

Leu Asn Lys Ala Thr Asn Val Ala His Trp Thr Thr Pro Ser Leu Lys
    290                 295                 300

Cys Ile Arg Gly Gly Gly Gly Ser Gly Gly Gly Ser Gly Gly Gly Gly
305                 310                 315                 320

Ser Ala Ala Gly Gly Gly Gly Ser Gly Gly Gly Ser Gly Gly Gly
            325                 330                 335

Gly Ser Asn Trp Val Asn Val Ile Ser Asp Leu Lys Lys Ile Glu Asp
            340                 345                 350

Leu Ile Gln Ser Met His Ile Asp Ala Thr Leu Tyr Thr Glu Ser Asp
    355                 360                 365

Val His Pro Ser Cys Lys Val Thr Ala Met Lys Cys Phe Leu Leu Glu
```

```
            370                 375                 380

Leu Gln Val Ile Ser Leu Glu Ser Gly Asp Ala Ser Ile His Asp Thr
385                 390                 395                 400

Val Glu Asp Leu Ile Ile Leu Ala Asn Asn Ser Leu Ser Ser Asn Gly
                405                 410                 415

Asn Val Thr Glu Ser Gly Cys Lys Glu Cys Glu Glu Leu Glu Glu Lys
                420                 425                 430

Asn Ile Lys Glu Phe Leu Gln Ser Phe Val His Ile Val Gln Met Phe
                435                 440                 445

Ile Asn Thr Ser
        450

<210> SEQ ID NO 18
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Phe Phe Thr Thr Tyr
                20                  25                  30

Trp Ile Gly Trp Val Arg Gln Met Pro Gly Lys Gly Leu Glu Tyr Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asn Trp Asn Cys Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Ile Val Leu Thr Gln Ser Pro Gly Thr Leu
        130                 135                 140

Ser Leu Ser Pro Gly Glu Arg Ala Thr Leu Ser Cys Arg Ala Ser Gln
145                 150                 155                 160

Ser Val Ser Ser Ser Tyr Leu Ala Trp Tyr Gln Gln Lys Pro Gly Gln
                165                 170                 175

Ala Pro Arg Leu Leu Ile Tyr Gly Ala Ser Arg Arg Ala Thr Gly Ile
            180                 185                 190

Pro Asp Arg Phe Ser Gly Ser Gly Ser Gly Thr Asp Phe Thr Leu Thr
            195                 200                 205

Ile Ser Arg Leu Glu Pro Glu Asp Phe Ala Val Tyr Tyr Cys Gln Arg
        210                 215                 220

Tyr Gly Ser Ser His Thr Phe Gly Gln Gly Thr Lys Leu Glu Ile Ser
225                 230                 235                 240

<210> SEQ ID NO 19
<211> LENGTH: 240
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Arg Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser His
                85                  90                  95

Thr Phe Gly Gln Gly Thr Lys Leu Glu Ile Ser Gly Gly Gly Gly Ser
            100                 105                 110

Gly Gly Gly Gly Ser Gly Gly Gly Gly Ser Glu Val Gln Leu Val Gln
            115                 120                 125

Ser Gly Ala Glu Val Lys Lys Pro Gly Glu Ser Leu Lys Ile Ser Cys
    130                 135                 140

Lys Val Ser Gly Tyr Phe Phe Thr Thr Tyr Trp Ile Gly Trp Val Arg
145                 150                 155                 160

Gln Met Pro Gly Lys Gly Leu Glu Tyr Met Gly Ile Ile Tyr Pro Gly
                165                 170                 175

Asp Ser Asp Thr Arg Tyr Ser Pro Ser Phe Gln Gly Gln Val Thr Ile
            180                 185                 190

Ser Ala Asp Lys Ser Ile Ser Thr Ala Tyr Leu Gln Trp Ser Ser Leu
            195                 200                 205

Lys Ala Ser Asp Thr Ala Met Tyr Tyr Cys Ala Arg Gly Gly Asn Trp
    210                 215                 220

Asn Cys Phe Asp Tyr Trp Gly Gln Gly Thr Leu Val Thr Val Ser Ser
225                 230                 235                 240

<210> SEQ ID NO 20
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Trp Tyr Asp Gly Ser Asp Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Gly Asp Ser Ser Asp Trp Tyr Gly Asp Tyr Tyr Phe Gly
            100                 105                 110

Met Asp Val Trp Gly Gln Gly Thr Thr Val Thr Val Ser Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Gly Thr Leu Ser Leu Ser Pro Gly Glu Arg Ala
145                 150                 155                 160

Thr Leu Ser Cys Arg Ala Ser Gln Ser Val Ser Ser Ser Tyr Leu Ala
                165                 170                 175

Trp Tyr Gln Gln Lys Pro Gly Gln Ala Pro Arg Leu Leu Ile Tyr Gly
            180                 185                 190

Ala Ser Ser Arg Ala Thr Gly Ile Pro Asp Arg Phe Ser Gly Ser Gly
            195                 200                 205

Ser Gly Thr Asp Phe Thr Leu Thr Ile Ser Arg Leu Glu Pro Glu Asp
    210                 215                 220

Phe Ala Val Tyr Tyr Cys Gln Gln Tyr Gly Ser Trp Thr Phe Gly Gln
225                 230                 235                 240

Gly Thr Lys Val Glu Ile Lys
                245
```

```
<210> SEQ ID NO 21
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Trp Thr
                85                  90                  95

Phe Gly Gln Gly Thr Lys Val Glu Ile Lys Gly Gly Gly Gly Ser Gly
            100                 105                 110

Gly Gly Gly Ser Gly Gly Gly Gly Ser Gln Val Gln Leu Val Glu Ser
        115                 120                 125

Gly Gly Gly Val Val Gln Pro Gly Arg Ser Leu Arg Leu Ser Cys Ala
    130                 135                 140

Ala Ser Gly Phe Thr Phe Ser Ser Tyr Gly Met His Trp Val Arg Gln
145                 150                 155                 160

Ala Pro Gly Lys Gly Leu Glu Trp Val Ala Phe Ile Trp Tyr Asp Gly
            165                 170                 175

Ser Asp Lys Tyr Tyr Ala Asp Ser Val Lys Gly Arg Phe Thr Ile Ser
```

-continued

```
                180              185              190

Arg Asp Asn Ser Lys Asn Thr Leu Tyr Leu Gln Met Asn Ser Leu Arg
        195              200              205

Ala Glu Asp Thr Ala Val Tyr Tyr Cys Ala Arg Asp Gly Asp Ser Ser
    210              215              220

Asp Trp Tyr Gly Asp Tyr Tyr Phe Gly Met Asp Val Trp Gly Gln Gly
225              230              235              240

Thr Thr Val Thr Val Ser Ser
            245

<210> SEQ ID NO 22
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gln Val Gln Leu Val Gln Ser Gly Ala Glu Val Lys Lys Pro Gly Ser
1               5               10               15

Ser Val Lys Val Ser Cys Lys Ala Ser Gly Gly Thr Phe Ser Ser Tyr
            20               25               30

Ala Ile Ser Trp Val Arg Gln Ala Pro Gly Gln Gly Leu Glu Trp Met
        35               40               45

Gly Gly Ile Ile Pro Ile Phe Gly Thr Ala Asn Tyr Ala Gln Lys Phe
    50               55               60

Gln Gly Arg Val Thr Ile Thr Ala Asp Glu Ser Thr Ser Thr Ala Tyr
65               70               75               80

Met Glu Leu Ser Ser Leu Arg Ser Glu Asp Thr Ala Val Tyr Tyr Cys
            85               90               95

Ala Arg Val Asp Arg Tyr Tyr Asn Trp Asn Tyr Phe Leu Gly Ser Phe
            100              105              110

Asp Tyr Trp Gly Gln Gly Thr Leu Val Thr Val Ser Ser Gly Gly Gly
        115              120              125

Gly Ser Gly Gly Gly Gly Ser Gly Gly Gly Gly Ser Ser Tyr Val Leu
    130              135              140

Thr Gln Pro Pro Ser Val Ser Val Ala Pro Gly Lys Thr Ala Arg Ile
145              150              155              160

Thr Cys Gly Gly Asn Asn Ile Arg Ser Lys Ser Val His Trp Tyr Gln
            165              170              175

Gln Lys Pro Gly Gln Ala Pro Val Val Val Ile Tyr Tyr Asp Ser Asp
            180              185              190

Arg Pro Ser Gly Ile Pro Glu Arg Ile Ser Gly Ser Asn Ser Gly Asn
            195              200              205

Thr Ala Thr Leu Thr Ile Ser Arg Val Glu Ala Gly Asp Glu Ala Asp
    210              215              220

Tyr Phe Cys Gln Val Trp Asp Ser Ser Ser Asp His His Val Phe Gly
225              230              235              240

Gly Gly Thr Lys Leu Thr Val Leu
            245

<210> SEQ ID NO 23
<211> LENGTH: 248
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"

<400> SEQUENCE: 23

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Arg Ser Lys Ser Val
            20                  25                  30

His Trp Tyr Gln Gln Lys Pro Gly Gln Ala Pro Val Val Val Ile Tyr
        35                  40                  45

Tyr Asp Ser Asp Arg Pro Ser Gly Ile Pro Glu Arg Ile Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Phe Cys Gln Val Trp Asp Ser Ser Ser Asp His
            85                  90                  95

His Val Phe Gly Gly Gly Thr Lys Leu Thr Val Leu Gly Gly Gly Gly
        100                 105                 110

Ser Gly Gly Gly Gly Ser Gly Gly Gly Gly Ser Gln Val Gln Leu Val
        115                 120                 125

Gln Ser Gly Ala Glu Val Lys Lys Pro Gly Ser Ser Val Lys Val Ser
    130                 135                 140

Cys Lys Ala Ser Gly Gly Thr Phe Ser Ser Tyr Ala Ile Ser Trp Val
145                 150                 155                 160

Arg Gln Ala Pro Gly Gln Gly Leu Glu Trp Met Gly Gly Ile Ile Pro
            165                 170                 175

Ile Phe Gly Thr Ala Asn Tyr Ala Gln Lys Phe Gln Gly Arg Val Thr
            180                 185                 190

Ile Thr Ala Asp Glu Ser Thr Ser Thr Ala Tyr Met Glu Leu Ser Ser
        195                 200                 205

Leu Arg Ser Glu Asp Thr Ala Val Tyr Tyr Cys Ala Arg Val Asp Arg
    210                 215                 220

Tyr Tyr Asn Trp Asn Tyr Phe Leu Gly Ser Phe Asp Tyr Trp Gly Gln
225                 230                 235                 240

Gly Thr Leu Val Thr Val Ser Ser
            245
```

<210> SEQ ID NO 24
<211> LENGTH: 588
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60
```

-continued

```
Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
        210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Cys Gln Glu Glu Met Thr
            340                 345                 350

Lys Asn Gln Val Ser Leu Trp Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys Gly Gly Gly Gly Ser Gly Gly Gly
            435                 440                 445

Gly Ser Gly Gly Gly Gly Ser Ala Pro Ala Ser Ser Ser Thr Lys Lys
        450                 455                 460

Thr Gln Leu Gln Leu Glu His Leu Leu Leu Asp Leu Gln Met Ile Leu
465                 470                 475                 480

Asn Gly Ile Asn Asn Tyr Lys Asn Pro Lys Leu Thr Ser Met Leu Thr
```

```
                        485                 490                 495

Ala Lys Phe Ala Met Pro Lys Lys Ala Thr Glu Leu Lys His Leu Gln
                500                 505                 510

Cys Leu Glu Glu Ala Leu Lys Pro Leu Glu Glu Val Leu Asn Leu Ala
                515                 520                 525

Gln Ser Lys Asn Phe His Leu Arg Pro Arg Asp Leu Ile Ser Asn Ile
            530                 535                 540

Asn Val Ile Val Leu Glu Leu Lys Gly Ser Glu Thr Thr Phe Met Cys
545                 550                 555                 560

Glu Tyr Ala Asp Glu Thr Ala Thr Ile Val Glu Phe Leu Asn Arg Trp
                565                 570                 575

Ile Thr Phe Ser Gln Ser Ile Ile Ser Thr Leu Thr
                580                 585

<210> SEQ ID NO 25
<211> LENGTH: 675
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
        210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255
```

Val Asp Val Ser Gln Glu Asp Pro Glu Val Gln Phe Asn Trp Tyr Val
            260                     265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Gly
305                     310                 315                 320

Leu Pro Ser Ser Ile Glu Lys Thr Ile Ser Lys Ala Lys Gly Gln Pro
                325                 330                 335

Arg Glu Pro Gln Val Cys Thr Leu Pro Pro Ser Gln Glu Glu Met Thr
            340                 345                 350

Lys Asn Gln Val Ser Leu Ser Cys Ala Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Val
385                     390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys Gly Gly Gly Ser Gly Pro Leu
            435                 440                 445

Gly Val Arg Gly Gly Gly Ser Gly Gly Gly Ser Ala Val Asn
            450                 455                 460

Gly Thr Ser Gln Phe Thr Cys Phe Tyr Asn Ser Arg Ala Asn Ile Ser
465                     470                 475                 480

Cys Val Trp Ser Gln Asp Gly Ala Leu Gln Asp Thr Ser Cys Gln Val
                485                 490                 495

His Ala Trp Pro Asp Arg Arg Arg Trp Asn Gln Thr Cys Glu Leu Leu
            500                 505                 510

Pro Val Ser Gln Ala Ser Trp Ala Cys Asn Leu Ile Leu Gly Ala Pro
            515                 520                 525

Asp Ser Gln Lys Leu Thr Thr Val Asp Ile Val Thr Leu Arg Val Leu
            530                 535                 540

Cys Arg Glu Gly Val Arg Trp Arg Val Met Ala Ile Gln Asp Phe Lys
545                     550                 555                 560

Pro Phe Glu Asn Leu Arg Leu Met Ala Pro Ile Ser Leu Gln Val Val
                565                 570                 575

His Val Glu Thr His Arg Cys Asn Ile Ser Trp Glu Ile Ser Gln Ala
            580                 585                 590

Ser His Tyr Phe Glu Arg His Leu Glu Phe Glu Ala Arg Thr Leu Ser
            595                 600                 605

Pro Gly His Thr Trp Glu Glu Ala Pro Leu Leu Thr Leu Lys Gln Lys
            610                 615                 620

Gln Glu Trp Ile Cys Leu Glu Thr Leu Thr Pro Asp Thr Gln Tyr Glu
625                     630                 635                 640

Phe Gln Val Arg Val Lys Pro Leu Gln Gly Glu Phe Thr Thr Trp Ser
                645                 650                 655

Pro Trp Ser Gln Pro Leu Ala Phe Arg Thr Lys Pro Ala Ala Leu Gly
            660                 665                 670

```
Lys Asp Thr
        675

<210> SEQ ID NO 26
<211> LENGTH: 692
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Met Gly Val Lys Val Leu Phe Ala Leu Ile Cys Ile Ala Val Ala Glu
1               5                   10                  15

Ala Gln Val Gln Leu Val Glu Ser Gly Gly Gly Val Val Gln Pro Gly
                20                  25                  30

Arg Ser Leu Arg Leu Asp Cys Lys Ala Ser Gly Ile Thr Phe Ser Asn
            35                  40                  45

Ser Gly Met His Trp Val Arg Gln Ala Pro Gly Lys Gly Leu Glu Trp
        50                  55                  60

Val Ala Val Ile Trp Tyr Asp Gly Ser Lys Arg Tyr Tyr Ala Asp Ser
65                  70                  75                  80

Val Lys Gly Arg Phe Thr Ile Ser Arg Asp Asn Ser Lys Asn Thr Leu
                85                  90                  95

Phe Leu Gln Met Asn Ser Leu Arg Ala Glu Asp Thr Ala Val Tyr Tyr
                100                 105                 110

Cys Ala Thr Asn Asp Asp Tyr Trp Gly Gln Gly Thr Leu Val Thr Val
            115                 120                 125

Ser Ser Ala Ser Thr Lys Gly Pro Ser Val Phe Pro Leu Ala Pro Cys
        130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
        210                 215                 220

Asp Lys Arg Val Glu Ser Lys Tyr Gly Pro Pro Cys Pro Pro Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
            275                 280                 285

Val Asp Gly Val Glu Val His Asn Ala Lys Thr Lys Pro Arg Glu Glu
        290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
```

```
                340                 345                 350

Pro Arg Glu Pro Gln Val Tyr Thr Leu Pro Pro Ser Gln Glu Glu Met
            355             360             365

Thr Lys Asn Gln Val Ser Leu Thr Cys Leu Val Lys Gly Phe Tyr Pro
        370             375             380

Ser Asp Ile Ala Val Glu Trp Glu Ser Asn Gly Gln Pro Glu Asn Asn
385                 390             395                 400

Tyr Lys Thr Thr Pro Pro Val Leu Asp Ser Asp Gly Ser Phe Phe Leu
            405             410             415

Tyr Ser Arg Leu Thr Val Asp Lys Ser Arg Trp Gln Glu Gly Asn Val
            420             425             430

Phe Ser Cys Ser Val Met His Glu Ala Leu His Asn His Tyr Thr Gln
            435             440             445

Lys Ser Leu Ser Leu Ser Leu Gly Ala Gly Gly Gly Ser Gly Gly
        450             455             460

Gly Gly Ser Ala Ala Gly Gly Gly Gly Ser Gly Gly Gly Gly Ser Cys
465                 470             475                 480

Pro Asp Leu Val Cys Tyr Thr Asp Tyr Leu Gln Thr Val Ile Cys Ile
            485             490             495

Leu Glu Met Trp Asn Leu His Pro Ser Thr Leu Thr Leu Thr Trp Gln
            500             505             510

Asp Gln Tyr Glu Glu Leu Lys Asp Glu Ala Thr Ser Cys Ser Leu His
            515             520             525

Arg Ser Ala His Asn Ala Thr His Ala Thr Tyr Thr Cys His Met Asp
        530             535             540

Val Phe His Phe Met Ala Asp Asp Ile Phe Ser Val Asn Ile Thr Asp
545                 550             555                 560

Gln Ser Gly Asn Tyr Ser Gln Glu Cys Gly Ser Phe Leu Leu Ala Glu
            565             570             575

Ser Ile Lys Pro Ala Pro Pro Phe Asn Val Thr Val Thr Phe Ser Gly
            580             585             590

Gln Tyr Asn Ile Ser Trp Arg Ser Asp Tyr Glu Asp Pro Ala Phe Tyr
            595             600             605

Met Leu Lys Gly Lys Leu Gln Tyr Glu Leu Gln Tyr Arg Asn Arg Gly
        610             615             620

Asp Pro Trp Ala Val Ser Pro Arg Arg Lys Leu Ile Ser Val Asp Ser
625                 630             635                 640

Arg Ser Val Ser Leu Leu Pro Leu Glu Phe Arg Lys Asp Ser Ser Tyr
            645             650             655

Glu Leu Gln Val Arg Ala Gly Pro Met Pro Gly Ser Ser Tyr Gln Gly
            660             665             670

Thr Trp Ser Glu Trp Ser Asp Pro Val Ile Phe Gln Thr Gln Ser Glu
        675             680             685

Glu Leu Lys Glu
    690
```

```
<210> SEQ ID NO 27
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
```

```
<222> LOCATION: (1)..(20)
<223> OTHER INFORMATION: /note="This sequence may encompass 1-4 'Gly Gly
      Gly Gly Ser' repeating units"

<400> SEQUENCE: 27

Gly Gly Gly Gly Ser Gly Gly Gly Gly Ser Gly Gly Gly Gly Ser Gly
1               5                   10                  15

Gly Gly Gly Ser
            20

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Gly Gly Gly Ser
1               5

<210> SEQ ID NO 29
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Gly Gly Gly Ser Gly Gly Gly Gly Ser
1               5                   10

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (11)..(12)
<223> OTHER INFORMATION: /replace="N"
<220> FEATURE:
<221> NAME/KEY: SITE
<222> LOCATION: (1)..(22)
<223> OTHER INFORMATION: /note="Variant residues given in the sequence
      have no preference with respect to those in the annotations
      for variant positions"

<400> SEQUENCE: 31
```

-continued

```
Gly Gly Gly Gly Ser Gly Gly Gly Gly Ser Ala Ala Gly Gly Gly Gly
1               5                   10                  15

Ser Gly Gly Gly Gly Ser
            20
```

```
<210> SEQ ID NO 32
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (16)..(17)
<223> OTHER INFORMATION: /replace="N"
<220> FEATURE:
<221> NAME/KEY: SITE
<222> LOCATION: (1)..(27)
<223> OTHER INFORMATION: /note="Variant residues given in the sequence
      have no preference with respect to those in the annotations
      for variant positions"

<400> SEQUENCE: 32

Gly Gly Gly Gly Ser Gly Gly Gly Gly Ser Gly Gly Gly Gly Ser Ala
1               5                   10                  15

Ala Gly Gly Gly Gly Ser Gly Gly Gly Gly Ser
            20                  25
```

```
<210> SEQ ID NO 33
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (16)..(17)
<223> OTHER INFORMATION: /replace="N"
<220> FEATURE:
<221> NAME/KEY: SITE
<222> LOCATION: (1)..(32)
<223> OTHER INFORMATION: /note="Variant residues given in the sequence
      have no preference with respect to those in the annotations
      for variant positions"

<400> SEQUENCE: 33

Gly Gly Gly Gly Ser Gly Gly Gly Gly Ser Gly Gly Gly Gly Ser Ala
1               5                   10                  15

Ala Gly Gly Gly Gly Ser Gly Gly Gly Gly Ser Gly Gly Gly Gly Ser
            20                  25                  30
```

```
<210> SEQ ID NO 34
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (10)..(10)
<223> OTHER INFORMATION: /replace="A" or "N"
<220> FEATURE:
<221> NAME/KEY: VARIANT
<222> LOCATION: (15)..(15)
<223> OTHER INFORMATION: /replace="N"
```

```
<220> FEATURE:
<221> NAME/KEY: SITE
<222> LOCATION: (1)..(20)
<223> OTHER INFORMATION: /note="Variant residues given in the sequence
      have no preference with respect to those in the annotations
      for variant positions"

<400> SEQUENCE: 34

Gly Gly Gly Gly Ser Gly Gly Gly Gly Ser Gly Gly Gly Gly Ala Gly
1               5                   10                  15

Gly Gly Gly Ser
            20

<210> SEQ ID NO 35
<211> LENGTH: 604
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (440)..(454)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (455)..(455)
<223> OTHER INFORMATION: /replace=" "
<220> FEATURE:
<221> NAME/KEY: VARIANT
<222> LOCATION: (456)..(456)
<223> OTHER INFORMATION: /replace=" "
<220> FEATURE:
<221> NAME/KEY: SITE
<222> LOCATION: (457)..(471)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (474)..(474)
<223> OTHER INFORMATION: /replace="A"
<220> FEATURE:
<221> NAME/KEY: VARIANT
<222> LOCATION: (506)..(506)
<223> OTHER INFORMATION: /replace="N"
<220> FEATURE:
<221> NAME/KEY: VARIANT
<222> LOCATION: (513)..(513)
<223> OTHER INFORMATION: /replace="G" or "S" or "T" or "Q" or "E" or "N"
      or "D" or "R" or "K"
<220> FEATURE:
<221> NAME/KEY: VARIANT
<222> LOCATION: (516)..(516)
<223> OTHER INFORMATION: /replace="G" or "S" or "T" or "Q" or "E" or "N"
      or "D" or "R" or "K"
<220> FEATURE:
<221> NAME/KEY: VARIANT
<222> LOCATION: (543)..(543)
<223> OTHER INFORMATION: /replace="G" or "S" or "T" or "Q" or "E" or "N"
      or "D" or "R" or "K"
<220> FEATURE:
<221> NAME/KEY: VARIANT
<222> LOCATION: (544)..(544)
<223> OTHER INFORMATION: /replace="T"
<220> FEATURE:
<221> NAME/KEY: VARIANT
<222> LOCATION: (596)..(596)
<223> OTHER INFORMATION: /replace="S"
<220> FEATURE:
<221> NAME/KEY: SITE
<222> LOCATION: (1)..(604)
<223> OTHER INFORMATION: /note="Variant residues given in the sequence
      have no preference with respect to those in the annotations
      for variant positions"
```

-continued

<400> SEQUENCE: 35

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe

-continued

```
                    405                410                415
Ser Cys Ser Val Met His Glu Ala Leu His Asn His Tyr Thr Gln Lys
            420                425                430

Ser Leu Ser Leu Ser Leu Ala Gly Gly Gly Gly Ser Gly Gly Gly Gly
        435                440                445

Ser Gly Gly Gly Gly Ser Ala Ala Gly Gly Gly Gly Ser Gly Gly Gly
    450                455                460

Gly Ser Gly Gly Gly Gly Ser Ala Pro Asn Ser Ser Ser Thr Lys Lys
465                470                475                480

Thr Gln Leu Gln Leu Glu His Leu Leu Leu Asp Leu Gln Met Ile Leu
            485                490                495

Asn Gly Ile Asn Asn Tyr Lys Asn Pro Lys Leu Thr Arg Met Leu Thr
            500                505                510

Ala Lys Phe Ala Met Pro Lys Lys Ala Thr Glu Leu Lys His Leu Gln
        515                520                525

Cys Leu Glu Glu Glu Leu Lys Pro Leu Glu Glu Val Leu Asn Ala Ala
    530                535                540

Gln Ser Lys Asn Phe His Leu Arg Pro Arg Asp Leu Ile Ser Asn Ile
545                550                555                560

Asn Val Ile Val Leu Glu Leu Lys Gly Ser Glu Thr Thr Phe Met Cys
            565                570                575

Glu Tyr Ala Asp Glu Thr Ala Thr Ile Val Glu Phe Leu Asn Arg Trp
        580                585                590

Ile Thr Phe Ala Gln Ser Ile Ile Ser Thr Leu Thr
        595                600
```

<210> SEQ ID NO 36
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (441)..(455)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (456)..(456)
<223> OTHER INFORMATION: /replace=" "
<220> FEATURE:
<221> NAME/KEY: VARIANT
<222> LOCATION: (457)..(457)
<223> OTHER INFORMATION: /replace=" "
<220> FEATURE:
<221> NAME/KEY: SITE
<222> LOCATION: (458)..(472)
<223> OTHER INFORMATION: /note="This region may encompass 0-3 'Gly Gly
      Gly Gly Ser' repeating units"
<220> FEATURE:
<221> NAME/KEY: SITE
<222> LOCATION: (1)..(686)
<223> OTHER INFORMATION: /note="Variant residues given in the sequence
      have no preference with respect to those in the annotations
      for variant positions"

<400> SEQUENCE: 36

```
Gln Val Gln Leu Val Glu Ser Gly Gly Gly Val Val Gln Pro Gly Arg
1                5                10                15

Ser Leu Arg Leu Asp Cys Lys Ala Ser Gly Ile Thr Phe Ser Asn Ser
            20                25                30
```

```
Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                      70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
                180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
        210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Ala Gly Gly Gly Ser Gly Gly Gly
        435                 440                 445
```

```
Gly Ser Gly Gly Gly Gly Ser Ala Ala Gly Gly Gly Gly Ser Gly Gly
    450                 455                 460

Gly Gly Ser Gly Gly Gly Gly Ser Ala Val Asn Gly Thr Ser Gln Phe
465                 470                 475                 480

Thr Cys Phe Tyr Asn Ser Arg Ala Asn Ile Ser Cys Val Trp Ser Gln
                485                 490                 495

Asp Gly Ala Leu Gln Asp Thr Ser Cys Gln Val His Ala Trp Pro Asp
                500                 505                 510

Arg Arg Arg Trp Asn Gln Thr Cys Glu Leu Leu Pro Val Ser Gln Ala
                515                 520                 525

Ser Trp Ala Cys Asn Leu Ile Leu Gly Ala Pro Asp Ser Gln Lys Leu
    530                 535                 540

Thr Thr Val Asp Ile Val Thr Leu Arg Val Leu Cys Arg Glu Gly Val
545                 550                 555                 560

Arg Trp Arg Val Met Ala Ile Gln Asp Phe Lys Pro Phe Glu Asn Leu
                565                 570                 575

Arg Leu Met Ala Pro Ile Ser Leu Gln Val Val His Val Glu Thr His
                580                 585                 590

Arg Cys Asn Ile Ser Trp Glu Ile Ser Gln Ala Ser His Tyr Phe Glu
                595                 600                 605

Arg His Leu Glu Phe Glu Ala Arg Thr Leu Ser Pro Gly His Thr Trp
                610                 615                 620

Glu Glu Ala Pro Leu Leu Thr Leu Lys Gln Lys Gln Glu Trp Ile Cys
625                 630                 635                 640

Leu Glu Thr Leu Thr Pro Asp Thr Gln Tyr Glu Phe Gln Val Arg Val
                645                 650                 655

Lys Pro Leu Gln Gly Glu Phe Thr Thr Trp Ser Pro Trp Ser Gln Pro
                660                 665                 670

Leu Ala Phe Arg Thr Lys Pro Ala Ala Leu Gly Lys Asp Thr
                675                 680                 685
```

```
<210> SEQ ID NO 37
<211> LENGTH: 665
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37
```

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
```

```
                115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
                180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Ala Gly Gly Gly Ser Gly Gly Gly
            435                 440                 445

Gly Ser Gly Gly Gly Gly Ser Ile Thr Cys Pro Pro Pro Met Ser Val
    450                 455                 460

Glu His Ala Asp Ile Trp Val Lys Ser Tyr Ser Leu Tyr Ser Arg Glu
465                 470                 475                 480

Arg Tyr Ile Cys Asn Ser Gly Phe Lys Arg Lys Ala Gly Thr Ser Ser
                485                 490                 495

Leu Thr Glu Cys Val Leu Asn Lys Ala Thr Asn Val Ala His Trp Thr
                500                 505                 510

Thr Pro Ser Leu Lys Cys Ile Arg Gly Gly Gly Gly Ser Gly Gly Gly
            515                 520                 525

Ser Gly Gly Gly Gly Ser Ala Ala Gly Gly Gly Gly Ser Gly Gly Gly
    530                 535                 540
```

```
Gly Ser Gly Gly Gly Gly Ser Asn Trp Val Asn Val Ile Ser Asp Leu
545                 550                 555                 560

Lys Lys Ile Glu Asp Leu Ile Gln Ser Met His Ile Asp Ala Thr Leu
                565                 570                 575

Tyr Thr Glu Ser Asp Val His Pro Ser Cys Lys Val Thr Ala Met Lys
                580                 585                 590

Cys Phe Leu Leu Glu Leu Gln Val Ile Ser Leu Glu Ser Gly Asp Ala
            595                 600                 605

Ser Ile His Asp Thr Val Glu Asp Leu Ile Ile Leu Ala Asn Asn Ser
        610                 615                 620

Leu Ser Ser Asn Gly Asn Val Thr Glu Ser Gly Cys Lys Glu Cys Glu
625                 630                 635                 640

Glu Leu Glu Glu Lys Asn Ile Lys Glu Phe Leu Gln Ser Phe Val His
                645                 650                 655

Ile Val Gln Met Phe Ile Asn Thr Ser
                660                 665
```

```
<210> SEQ ID NO 38
<211> LENGTH: 712
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (441)..(455)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (456)..(456)
<223> OTHER INFORMATION: /replace=" "
<220> FEATURE:
<221> NAME/KEY: VARIANT
<222> LOCATION: (457)..(457)
<223> OTHER INFORMATION: /replace=" "
<220> FEATURE:
<221> NAME/KEY: SITE
<222> LOCATION: (458)..(472)
<223> OTHER INFORMATION: /note="This region may encompass 0-3 'Gly Gly
      Gly Gly Ser' repeating units"
<220> FEATURE:
<221> NAME/KEY: SITE
<222> LOCATION: (1)..(712)
<223> OTHER INFORMATION: /note="Variant residues given in the sequence
      have no preference with respect to those in the annotations
      for variant positions"

<400> SEQUENCE: 38
```

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95
```

```
Ala Thr Asn Asp Asp Tyr Trp Gly Gln Gly Thr Leu Val Thr Val Ser
        100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
            435                 440                 445

Gly Ser Gly Gly Gly Gly Ser Ala Ala Gly Gly Gly Ser Gly Gly
        450                 455                 460

Gly Gly Ser Gly Gly Gly Gly Ser Glu Ile Val Leu Thr Gln Ser Pro
465                 470                 475                 480

Gly Thr Leu Ser Leu Ser Pro Gly Glu Arg Ala Thr Leu Ser Cys Arg
                485                 490                 495

Ala Ser Gln Ser Val Ser Ser Ser Tyr Leu Ala Trp Tyr Gln Gln Lys
            500                 505                 510

Pro Gly Gln Ala Pro Arg Leu Leu Ile Tyr Gly Ala Ser Arg Arg Ala
```

```
                  515                   520                   525

Thr Gly Ile Pro Asp Arg Phe Ser Gly Ser Gly Ser Gly Thr Asp Phe
    530                   535                   540

Thr Leu Thr Ile Ser Arg Leu Glu Pro Glu Asp Phe Ala Val Tyr Tyr
545                   550                   555                   560

Cys Gln Arg Tyr Gly Ser Ser His Thr Phe Gly Gln Gly Thr Lys Leu
                565                   570                   575

Glu Ile Ser Gly Gly Gly Gly Ser Gly Gly Gly Ser Gly Gly Gly
                580                   585                   590

Gly Ser Glu Val Gln Leu Val Gln Ser Gly Ala Glu Val Lys Lys Pro
                595                   600                   605

Gly Glu Ser Leu Lys Ile Ser Cys Lys Val Ser Gly Tyr Phe Phe Thr
    610                   615                   620

Thr Tyr Trp Ile Gly Trp Val Arg Gln Met Pro Gly Lys Gly Leu Glu
625                   630                   635                   640

Tyr Met Gly Ile Ile Tyr Pro Gly Asp Ser Asp Thr Arg Tyr Ser Pro
                645                   650                   655

Ser Phe Gln Gly Gln Val Thr Ile Ser Ala Asp Lys Ser Ile Ser Thr
                660                   665                   670

Ala Tyr Leu Gln Trp Ser Ser Leu Lys Ala Ser Asp Thr Ala Met Tyr
                675                   680                   685

Tyr Cys Ala Arg Gly Gly Asn Trp Asn Cys Phe Asp Tyr Trp Gly Gln
    690                   695                   700

Gly Thr Leu Val Thr Val Ser Ser
705                   710
```

```
<210> SEQ ID NO 39
<211> LENGTH: 605
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Met Gly Val Lys Val Leu Phe Ala Leu Ile Cys Ile Ala Val Ala Glu
1               5                   10                  15

Ala Gln Val Gln Leu Val Glu Ser Gly Gly Gly Val Val Gln Pro Gly
                20                  25                  30

Arg Ser Leu Arg Leu Asp Cys Lys Ala Ser Gly Ile Thr Phe Ser Asn
            35                  40                  45

Ser Gly Met His Trp Val Arg Gln Ala Pro Gly Lys Gly Leu Glu Trp
    50                  55                  60

Val Ala Val Ile Trp Tyr Asp Gly Ser Lys Arg Tyr Tyr Ala Asp Ser
65                  70                  75                  80

Val Lys Gly Arg Phe Thr Ile Ser Arg Asp Asn Ser Lys Asn Thr Leu
            85                  90                  95

Phe Leu Gln Met Asn Ser Leu Arg Ala Glu Asp Thr Ala Val Tyr Tyr
            100                 105                 110

Cys Ala Thr Asn Asp Asp Tyr Trp Gly Gln Gly Thr Leu Val Thr Val
            115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160
```

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
                180                 185                 190

Tyr Ser Leu Ser Ser Val Val Thr Val Pro Ser Ser Ser Leu Gly Thr
            195                 200                 205

Lys Thr Tyr Thr Cys Asn Val Asp His Lys Pro Ser Asn Thr Lys Val
        210                 215                 220

Asp Lys Arg Val Glu Ser Lys Tyr Gly Pro Pro Cys Pro Pro Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
                260                 265                 270

Val Val Asp Val Ser Gln Glu Asp Pro Glu Val Gln Phe Asn Trp Tyr
            275                 280                 285

Val Asp Gly Val Glu Val His Asn Ala Lys Thr Lys Pro Arg Glu Glu
        290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
                340                 345                 350

Pro Arg Glu Pro Gln Val Tyr Thr Leu Pro Pro Ser Gln Glu Glu Met
            355                 360                 365

Thr Lys Asn Gln Val Ser Leu Thr Cys Leu Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
            435                 440                 445

Lys Ser Leu Ser Leu Ser Leu Gly Ala Gly Gly Gly Ser Gly Gly
        450                 455                 460

Gly Gly Ser Gly Gly Gly Gly Ser Gln Gly Gln Asp Arg His Met Ile
465                 470                 475                 480

Arg Met Arg Gln Leu Ile Asp Ile Val Asp Gln Leu Lys Asn Tyr Val
                485                 490                 495

Asn Asp Leu Val Pro Glu Phe Leu Pro Ala Pro Glu Asp Val Glu Thr
            500                 505                 510

Asn Cys Glu Trp Ser Ala Phe Ser Cys Phe Gln Lys Ala Gln Leu Lys
            515                 520                 525

Ser Ala Asn Thr Gly Asn Asn Glu Arg Ile Ile Asn Val Ser Ile Lys
        530                 535                 540

Lys Leu Lys Arg Lys Pro Pro Ser Thr Asn Ala Gly Arg Arg Gln Lys
545                 550                 555                 560

His Arg Leu Thr Cys Pro Ser Cys Asp Ser Tyr Glu Lys Lys Pro Pro
                565                 570                 575

-continued

```
Lys Glu Phe Leu Glu Arg Phe Lys Ser Leu Leu Gln Lys Met Ile His
            580                 585                 590

Gln His Leu Ser Ser Arg Thr His Gly Ser Glu Asp Ser
        595                 600                 605

<210> SEQ ID NO 40
<211> LENGTH: 691
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Met Gly Val Lys Val Leu Phe Ala Leu Ile Cys Ile Ala Val Ala Glu
1               5                   10                  15

Ala Gln Val Gln Leu Val Glu Ser Gly Gly Gly Val Val Gln Pro Gly
                20                  25                  30

Arg Ser Leu Arg Leu Asp Cys Lys Ala Ser Gly Ile Thr Phe Ser Asn
        35                  40                  45

Ser Gly Met His Trp Val Arg Gln Ala Pro Gly Lys Gly Leu Glu Trp
    50                  55                  60

Val Ala Val Ile Trp Tyr Asp Gly Ser Lys Arg Tyr Tyr Ala Asp Ser
65                  70                  75                  80

Val Lys Gly Arg Phe Thr Ile Ser Arg Asp Asn Ser Lys Asn Thr Leu
                85                  90                  95

Phe Leu Gln Met Asn Ser Leu Arg Ala Glu Asp Thr Ala Val Tyr Tyr
            100                 105                 110

Cys Ala Thr Asn Asp Asp Tyr Trp Gly Gln Gly Thr Leu Val Thr Val
        115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Pro Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
            275                 280                 285

Val Asp Gly Val Glu Val His Asn Ala Lys Thr Lys Pro Arg Glu Glu
        290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
```

-continued

```
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
            355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
            435                 440                 445

Lys Ser Leu Ser Leu Ser Leu Gly Ala Gly Gly Gly Gly Ser Gly Gly
            450                 455                 460

Gly Gly Ser Gly Pro Leu Gly Val Arg Gly Gly Gly Gly Ser Cys Pro
465                 470                 475                 480

Asp Leu Val Cys Tyr Thr Asp Tyr Leu Gln Thr Val Ile Cys Ile Leu
                485                 490                 495

Glu Met Trp Asn Leu His Pro Ser Thr Leu Thr Leu Thr Trp Gln Asp
            500                 505                 510

Gln Tyr Glu Glu Leu Lys Asp Glu Ala Thr Ser Cys Ser Leu His Arg
            515                 520                 525

Ser Ala His Asn Ala Thr His Ala Thr Tyr Thr Cys His Met Asp Val
            530                 535                 540

Phe His Phe Met Ala Asp Asp Ile Phe Ser Val Asn Ile Thr Asp Gln
545                 550                 555                 560

Ser Gly Asn Tyr Ser Gln Glu Cys Gly Ser Phe Leu Leu Ala Glu Ser
                565                 570                 575

Ile Lys Pro Ala Pro Pro Phe Asn Val Thr Val Thr Phe Ser Gly Gln
            580                 585                 590

Tyr Asn Ile Ser Trp Arg Ser Asp Tyr Glu Asp Pro Ala Phe Tyr Met
            595                 600                 605

Leu Lys Gly Lys Leu Gln Tyr Glu Leu Gln Tyr Arg Asn Arg Gly Asp
            610                 615                 620

Pro Trp Ala Val Ser Pro Arg Arg Lys Leu Ile Ser Val Asp Ser Arg
625                 630                 635                 640

Ser Val Ser Leu Leu Pro Leu Glu Phe Arg Lys Asp Ser Ser Tyr Glu
                645                 650                 655

Leu Gln Val Arg Ala Gly Pro Met Pro Gly Ser Ser Tyr Gln Gly Thr
            660                 665                 670

Trp Ser Glu Trp Ser Asp Pro Val Ile Phe Gln Thr Gln Ser Glu Glu
            675                 680                 685

Leu Lys Glu
    690
```

<210> SEQ ID NO 41
<211> LENGTH: 726
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 41

```
Met Gly Val Lys Val Leu Phe Ala Leu Ile Cys Ile Ala Val Ala Glu
1               5                   10                  15

Ala Gln Val Gln Leu Val Glu Ser Gly Gly Gly Val Val Gln Pro Gly
                20                  25                  30

Arg Ser Leu Arg Leu Asp Cys Lys Ala Ser Gly Ile Thr Phe Ser Asn
            35                  40                  45

Ser Gly Met His Trp Val Arg Gln Ala Pro Gly Lys Gly Leu Glu Trp
        50                  55                  60

Val Ala Val Ile Trp Tyr Asp Gly Ser Lys Arg Tyr Tyr Ala Asp Ser
65                  70                  75                  80

Val Lys Gly Arg Phe Thr Ile Ser Arg Asp Asn Ser Lys Asn Thr Leu
                85                  90                  95

Phe Leu Gln Met Asn Ser Leu Arg Ala Glu Asp Thr Ala Val Tyr Tyr
                100                 105                 110

Cys Ala Thr Asn Asp Asp Tyr Trp Gly Gln Gly Thr Leu Val Thr Val
            115                 120                 125

Ser Ser Ala Ser Thr Lys Gly Pro Ser Val Phe Pro Leu Ala Pro Cys
        130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
            195                 200                 205

Lys Thr Tyr Thr Cys Asn Val Asp His Lys Pro Ser Asn Thr Lys Val
        210                 215                 220

Asp Lys Arg Val Glu Ser Lys Tyr Gly Pro Pro Cys Pro Pro Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
            275                 280                 285

Val Asp Gly Val Glu Val His Asn Ala Lys Thr Lys Pro Arg Glu Glu
        290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400
```

```
Tyr Lys Thr Thr Pro Pro Val Leu Asp Ser Asp Gly Ser Phe Phe Leu
            405             410             415

Tyr Ser Arg Leu Thr Val Asp Lys Ser Arg Trp Gln Glu Gly Asn Val
            420             425             430

Phe Ser Cys Ser Val Met His Glu Ala Leu His Asn His Tyr Thr Gln
            435             440             445

Lys Ser Leu Ser Leu Ser Leu Gly Ala Gly Gly Gly Ser Gly Gly
    450             455             460

Gly Gly Ser Ala Ala Gly Gly Gly Ser Gly Gly Gly Ser Glu
465             470             475             480

Ile Val Leu Thr Gln Ser Pro Gly Thr Leu Ser Leu Ser Pro Gly Glu
            485             490             495

Arg Ala Thr Leu Ser Cys Arg Ala Ser Gln Ser Val Ser Ser Ser Tyr
            500             505             510

Leu Ala Trp Tyr Gln Gln Lys Pro Gly Gln Ala Pro Arg Leu Leu Ile
            515             520             525

Tyr Gly Ala Ser Ser Arg Ala Thr Gly Ile Pro Asp Arg Phe Ser Gly
    530             535             540

Ser Gly Ser Gly Thr Asp Phe Thr Leu Thr Ile Ser Arg Leu Glu Pro
545             550             555             560

Glu Asp Phe Ala Val Tyr Tyr Cys Gln Gln Tyr Gly Ser Trp Thr Phe
            565             570             575

Gly Gln Gly Thr Lys Val Glu Ile Lys Gly Gly Gly Ser Gly Gly
            580             585             590

Gly Gly Ser Gly Gly Gly Ser Gln Val Gln Leu Val Glu Ser Gly
            595             600             605

Gly Gly Val Val Gln Pro Gly Arg Ser Leu Arg Leu Ser Cys Ala Ala
    610             615             620

Ser Gly Phe Thr Phe Ser Ser Tyr Gly Met His Trp Val Arg Gln Ala
625             630             635             640

Pro Gly Lys Gly Leu Glu Trp Val Ala Phe Ile Trp Tyr Asp Gly Ser
            645             650             655

Asp Lys Tyr Tyr Ala Asp Ser Val Lys Gly Arg Phe Thr Ile Ser Arg
            660             665             670

Asp Asn Ser Lys Asn Thr Leu Tyr Leu Gln Met Asn Ser Leu Arg Ala
            675             680             685

Glu Asp Thr Ala Val Tyr Tyr Cys Ala Arg Asp Gly Asp Ser Ser Asp
            690             695             700

Trp Tyr Gly Asp Tyr Tyr Phe Gly Met Asp Val Trp Gly Gln Gly Thr
705             710             715             720

Thr Val Thr Val Ser Ser
            725
```

<210> SEQ ID NO 42
<211> LENGTH: 588
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

```
Gln Val Gln Leu Val Glu Ser Gly Gly Gly Val Val Gln Pro Gly Arg
1               5               10              15

Ser Leu Arg Leu Asp Cys Lys Ala Ser Gly Ile Thr Phe Ser Asn Ser
```

-continued

```
                20                    25                    30
Gly Met His Trp Val Arg Gln Ala Pro Gly Lys Gly Leu Glu Trp Val
            35                    40                    45
Ala Val Ile Trp Tyr Asp Gly Ser Lys Arg Tyr Tyr Ala Asp Ser Val
        50                    55                    60
Lys Gly Arg Phe Thr Ile Ser Arg Asp Asn Ser Lys Asn Thr Leu Phe
65                    70                    75                    80
Leu Gln Met Asn Ser Leu Arg Ala Glu Asp Thr Ala Val Tyr Tyr Cys
                85                    90                    95
Ala Thr Asn Asp Asp Tyr Trp Gly Gln Gly Thr Leu Val Thr Val Ser
                100                   105                   110
Ser Ala Ser Thr Lys Gly Pro Ser Val Phe Pro Leu Ala Pro Cys Ser
            115                   120                   125
Arg Ser Thr Ser Glu Ser Thr Ala Ala Leu Gly Cys Leu Val Lys Asp
        130                   135                   140
Tyr Phe Pro Glu Pro Val Thr Val Ser Trp Asn Ser Gly Ala Leu Thr
145                   150                   155                   160
Ser Gly Val His Thr Phe Pro Ala Val Leu Gln Ser Ser Gly Leu Tyr
                165                   170                   175
Ser Leu Ser Ser Val Val Thr Val Pro Ser Ser Ser Leu Gly Thr Lys
            180                   185                   190
Thr Tyr Thr Cys Asn Val Asp His Lys Pro Ser Asn Thr Lys Val Asp
            195                   200                   205
Lys Arg Val Glu Ser Lys Tyr Gly Pro Pro Cys Pro Pro Cys Pro Ala
        210                   215                   220
Pro Glu Phe Leu Gly Gly Pro Ser Val Phe Leu Phe Pro Pro Lys Pro
225                   230                   235                   240
Lys Asp Thr Leu Met Ile Ser Arg Thr Pro Glu Val Thr Cys Val Val
                245                   250                   255
Val Asp Val Ser Gln Glu Asp Pro Glu Val Gln Phe Asn Trp Tyr Val
                260                   265                   270
Asp Gly Val Glu Val His Asn Ala Lys Thr Lys Pro Arg Glu Glu Gln
            275                   280                   285
Phe Asn Ser Thr Tyr Arg Val Val Ser Val Leu Thr Val Leu His Gln
    290                   295                   300
Asp Trp Leu Asn Gly Lys Glu Tyr Lys Cys Lys Val Ser Asn Lys Gly
305                   310                   315                   320
Leu Pro Ser Ser Ile Glu Lys Thr Ile Ser Lys Ala Lys Gly Gln Pro
                325                   330                   335
Arg Glu Pro Gln Val Tyr Thr Leu Pro Pro Cys Gln Glu Glu Met Thr
            340                   345                   350
Lys Asn Gln Val Ser Leu Trp Cys Leu Val Lys Gly Phe Tyr Pro Ser
            355                   360                   365
Asp Ile Ala Val Glu Trp Glu Ser Asn Gly Gln Pro Glu Asn Asn Tyr
        370                   375                   380
Lys Thr Thr Pro Pro Val Leu Asp Ser Asp Gly Ser Phe Phe Leu Tyr
385                   390                   395                   400
Ser Arg Leu Thr Val Asp Lys Ser Arg Trp Gln Glu Gly Asn Val Phe
                405                   410                   415
Ser Cys Ser Val Met His Glu Ala Leu His Asn His Tyr Thr Gln Lys
                420                   425                   430
Ser Leu Ser Leu Ser Leu Gly Ala Gly Gly Gly Ser Gly Gly Gly
            435                   440                   445
```

-continued

```
Gly Ser Gly Gly Gly Gly Ser Gln Gly Gln Asp Arg His Met Ile Arg
    450             455             460

Met Arg Gln Leu Ile Asp Ile Val Asp Gln Leu Lys Asn Tyr Val Asn
465             470             475             480

Asp Leu Val Pro Glu Phe Leu Pro Ala Pro Glu Asp Val Glu Thr Asn
            485             490             495

Cys Glu Trp Ser Ala Phe Ser Cys Phe Gln Lys Ala Gln Leu Lys Ser
            500             505             510

Ala Asn Thr Gly Asn Asn Glu Arg Ile Ile Asn Val Ser Ile Lys Lys
        515             520             525

Leu Lys Arg Lys Pro Pro Ser Thr Asn Ala Gly Arg Arg Gln Lys His
    530             535             540

Arg Leu Thr Cys Pro Ser Cys Asp Ser Tyr Glu Lys Lys Pro Pro Lys
545             550             555             560

Glu Phe Leu Glu Arg Phe Lys Ser Leu Leu Gln Lys Met Ile His Gln
            565             570             575

His Leu Ser Ser Arg Thr His Gly Ser Glu Asp Ser
        580             585

<210> SEQ ID NO 43
<211> LENGTH: 675
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Val Gln Leu Val Glu Ser Gly Gly Gly Val Val Gln Pro Gly Arg
1               5               10              15

Ser Leu Arg Leu Asp Cys Lys Ala Ser Gly Ile Thr Phe Ser Asn Ser
            20              25              30

Gly Met His Trp Val Arg Gln Ala Pro Gly Lys Gly Leu Glu Trp Val
        35              40              45

Ala Val Ile Trp Tyr Asp Gly Ser Lys Arg Tyr Tyr Ala Asp Ser Val
    50              55              60

Lys Gly Arg Phe Thr Ile Ser Arg Asp Asn Ser Lys Asn Thr Leu Phe
65              70              75              80

Leu Gln Met Asn Ser Leu Arg Ala Glu Asp Thr Ala Val Tyr Tyr Cys
            85              90              95

Ala Thr Asn Asp Asp Tyr Trp Gly Gln Gly Thr Leu Val Thr Val Ser
            100             105             110

Ser Ala Ser Thr Lys Gly Pro Ser Val Phe Pro Leu Ala Pro Cys Ser
        115             120             125

Arg Ser Thr Ser Glu Ser Thr Ala Ala Leu Gly Cys Leu Val Lys Asp
    130             135             140

Tyr Phe Pro Glu Pro Val Thr Val Ser Trp Asn Ser Gly Ala Leu Thr
145             150             155             160

Ser Gly Val His Thr Phe Pro Ala Val Leu Gln Ser Ser Gly Leu Tyr
            165             170             175

Ser Leu Ser Ser Val Val Thr Val Pro Ser Ser Ser Leu Gly Thr Lys
        180             185             190

Thr Tyr Thr Cys Asn Val Asp His Lys Pro Ser Asn Thr Lys Val Asp
        195             200             205
```

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
                275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Cys Thr Leu Pro Pro Ser Gln Glu Glu Met Thr
                340                 345                 350

Lys Asn Gln Val Ser Leu Ser Cys Ala Val Lys Gly Phe Tyr Pro Ser
                355                 360                 365

Asp Ile Ala Val Glu Trp Glu Ser Asn Gly Gln Pro Glu Asn Asn Tyr
                370                 375                 380

Lys Thr Thr Pro Pro Val Leu Asp Ser Asp Gly Ser Phe Phe Leu Val
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Ala Gly Gly Gly Ser Gly Gly Gly
                435                 440                 445

Gly Ser Ala Ala Gly Gly Gly Gly Ser Gly Gly Gly Ser Cys Pro
                450                 455                 460

Asp Leu Val Cys Tyr Thr Asp Tyr Leu Gln Thr Val Ile Cys Ile Leu
465                 470                 475                 480

Glu Met Trp Asn Leu His Pro Ser Thr Leu Thr Leu Thr Trp Gln Asp
                485                 490                 495

Gln Tyr Glu Glu Leu Lys Asp Glu Ala Thr Ser Cys Ser Leu His Arg
                500                 505                 510

Ser Ala His Asn Ala Thr His Ala Thr Tyr Thr Cys His Met Asp Val
                515                 520                 525

Phe His Phe Met Ala Asp Asp Ile Phe Ser Val Asn Ile Thr Asp Gln
                530                 535                 540

Ser Gly Asn Tyr Ser Gln Glu Cys Gly Ser Phe Leu Leu Ala Glu Ser
545                 550                 555                 560

Ile Lys Pro Ala Pro Pro Phe Asn Val Thr Val Thr Phe Ser Gly Gln
                565                 570                 575

Tyr Asn Ile Ser Trp Arg Ser Asp Tyr Glu Asp Pro Ala Phe Tyr Met
                580                 585                 590

Leu Lys Gly Lys Leu Gln Tyr Glu Leu Gln Tyr Arg Asn Arg Gly Asp
                595                 600                 605

Pro Trp Ala Val Ser Pro Arg Arg Lys Leu Ile Ser Val Asp Ser Arg
610                 615                 620

Ser Val Ser Leu Leu Pro Leu Glu Phe Arg Lys Asp Ser Ser Tyr Glu

```
625                 630                 635                 640

Leu Gln Val Arg Ala Gly Pro Met Pro Gly Ser Ser Tyr Gln Gly Thr
                645                 650                 655

Trp Ser Glu Trp Ser Asp Pro Val Ile Phe Gln Thr Gln Ser Glu Glu
                660                 665                 670

Leu Lys Glu
        675
```

<210> SEQ ID NO 44
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

```
Glu Ile Val Leu Thr Gln Ser Pro Ala Thr Leu Ser Leu Ser Pro Gly
1                 5                  10                 15

Glu Arg Ala Thr Leu Ser Cys Arg Ala Ser Gln Ser Val Ser Ser Tyr
                20                  25                 30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                 80

Glu Asp Phe Ala Val Tyr Tyr Cys Gln Gln Ser Ser Asn Trp Pro Arg
                85                  90                 95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 45
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

```
Asp Ile Gln Met Thr Gln Ser Pro Ser Ser Leu Ser Ala Ser Val Gly
1                 5                  10                 15
```

-continued

```
Asp Arg Val Thr Ile Thr Cys Arg Ala Ser Gln Asp Val Ser Thr Ala
        20              25              30

Val Ala Trp Tyr Gln Gln Lys Pro Gly Lys Ala Pro Lys Leu Leu Ile
        35              40              45

Tyr Ser Ala Ser Phe Leu Tyr Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Tyr Leu Tyr His Pro Ala
            85              90              95

Thr Phe Gly Gln Gly Thr Lys Val Glu Ile Lys Arg Thr Val Ala Ala
        100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
        180             185             190

Ala Cys Glu Val Thr His Gln Gly Leu Ser Ser Pro Val Thr Lys Ser
        195             200             205

Phe Asn Arg Gly Glu Cys
    210
```

```
<210> SEQ ID NO 46
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46
```

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Asp Ser
        20              25              30

Trp Ile His Trp Val Arg Gln Ala Pro Gly Lys Gly Leu Glu Trp Val
        35              40              45

Ala Trp Ile Ser Pro Tyr Gly Gly Ser Thr Tyr Tyr Ala Asp Ser Val
    50              55              60

Lys Gly Arg Phe Thr Ile Ser Ala Asp Thr Ser Lys Asn Thr Ala Tyr
65              70              75              80

Leu Gln Met Asn Ser Leu Arg Ala Glu Asp Thr Ala Val Tyr Tyr Cys
            85              90              95

Ala Arg Arg His Trp Pro Gly Gly Phe Asp Tyr Trp Gly Gln Gly Thr
            100             105             110

Leu Val Thr Val Ser Ser Ala Ser Thr Lys Gly Pro Ser Val Phe Pro
        115             120             125

Leu Ala Pro Ser Ser Lys Ser Thr Ser Gly Gly Thr Ala Ala Leu Gly
    130             135             140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445
```

<210> SEQ ID NO 47
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 47

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
```

```
                50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440
```

<210> SEQ ID NO 48
<211> LENGTH: 218
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic polypeptide"

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 49
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95
```

Ala Arg Arg Asp Tyr Arg Phe Asp Met Gly Phe Asp Tyr Trp Gly Gln
        100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
        435                 440                 445

<210> SEQ ID NO 50
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Glu Ile Val Leu Thr Gln Ser Pro Gly Thr Leu Ser Leu Ser Pro Gly

-continued

```
1              5                    10                   15

Glu Arg Ala Thr Leu Ser Cys Arg Ala Ser Gln Ser Val Gly Ser Ser
               20                   25                   30

Tyr Leu Ala Trp Tyr Gln Gln Lys Pro Gly Gln Ala Pro Arg Leu Leu
               35                   40                   45

Ile Tyr Gly Ala Phe Ser Arg Ala Thr Gly Ile Pro Asp Arg Phe Ser
        50                   55                   60

Gly Ser Gly Ser Gly Thr Asp Phe Thr Leu Thr Ile Ser Arg Leu Glu
65                   70                   75                   80

Pro Glu Asp Phe Ala Val Tyr Tyr Cys Gln Gln Tyr Gly Ser Ser Pro
                    85                   90                   95

Trp Thr Phe Gly Gln Gly Thr Lys Val Glu Ile Lys Arg Thr Val Ala
               100                  105                  110

Ala Pro Ser Val Phe Ile Phe Pro Pro Ser Asp Glu Gln Leu Lys Ser
        115                  120                  125

Gly Thr Ala Ser Val Val Cys Leu Leu Asn Asn Phe Tyr Pro Arg Glu
        130                  135                  140

Ala Lys Val Gln Trp Lys Val Asp Asn Ala Leu Gln Ser Gly Asn Ser
145                  150                  155                  160

Gln Glu Ser Val Thr Glu Gln Asp Ser Lys Asp Ser Thr Tyr Ser Leu
                    165                  170                  175

Ser Ser Thr Leu Thr Leu Ser Lys Ala Asp Tyr Glu Lys His Lys Val
               180                  185                  190

Tyr Ala Cys Glu Val Thr His Gln Gly Leu Ser Ser Pro Val Thr Lys
        195                  200                  205

Ser Phe Asn Arg Gly Glu Cys
        210                  215
```

```
<210> SEQ ID NO 51
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (449)..(463)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (464)..(464)
<223> OTHER INFORMATION: /replace=" "
<220> FEATURE:
<221> NAME/KEY: VARIANT
<222> LOCATION: (465)..(465)
<223> OTHER INFORMATION: /replace=" "
<220> FEATURE:
<221> NAME/KEY: SITE
<222> LOCATION: (466)..(480)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (483)..(483)
<223> OTHER INFORMATION: /replace="A"
<220> FEATURE:
<221> NAME/KEY: VARIANT
<222> LOCATION: (515)..(515)
<223> OTHER INFORMATION: /replace="N"
<220> FEATURE:
<221> NAME/KEY: VARIANT
<222> LOCATION: (522)..(522)
```

```
<223> OTHER INFORMATION: /replace="G" or "S" or "T" or "Q" or "E" or "N"
      or "D" or "R" or "K"
<220> FEATURE:
<221> NAME/KEY: VARIANT
<222> LOCATION: (525)..(525)
<223> OTHER INFORMATION: /replace="G" or "S" or "T" or "Q" or "E" or "N"
      or "D" or "R" or "K"
<220> FEATURE:
<221> NAME/KEY: VARIANT
<222> LOCATION: (552)..(552)
<223> OTHER INFORMATION: /replace="G" or "S" or "T" or "Q" or "E" or "N"
      or "D" or "R" or "K"
<220> FEATURE:
<221> NAME/KEY: VARIANT
<222> LOCATION: (553)..(553)
<223> OTHER INFORMATION: /replace="T"
<220> FEATURE:
<221> NAME/KEY: VARIANT
<222> LOCATION: (605)..(605)
<223> OTHER INFORMATION: /replace="S"
<220> FEATURE:
<221> NAME/KEY: SITE
<222> LOCATION: (1)..(613)
<223> OTHER INFORMATION: /note="Variant residues given in the sequence
      have no preference with respect to those in the annotations
      for variant positions"

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Ala
    435                 440                 445

Gly Gly Gly Gly Ser Gly Gly Gly Gly Ser Gly Gly Gly Gly Ser Ala
    450                 455                 460

Ala Gly Gly Gly Gly Ser Gly Gly Gly Gly Ser Gly Gly Gly Gly Ser
465                 470                 475                 480

Ala Pro Asn Ser Ser Ser Thr Lys Lys Thr Gln Leu Gln Leu Glu His
                485                 490                 495

Leu Leu Leu Asp Leu Gln Met Ile Leu Asn Gly Ile Asn Asn Tyr Lys
                500                 505                 510

Asn Pro Lys Leu Thr Arg Met Leu Thr Ala Lys Phe Ala Met Pro Lys
    515                 520                 525

Lys Ala Thr Glu Leu Lys His Leu Gln Cys Leu Glu Glu Glu Leu Lys
    530                 535                 540

Pro Leu Glu Glu Val Leu Asn Ala Ala Gln Ser Lys Asn Phe His Leu
545                 550                 555                 560

Arg Pro Arg Asp Leu Ile Ser Asn Ile Asn Val Ile Val Leu Glu Leu
                565                 570                 575

Lys Gly Ser Glu Thr Thr Phe Met Cys Glu Tyr Ala Asp Glu Thr Ala
    580                 585                 590

Thr Ile Val Glu Phe Leu Asn Arg Trp Ile Thr Phe Ala Gln Ser Ile
    595                 600                 605

Ile Ser Thr Leu Thr
    610
```

<210> SEQ ID NO 52
<211> LENGTH: 673
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
```

-continued

```
                  420              425              430
Leu His Asn His Tyr Thr Gln Lys Ser Leu Ser Leu Ser Pro Gly Ala
        435              440              445
Gly Gly Gly Gly Ser Gly Gly Gly Gly Ser Gly Gly Gly Gly Ser Ile
    450              455              460
Thr Cys Pro Pro Pro Met Ser Val Glu His Ala Asp Ile Trp Val Lys
465              470              475              480
Ser Tyr Ser Leu Tyr Ser Arg Glu Arg Tyr Ile Cys Asn Ser Gly Phe
                485              490              495
Lys Arg Lys Ala Gly Thr Ser Ser Leu Thr Glu Cys Val Leu Asn Lys
            500              505              510
Ala Thr Asn Val Ala His Trp Thr Thr Pro Ser Leu Lys Cys Ile Arg
        515              520              525
Gly Gly Gly Gly Ser Gly Gly Gly Ser Gly Gly Gly Gly Ser Ala Ala
    530              535              540
Gly Gly Gly Gly Ser Gly Gly Gly Gly Ser Gly Gly Gly Gly Ser Asn
545              550              555              560
Trp Val Asn Val Ile Ser Asp Leu Lys Lys Ile Glu Asp Leu Ile Gln
                565              570              575
Ser Met His Ile Asp Ala Thr Leu Tyr Thr Glu Ser Asp Val His Pro
            580              585              590
Ser Cys Lys Val Thr Ala Met Lys Cys Phe Leu Leu Glu Leu Gln Val
        595              600              605
Ile Ser Leu Glu Ser Gly Asp Ala Ser Ile His Asp Thr Val Glu Asp
    610              615              620
Leu Ile Ile Leu Ala Asn Asn Ser Leu Ser Ser Asn Gly Asn Val Thr
625              630              635              640
Glu Ser Gly Cys Lys Glu Cys Glu Glu Leu Glu Glu Lys Asn Ile Lys
            645              650              655
Glu Phe Leu Gln Ser Phe Val His Ile Val Gln Met Phe Ile Asn Thr
        660              665              670
Ser
```

```
<210> SEQ ID NO 53
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (449)..(463)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (464)..(464)
<223> OTHER INFORMATION: /replace=" "
<220> FEATURE:
<221> NAME/KEY: VARIANT
<222> LOCATION: (465)..(465)
<223> OTHER INFORMATION: /replace=" "
<220> FEATURE:
<221> NAME/KEY: SITE
<222> LOCATION: (466)..(480)
<223> OTHER INFORMATION: /note="This region may encompass 0-3 'Gly Gly
      Gly Gly Ser' repeating units"
<220> FEATURE:
<221> NAME/KEY: SITE
<222> LOCATION: (1)..(613)
```

<223> OTHER INFORMATION: /note="Variant residues given in the sequence
      have no preference with respect to those in the annotations
      for variant positions"

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp

```
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Ala
                435                 440                 445

Gly Gly Gly Gly Ser Gly Gly Gly Ser Gly Gly Gly Ser Ala
    450                 455                 460

Ala Gly Gly Gly Ser Gly Gly Gly Ser Gly Gly Gly Gly Ser
465                 470                 475                 480

Gln Gly Gln Asp Arg His Met Ile Arg Met Arg Gln Leu Ile Asp Ile
                485                 490                 495

Val Asp Gln Leu Lys Asn Tyr Val Asn Asp Leu Val Pro Glu Phe Leu
                500                 505                 510

Pro Ala Pro Glu Asp Val Glu Thr Asn Cys Glu Trp Ser Ala Phe Ser
                515                 520                 525

Cys Phe Gln Lys Ala Gln Leu Lys Ser Ala Asn Thr Gly Asn Asn Glu
    530                 535                 540

Arg Ile Ile Asn Val Ser Ile Lys Lys Leu Lys Arg Lys Pro Pro Ser
545                 550                 555                 560

Thr Asn Ala Gly Arg Arg Gln Lys His Arg Leu Thr Cys Pro Ser Cys
                565                 570                 575

Asp Ser Tyr Glu Lys Lys Pro Pro Lys Glu Phe Leu Glu Arg Phe Lys
                580                 585                 590

Ser Leu Leu Gln Lys Met Ile His Gln His Leu Ser Ser Arg Thr His
    595                 600                 605

Gly Ser Glu Asp Ser
    610
```

```
<210> SEQ ID NO 54
<211> LENGTH: 694
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (449)..(463)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (464)..(464)
<223> OTHER INFORMATION: /replace=" "
<220> FEATURE:
<221> NAME/KEY: VARIANT
<222> LOCATION: (465)..(465)
<223> OTHER INFORMATION: /replace=" "
<220> FEATURE:
<221> NAME/KEY: SITE
<222> LOCATION: (466)..(480)
<223> OTHER INFORMATION: /note="This region may encompass 0-3 'Gly Gly
      Gly Gly Ser' repeating units"
<220> FEATURE:
<221> NAME/KEY: SITE
<222> LOCATION: (1)..(694)
<223> OTHER INFORMATION: /note="Variant residues given in the sequence
      have no preference with respect to those in the annotations
      for variant positions"

<400> SEQUENCE: 54
```

```
Gln Val Gln Leu Val Glu Ser Gly Gly Gly Val Val Gln Pro Gly Arg
1               5               10              15

Ser Leu Arg Leu Ser Cys Ala Ala Ser Gly Phe Thr Phe Ser Ser Tyr
            20              25              30

Thr Met His Trp Val Arg Gln Ala Pro Gly Lys Gly Leu Glu Trp Val
        35              40              45

Thr Phe Ile Ser Tyr Asp Gly Asn Asn Lys Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Ile Tyr Tyr Cys
            85              90              95

Ala Arg Thr Gly Trp Leu Gly Pro Phe Asp Tyr Trp Gly Gln Gly Thr
        100             105             110

Leu Val Thr Val Ser Ser Ala Ser Thr Lys Gly Pro Ser Val Phe Pro
        115             120             125

Leu Ala Pro Ser Ser Lys Ser Thr Ser Gly Gly Thr Ala Ala Leu Gly
    130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175

Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
            195             200             205

Asn Thr Lys Val Asp Lys Arg Val Glu Pro Lys Ser Cys Asp Lys Thr
    210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
            245             250             255

Thr Pro Glu Val Thr Cys Val Val Val Asp Val Ser His Glu Asp Pro
        260             265             270

Glu Val Lys Phe Asn Trp Tyr Val Asp Gly Val Glu Val His Asn Ala
        275             280             285

Lys Thr Lys Pro Arg Glu Glu Gln Tyr Asn Ser Thr Tyr Arg Val Val
    290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
            325             330             335

Ile Ser Lys Ala Lys Gly Gln Pro Arg Glu Pro Gln Val Tyr Thr Leu
            340             345             350

Pro Pro Ser Arg Asp Glu Leu Thr Lys Asn Gln Val Ser Leu Thr Cys
            355             360             365

Leu Val Lys Gly Phe Tyr Pro Ser Asp Ile Ala Val Glu Trp Glu Ser
    370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
            405             410             415
```

-continued

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ala
            435                 440                 445

Gly Gly Gly Gly Ser Gly Gly Gly Gly Ser Gly Gly Gly Gly Ser Ala
            450                 455                 460

Ala Gly Gly Gly Gly Ser Gly Gly Gly Gly Ser Gly Gly Gly Gly Ser
465                 470                 475                 480

Ala Val Asn Gly Thr Ser Gln Phe Thr Cys Phe Tyr Asn Ser Arg Ala
                485                 490                 495

Asn Ile Ser Cys Val Trp Ser Gln Asp Gly Ala Leu Gln Asp Thr Ser
            500                 505                 510

Cys Gln Val His Ala Trp Pro Asp Arg Arg Arg Trp Asn Gln Thr Cys
            515                 520                 525

Glu Leu Leu Pro Val Ser Gln Ala Ser Trp Ala Cys Asn Leu Ile Leu
            530                 535                 540

Gly Ala Pro Asp Ser Gln Lys Leu Thr Thr Val Asp Ile Val Thr Leu
545                 550                 555                 560

Arg Val Leu Cys Arg Glu Gly Val Arg Trp Arg Val Met Ala Ile Gln
                565                 570                 575

Asp Phe Lys Pro Phe Glu Asn Leu Arg Leu Met Ala Pro Ile Ser Leu
            580                 585                 590

Gln Val Val His Val Glu Thr His Arg Cys Asn Ile Ser Trp Glu Ile
            595                 600                 605

Ser Gln Ala Ser His Tyr Phe Glu Arg His Leu Glu Phe Glu Ala Arg
            610                 615                 620

Thr Leu Ser Pro Gly His Thr Trp Glu Glu Ala Pro Leu Leu Thr Leu
625                 630                 635                 640

Lys Gln Lys Gln Glu Trp Ile Cys Leu Glu Thr Leu Thr Pro Asp Thr
                645                 650                 655

Gln Tyr Glu Phe Gln Val Arg Val Lys Pro Leu Gln Gly Glu Phe Thr
            660                 665                 670

Thr Trp Ser Pro Trp Ser Gln Pro Leu Ala Phe Arg Thr Lys Pro Ala
            675                 680                 685

Ala Leu Gly Lys Asp Thr
    690
```

```
<210> SEQ ID NO 55
<211> LENGTH: 728
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (449)..(463)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (464)..(464)
<223> OTHER INFORMATION: /replace=" "
<220> FEATURE:
<221> NAME/KEY: VARIANT
<222> LOCATION: (465)..(465)
<223> OTHER INFORMATION: /replace=" "
<220> FEATURE:
<221> NAME/KEY: SITE
<222> LOCATION: (466)..(480)
```

<223> OTHER INFORMATION: /note="This region may encompass 0-3 'Gly Gly
      Gly Gly Ser' repeating units"
<220> FEATURE:
<221> NAME/KEY: SITE
<222> LOCATION: (1)..(728)
<223> OTHER INFORMATION: /note="Variant residues given in the sequence
      have no preference with respect to those in the annotations
      for variant positions"

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

-continued

```
Leu Val Lys Gly Phe Tyr Pro Ser Asp Ile Ala Val Glu Trp Glu Ser
    370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
                405             410             415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Ala
        435             440             445

Gly Gly Gly Gly Ser Gly Gly Gly Gly Ser Gly Gly Gly Gly Ser Ala
    450             455             460

Ala Gly Gly Gly Gly Ser Gly Gly Gly Gly Ser Gly Gly Gly Gly Ser
465             470             475             480

Gln Val Gln Leu Val Gln Ser Gly Ala Glu Val Lys Lys Pro Gly Ser
            485             490             495

Ser Val Lys Val Ser Cys Lys Ala Ser Gly Gly Thr Phe Ser Ser Tyr
            500             505             510

Ala Ile Ser Trp Val Arg Gln Ala Pro Gly Gln Gly Leu Glu Trp Met
        515             520             525

Gly Gly Ile Ile Pro Ile Phe Gly Thr Ala Asn Tyr Ala Gln Lys Phe
    530             535             540

Gln Gly Arg Val Thr Ile Thr Ala Asp Glu Ser Thr Ser Thr Ala Tyr
545             550             555             560

Met Glu Leu Ser Ser Leu Arg Ser Glu Asp Thr Ala Val Tyr Tyr Cys
            565             570             575

Ala Arg Val Asp Arg Tyr Tyr Asn Trp Asn Tyr Phe Leu Gly Ser Phe
            580             585             590

Asp Tyr Trp Gly Gln Gly Thr Leu Val Thr Val Ser Ser Gly Gly Gly
        595             600             605

Gly Ser Gly Gly Gly Gly Ser Gly Gly Gly Gly Ser Ser Tyr Val Leu
    610             615             620

Thr Gln Pro Pro Ser Val Ser Val Ala Pro Gly Lys Thr Ala Arg Ile
625             630             635             640

Thr Cys Gly Gly Asn Asn Ile Arg Ser Lys Ser Val His Trp Tyr Gln
            645             650             655

Gln Lys Pro Gly Gln Ala Pro Val Val Val Ile Tyr Tyr Asp Ser Asp
            660             665             670

Arg Pro Ser Gly Ile Pro Glu Arg Ile Ser Gly Ser Asn Ser Gly Asn
        675             680             685

Thr Ala Thr Leu Thr Ile Ser Arg Val Glu Ala Gly Asp Glu Ala Asp
        690             695             700

Tyr Phe Cys Gln Val Trp Asp Ser Ser Ser Asp His His Val Phe Gly
705             710             715             720

Gly Gly Thr Lys Leu Thr Val Leu
            725
```

<210> SEQ ID NO 56
<211> LENGTH: 728
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

```
<220> FEATURE:
<221> NAME/KEY: SITE
<222> LOCATION: (449)..(463)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (464)..(464)
<223> OTHER INFORMATION: /replace=" "
<220> FEATURE:
<221> NAME/KEY: VARIANT
<222> LOCATION: (465)..(465)
<223> OTHER INFORMATION: /replace=" "
<220> FEATURE:
<221> NAME/KEY: SITE
<222> LOCATION: (466)..(480)
<223> OTHER INFORMATION: /note="This region may encompass 0-3 'Gly Gly
      Gly Gly Ser' repeating units"
<220> FEATURE:
<221> NAME/KEY: SITE
<222> LOCATION: (1)..(728)
<223> OTHER INFORMATION: /note="Variant residues given in the sequence
      have no preference with respect to those in the annotations
      for variant positions"

<400> SEQUENCE: 56

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
```

```
              275                 280                 285
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ala
            435                 440                 445

Gly Gly Gly Gly Ser Gly Gly Gly Gly Ser Gly Gly Gly Gly Ser Ala
    450                 455                 460

Ala Gly Gly Gly Gly Ser Gly Gly Gly Gly Ser Gly Gly Gly Gly Ser
465                 470                 475                 480

Ser Tyr Val Leu Thr Gln Pro Pro Ser Val Ser Val Ala Pro Gly Lys
                485                 490                 495

Thr Ala Arg Ile Thr Cys Gly Gly Asn Asn Ile Arg Ser Lys Ser Val
            500                 505                 510

His Trp Tyr Gln Gln Lys Pro Gly Gln Ala Pro Val Val Val Ile Tyr
            515                 520                 525

Tyr Asp Ser Asp Arg Pro Ser Gly Ile Pro Glu Arg Ile Ser Gly Ser
    530                 535                 540

Asn Ser Gly Asn Thr Ala Thr Leu Thr Ile Ser Arg Val Glu Ala Gly
545                 550                 555                 560

Asp Glu Ala Asp Tyr Phe Cys Gln Val Trp Asp Ser Ser Ser Asp His
                565                 570                 575

His Val Phe Gly Gly Gly Thr Lys Leu Thr Val Leu Gly Gly Gly Gly
            580                 585                 590

Ser Gly Gly Gly Gly Ser Gly Gly Gly Gly Ser Gln Val Gln Leu Val
            595                 600                 605

Gln Ser Gly Ala Glu Val Lys Lys Pro Gly Ser Ser Val Lys Val Ser
    610                 615                 620

Cys Lys Ala Ser Gly Gly Thr Phe Ser Ser Tyr Ala Ile Ser Trp Val
625                 630                 635                 640

Arg Gln Ala Pro Gly Gln Gly Leu Glu Trp Met Gly Gly Ile Ile Pro
                645                 650                 655

Ile Phe Gly Thr Ala Asn Tyr Ala Gln Lys Phe Gln Gly Arg Val Thr
            660                 665                 670

Ile Thr Ala Asp Glu Ser Thr Ser Thr Ala Tyr Met Glu Leu Ser Ser
            675                 680                 685

Leu Arg Ser Glu Asp Thr Ala Val Tyr Tyr Cys Ala Arg Val Asp Arg
    690                 695                 700
```

```
Tyr Tyr Asn Trp Asn Tyr Phe Leu Gly Ser Phe Asp Tyr Trp Gly Gln
705                 710                 715                 720

Gly Thr Leu Val Thr Val Ser Ser
                725

<210> SEQ ID NO 57
<211> LENGTH: 720
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (449)..(463)
<223> OTHER INFORMATION: /note="This region may encompass 0-3 'Gly Gly
      Gly Gly Ser' repeating units"
<220> FEATURE:
<221> NAME/KEY: VARIANT
<222> LOCATION: (464)..(464)
<223> OTHER INFORMATION: /replace=" "
<220> FEATURE:
<221> NAME/KEY: VARIANT
<222> LOCATION: (465)..(465)
<223> OTHER INFORMATION: /replace=" "
<220> FEATURE:
<221> NAME/KEY: SITE
<222> LOCATION: (466)..(480)
<223> OTHER INFORMATION: /note="This region may encompass 0-3 'Gly Gly
      Gly Gly Ser' repeating units"
<220> FEATURE:
<221> NAME/KEY: SITE
<222> LOCATION: (1)..(720)
<223> OTHER INFORMATION: /note="Variant residues given in the sequence
      have no preference with respect to those in the annotations
      for variant positions"

<400> SEQUENCE: 57

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

-continued

```
Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                     230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ala
            435                 440                 445

Gly Gly Gly Gly Ser Gly Gly Gly Gly Ser Gly Gly Gly Gly Ser Ala
        450                 455                 460

Ala Gly Gly Gly Gly Ser Gly Gly Gly Gly Ser Gly Gly Gly Gly Ser
465                 470                 475                 480

Glu Ile Val Leu Thr Gln Ser Pro Gly Thr Leu Ser Leu Ser Pro Gly
                485                 490                 495

Glu Arg Ala Thr Leu Ser Cys Arg Ala Ser Gln Ser Val Ser Ser Ser
            500                 505                 510

Tyr Leu Ala Trp Tyr Gln Gln Lys Pro Gly Gln Ala Pro Arg Leu Leu
            515                 520                 525

Ile Tyr Gly Ala Ser Arg Arg Ala Thr Gly Ile Pro Asp Arg Phe Ser
        530                 535                 540

Gly Ser Gly Ser Gly Thr Asp Phe Thr Leu Thr Ile Ser Arg Leu Glu
545                 550                 555                 560

Pro Glu Asp Phe Ala Val Tyr Tyr Cys Gln Arg Tyr Gly Ser Ser His
                565                 570                 575

Thr Phe Gly Gln Gly Thr Lys Leu Glu Ile Ser Gly Gly Gly Gly Ser
                580                 585                 590

Gly Gly Gly Gly Ser Gly Gly Gly Gly Ser Glu Val Gln Leu Val Gln
        595                 600                 605

Ser Gly Ala Glu Val Lys Lys Pro Gly Glu Ser Leu Lys Ile Ser Cys
```

```
        610                 615                 620

Lys Val Ser Gly Tyr Phe Phe Thr Thr Tyr Trp Ile Gly Trp Val Arg
625                 630                 635                 640

Gln Met Pro Gly Lys Gly Leu Glu Tyr Met Gly Ile Ile Tyr Pro Gly
                645                 650                 655

Asp Ser Asp Thr Arg Tyr Ser Pro Ser Phe Gln Gly Gln Val Thr Ile
                660                 665                 670

Ser Ala Asp Lys Ser Ile Ser Thr Ala Tyr Leu Gln Trp Ser Ser Leu
            675                 680                 685

Lys Ala Ser Asp Thr Ala Met Tyr Tyr Cys Ala Arg Gly Gly Asn Trp
        690                 695                 700

Asn Cys Phe Asp Tyr Trp Gly Gln Gly Thr Leu Val Thr Val Ser Ser
705                 710                 715                 720

<210> SEQ ID NO 58
<211> LENGTH: 683
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Val Asp Val Ser His Glu Asp Pro
            260             265             270

Glu Val Lys Phe Asn Trp Tyr Val Asp Gly Val Glu Val His Asn Ala
            275             280             285

Lys Thr Lys Pro Arg Glu Glu Gln Tyr Asn Ser Thr Tyr Arg Val Val
            290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
            325             330             335

Ile Ser Lys Ala Lys Gly Gln Pro Arg Glu Pro Gln Val Tyr Thr Leu
            340             345             350

Pro Pro Ser Arg Asp Glu Leu Thr Lys Asn Gln Val Ser Leu Thr Cys
            355             360             365

Leu Val Lys Gly Phe Tyr Pro Ser Asp Ile Ala Val Glu Trp Glu Ser
            370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
            405             410             415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Ala
            435             440             445

Gly Gly Gly Gly Ser Gly Gly Gly Gly Ser Ala Ala Gly Gly Gly Gly
            450             455             460

Ser Gly Gly Gly Gly Ser Cys Pro Asp Leu Val Cys Tyr Thr Asp Tyr
465             470             475             480

Leu Gln Thr Val Ile Cys Ile Leu Glu Met Trp Asn Leu His Pro Ser
            485             490             495

Thr Leu Thr Leu Thr Trp Gln Asp Gln Tyr Glu Glu Leu Lys Asp Glu
            500             505             510

Ala Thr Ser Cys Ser Leu His Arg Ser Ala His Asn Ala Thr His Ala
            515             520             525

Thr Tyr Thr Cys His Met Asp Val Phe His Phe Met Ala Asp Asp Ile
            530             535             540

Phe Ser Val Asn Ile Thr Asp Gln Ser Gly Asn Tyr Ser Gln Glu Cys
545             550             555             560

Gly Ser Phe Leu Leu Ala Glu Ser Ile Lys Pro Ala Pro Pro Phe Asn
            565             570             575

Val Thr Val Thr Phe Ser Gly Gln Tyr Asn Ile Ser Trp Arg Ser Asp
            580             585             590

Tyr Glu Asp Pro Ala Phe Tyr Met Leu Lys Gly Lys Leu Gln Tyr Glu
            595             600             605

Leu Gln Tyr Arg Asn Arg Gly Asp Pro Trp Ala Val Ser Pro Arg Arg
            610             615             620

Lys Leu Ile Ser Val Asp Ser Arg Ser Val Ser Leu Leu Pro Leu Glu
625             630             635             640

Phe Arg Lys Asp Ser Ser Tyr Glu Leu Gln Val Arg Ala Gly Pro Met
            645             650             655

Pro Gly Ser Ser Tyr Gln Gly Thr Trp Ser Glu Trp Ser Asp Pro Val
            660             665             670
```

```
Ile Phe Gln Thr Gln Ser Glu Glu Leu Lys Glu
        675                 680

<210> SEQ ID NO 59
<211> LENGTH: 717
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 59

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
            85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
```

-continued

```
              340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ala
        435                 440                 445

Gly Gly Gly Gly Ser Gly Gly Gly Gly Ser Ala Ala Gly Gly Gly Gly
        450                 455                 460

Ser Gly Gly Gly Gly Ser Glu Ile Val Leu Thr Gln Ser Pro Gly Thr
465                 470                 475                 480

Leu Ser Leu Ser Pro Gly Glu Arg Ala Thr Leu Ser Cys Arg Ala Ser
                485                 490                 495

Gln Ser Val Ser Ser Ser Tyr Leu Ala Trp Tyr Gln Gln Lys Pro Gly
            500                 505                 510

Gln Ala Pro Arg Leu Leu Ile Tyr Gly Ala Ser Ser Arg Ala Thr Gly
        515                 520                 525

Ile Pro Asp Arg Phe Ser Gly Ser Gly Ser Gly Thr Asp Phe Thr Leu
        530                 535                 540

Thr Ile Ser Arg Leu Glu Pro Glu Asp Phe Ala Val Tyr Tyr Cys Gln
545                 550                 555                 560

Gln Tyr Gly Ser Trp Thr Phe Gly Gln Gly Thr Lys Val Glu Ile Lys
                565                 570                 575

Gly Gly Gly Gly Ser Gly Gly Gly Gly Ser Gly Gly Gly Gly Ser Gln
            580                 585                 590

Val Gln Leu Val Glu Ser Gly Gly Gly Val Val Gln Pro Gly Arg Ser
        595                 600                 605

Leu Arg Leu Ser Cys Ala Ala Ser Gly Phe Thr Phe Ser Ser Tyr Gly
        610                 615                 620

Met His Trp Val Arg Gln Ala Pro Gly Lys Gly Leu Glu Trp Val Ala
625                 630                 635                 640

Phe Ile Trp Tyr Asp Gly Ser Asp Lys Tyr Tyr Ala Asp Ser Val Lys
                645                 650                 655

Gly Arg Phe Thr Ile Ser Arg Asp Asn Ser Lys Asn Thr Leu Tyr Leu
                660                 665                 670

Gln Met Asn Ser Leu Arg Ala Glu Asp Thr Ala Val Tyr Tyr Cys Ala
            675                 680                 685

Arg Asp Gly Asp Ser Ser Asp Trp Tyr Gly Asp Tyr Tyr Phe Gly Met
        690                 695                 700

Asp Val Trp Gly Gln Gly Thr Thr Val Thr Val Ser Ser
705                 710                 715
```

<210> SEQ ID NO 60
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:

```
          Synthetic polypeptide"

<400> SEQUENCE: 60

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Leu His Trp Val Arg Gln Arg Pro Glu Gln Gly Leu Glu Trp Ile
        35                  40                  45

Gly Arg Ile Asp Pro Ala Asn Gly Asn Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ile Leu Thr Ser Glu Asp Thr Ala Val Tyr Tyr Cys
            85                  90                  95

Ala Ala Arg Phe Gly Tyr Phe Tyr Gly Ser Ser Phe Tyr Ala Val Ala
            100                 105                 110

Tyr Trp Gly Gln Gly Thr Ser Val Thr Val Ser Ser
        115                 120

<210> SEQ ID NO 61
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
            85                  90                  95

Phe Gly Gly Gly Thr Lys Leu Glu Ile Lys
            100                 105

<210> SEQ ID NO 62
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (3)..(3)
<223> OTHER INFORMATION: /replace="A"
<220> FEATURE:
<221> NAME/KEY: VARIANT
<222> LOCATION: (35)..(35)
<223> OTHER INFORMATION: /replace="N"
<220> FEATURE:
```

```
<221> NAME/KEY: VARIANT
<222> LOCATION: (42)..(42)
<223> OTHER INFORMATION: /replace="G" or "S" or "T" or "Q" or "E" or "N"
      or "D" or "R" or "K"
<220> FEATURE:
<221> NAME/KEY: VARIANT
<222> LOCATION: (45)..(45)
<223> OTHER INFORMATION: /replace="G" or "S" or "T" or "Q" or "E" or "N"
      or "D" or "R" or "K"
<220> FEATURE:
<221> NAME/KEY: VARIANT
<222> LOCATION: (72)..(72)
<223> OTHER INFORMATION: /replace="G" or "S" or "T" or "Q" or "E" or "N"
      or "D" or "R" or "K"
<220> FEATURE:
<221> NAME/KEY: VARIANT
<222> LOCATION: (73)..(73)
<223> OTHER INFORMATION: /replace="T"
<220> FEATURE:
<221> NAME/KEY: VARIANT
<222> LOCATION: (125)..(125)
<223> OTHER INFORMATION: /replace="A" or "S"
<220> FEATURE:
<221> NAME/KEY: SITE
<222> LOCATION: (1)..(133)
<223> OTHER INFORMATION: /note="Variant residues given in the sequence
      have no preference with respect to those in the annotations
      for variant positions"

<400> SEQUENCE: 62

Ala Pro Asn Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Ala Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 63
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
                20                  25                  30

Gln Asp Gln Tyr Glu Glu Leu Lys Asp Glu Ala Thr Ser Cys Ser Leu
        35                  40                  45
```

-continued

```
His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
                100                 105                 110

Gly Gln Tyr Asn Ile Ser Trp Arg Ser Asp Tyr Glu Asp Pro Ala Phe
                115                 120                 125

Tyr Met Leu Lys Gly Lys Leu Gln Tyr Glu Leu Gln Tyr Arg Asn Arg
    130                 135                 140

Gly Asp Gly Ser Gly Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
                180                 185                 190

Gly Thr Trp Ser Glu Trp Ser Asp Pro Val Ile Phe Gln Thr Gln Ser
                195                 200                 205

Glu Glu Leu Lys Glu
    210
```

```
<210> SEQ ID NO 64
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64
```

```
Cys Pro Asp Leu Val Cys Tyr Thr Asp Tyr Leu Gln Thr Val Ile Cys
1                   5                   10                  15

Ile Leu Glu Met Trp Asn Leu His Pro Ser Thr Leu Thr Leu Thr Trp
                20                  25                  30

Gln Asp Gln Tyr Glu Glu Leu Lys Asp Glu Ala Thr Ser Cys Ser Leu
                35                  40                  45

His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
                100                 105                 110

Gly Gln Tyr Asn Ile Ser Trp Arg Ser Asp Tyr Glu Asp Pro Ala Phe
                115                 120                 125

Tyr Met Leu Lys Gly Lys Leu Gln Tyr Glu Leu Gln Tyr Arg Asn Arg
    130                 135                 140

Gly Asp Asn Ala Ser Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
```

-continued

```
                 180              185              190

Gly Thr Trp Ser Glu Trp Ser Asp Pro Val Ile Phe Gln Thr Gln Ser
        195              200              205

Glu Glu Leu Lys Glu
        210

<210> SEQ ID NO 65
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Cys Pro Asp Leu Val Cys Tyr Thr Asp Tyr Leu Gln Thr Val Ile Cys
1               5               10              15

Ile Leu Glu Met Trp Asn Leu His Pro Ser Thr Leu Thr Leu Thr Trp
            20              25              30

Gln Asp Gln Tyr Glu Glu Leu Lys Asp Glu Ala Thr Ser Cys Ser Leu
        35              40              45

His Arg Ser Ala His Asn Ala Thr His Ala Thr Tyr Thr Cys His Met
    50              55              60

Asp Val Phe His Phe Met Ala Asp Asp Ile Phe Ser Val Asn Ile Thr
65              70              75              80

Asp Gln Ser Gly Asn Tyr Ser Gln Glu Cys Gly Ser Phe Leu Leu Ala
            85              90              95

Glu Ser Ile Lys Pro Ala Pro Pro Phe Asn Val Thr Val Thr Phe Ser
            100             105             110

Gly Gln Tyr Asn Ile Ser Trp Arg Ser Asp Tyr Glu Asp Pro Ala Phe
            115             120             125

Tyr Met Leu Lys Gly Lys Leu Gln Tyr Glu Leu Gln Tyr Arg Asn Arg
        130             135             140

Gly Asp Asn Gly Ser Val Ser Pro Arg Arg Lys Leu Ile Ser Val Asp
145             150             155             160

Ser Arg Ser Val Ser Leu Leu Pro Leu Glu Phe Arg Lys Asp Ser Ser
            165             170             175

Tyr Glu Leu Gln Val Arg Ala Gly Pro Met Pro Gly Ser Ser Tyr Gln
            180             185             190

Gly Thr Trp Ser Glu Trp Ser Asp Pro Val Ile Phe Gln Thr Gln Ser
        195             200             205

Glu Glu Leu Lys Glu
        210

<210> SEQ ID NO 66
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Cys Pro Asp Leu Val Cys Tyr Thr Asp Tyr Leu Gln Thr Val Ile Cys
1               5               10              15

Ile Leu Glu Met Trp Asn Leu His Pro Ser Thr Leu Thr Leu Thr Trp
            20              25              30
```

```
Gln Asp Gln Tyr Glu Glu Leu Lys Asp Glu Ala Thr Ser Cys Ser Leu
    35                  40                  45

Asn Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
                100                 105                 110

Gly Gln Tyr Asn Ile Ser Trp Arg Ser Asp Tyr Glu Asp Pro Ala Phe
                115                 120                 125

Tyr Met Leu Lys Gly Lys Leu Gln Tyr Glu Leu Gln Tyr Arg Asn Arg
    130                 135                 140

Gly Asp Asn Ala Ser Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
                180                 185                 190

Gly Thr Trp Ser Glu Trp Ser Asp Pro Val Ile Phe Gln Thr Gln Ser
                195                 200                 205

Glu Glu Leu Lys Glu
    210
```

<210> SEQ ID NO 67
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

```
Cys Pro Asp Leu Val Cys Tyr Thr Asp Tyr Leu Gln Thr Val Ile Cys
1                   5                   10                  15

Ile Leu Glu Met Trp Asn Leu His Pro Ser Thr Leu Thr Leu Thr Trp
                20                  25                  30

Gln Asp Gln Tyr Glu Glu Leu Lys Asp Glu Ala Thr Ser Cys Ser Leu
    35                  40                  45

His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
                100                 105                 110

Gly Gln Tyr Asn Ile Ser Trp Arg Ser Asp Tyr Glu Asp Pro Ala Phe
                115                 120                 125

Tyr Met Leu Lys Gly Lys Leu Gln Tyr Glu Leu Gln Tyr Arg Asn Arg
    130                 135                 140

Gly Asp Pro Ser Ala Val Ser Pro Arg Arg Lys Leu Ile Ser Val Asp
145                 150                 155                 160
```

```
Ser Arg Ser Val Ser Leu Leu Pro Leu Glu Phe Arg Lys Asp Ser Ser
            165                 170                 175

Tyr Glu Leu Gln Val Arg Ala Gly Pro Met Pro Gly Ser Ser Tyr Gln
        180                 185                 190

Gly Thr Trp Ser Glu Trp Ser Asp Pro Val Ile Phe Gln Thr Gln Ser
        195                 200                 205

Glu Glu Leu Lys Glu
    210

<210> SEQ ID NO 68
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
            20                  25                  30

Gln Asp Gln Tyr Glu Glu Leu Lys Asp Glu Ala Thr Ser Cys Ser Leu
        35                  40                  45

His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
            100                 105                 110

Gly Gln Tyr Asn Ile Ser Trp Arg Ser Asp Tyr Glu Asp Pro Ala Phe
        115                 120                 125

Tyr Met Leu Lys Gly Lys Leu Gln Tyr Glu Leu Gln Tyr Arg Asn Arg
        130                 135                 140

Gly Asp Pro Ser Gly Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
            165                 170                 175

Tyr Glu Leu Gln Val Arg Ala Gly Pro Met Pro Gly Ser Ser Tyr Gln
        180                 185                 190

Gly Thr Trp Ser Glu Trp Ser Asp Pro Val Ile Phe Gln Thr Gln Ser
        195                 200                 205

Glu Glu Leu Lys Glu
    210

<210> SEQ ID NO 69
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Cys Pro Asp Leu Val Cys Tyr Thr Asp Tyr Leu Gln Thr Val Ile Cys
```

-continued

```
1               5               10              15

Ile Leu Glu Met Trp Asn Leu His Pro Ser Thr Leu Thr Leu Thr Trp
                20              25              30

Gln Asp Gln Tyr Glu Glu Leu Lys Asp Glu Ala Thr Ser Cys Ser Leu
                35              40              45

His Arg Ser Ala His Asn Ala Thr His Ala Thr Tyr Thr Cys His Met
    50              55              60

Asp Val Phe His Phe Met Ala Asp Asp Ile Phe Ser Val Asn Ile Thr
65              70              75              80

Asp Gln Ser Gly Asn Tyr Ser Gln Glu Cys Gly Ser Phe Leu Leu Ala
                85              90              95

Glu Ser Ile Lys Pro Ala Pro Pro Phe Asn Val Thr Val Thr Phe Ser
                100             105             110

Gly Gln Tyr Asn Ile Ser Trp Arg Ser Ala Tyr Glu Asp Pro Ala Phe
                115             120             125

Tyr Met Leu Lys Gly Lys Leu Gln Tyr Glu Leu Gln Tyr Arg Asn Arg
    130             135             140

Gly Asp Gly Ser Gly Val Ser Pro Arg Arg Lys Leu Ile Ser Val Asp
145             150             155             160

Ser Arg Ser Val Ser Leu Leu Pro Leu Glu Phe Arg Lys Asp Ser Ser
                165             170             175

Tyr Glu Leu Gln Val Arg Ala Gly Pro Met Pro Gly Ser Ser Tyr Gln
                180             185             190

Gly Thr Trp Ser Glu Trp Ser Asp Pro Val Ile Phe Gln Thr Gln Ser
                195             200             205

Glu Glu Leu Lys Glu
    210
```

```
<210> SEQ ID NO 70
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70
```

```
Cys Pro Asp Leu Val Cys Tyr Thr Asp Tyr Leu Gln Thr Val Ile Cys
1               5               10              15

Ile Leu Glu Met Trp Asn Leu His Pro Ser Thr Leu Thr Leu Thr Trp
                20              25              30

Gln Asp Gln Tyr Glu Glu Leu Lys Asp Glu Ala Thr Ser Cys Ser Leu
                35              40              45

His Arg Ser Ala His Asn Ala Thr His Ala Thr Tyr Thr Cys His Met
    50              55              60

Asp Val Phe His Phe Met Ala Asp Asp Ile Phe Ser Val Asn Ile Thr
65              70              75              80

Asp Gln Ser Gly Asn Tyr Ser Gln Glu Cys Gly Ser Phe Leu Leu Ala
                85              90              95

Glu Ser Ile Lys Pro Ala Pro Pro Phe Asn Val Thr Val Thr Phe Ser
                100             105             110

Gly Gln Tyr Asn Ile Ser Trp Arg Ser Ile Tyr Glu Asp Pro Ala Phe
                115             120             125

Tyr Met Leu Lys Gly Lys Leu Gln Tyr Glu Leu Gln Tyr Arg Asn Arg
    130             135             140
```

```
Gly Asp Gly Ser Gly Val Ser Pro Arg Arg Lys Leu Ile Ser Val Asp
145             150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
            180                 185                 190

Gly Thr Trp Ser Glu Trp Ser Asp Pro Val Ile Phe Gln Thr Gln Ser
        195                 200                 205

Glu Glu Leu Lys Glu
    210

<210> SEQ ID NO 71
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
            20                  25                  30

Gln Asp Gln Tyr Glu Glu Leu Lys Asp Glu Ala Thr Ser Cys Ser Leu
            35                  40                  45

His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
                100                 105                 110

Gly Gln Tyr Asn Ile Ser Trp Arg Ser Trp Tyr Glu Asp Pro Ala Phe
            115                 120                 125

Tyr Met Leu Lys Gly Lys Leu Gln Tyr Glu Leu Gln Tyr Arg Asn Arg
    130                 135                 140

Gly Asp Gly Ser Gly Val Ser Pro Arg Arg Lys Leu Ile Ser Val Asp
145             150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
            180                 185                 190

Gly Thr Trp Ser Glu Trp Ser Asp Pro Val Ile Phe Gln Thr Gln Ser
        195                 200                 205

Glu Glu Leu Lys Glu
    210

<210> SEQ ID NO 72
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 72

Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
            20                  25                  30

Gln Asp Gln Tyr Glu Glu Leu Lys Asp Glu Ala Thr Ser Cys Ser Leu
        35                  40                  45

His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
                100                 105                 110

Gly Gln Tyr Asn Ile Ser Trp Arg Ser Phe Tyr Glu Asp Pro Ala Phe
                115                 120                 125

Tyr Met Leu Lys Gly Lys Leu Gln Tyr Glu Leu Gln Tyr Arg Asn Arg
        130                 135                 140

Gly Asp Gly Ser Gly Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
            180                 185                 190

Gly Thr Trp Ser Glu Trp Ser Asp Pro Val Ile Phe Gln Thr Gln Ser
            195                 200                 205

Glu Glu Leu Lys Glu
        210

<210> SEQ ID NO 73
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
            20                  25                  30

Gln Asp Gln Tyr Glu Glu Leu Lys Asp Glu Ala Thr Ser Cys Ser Leu
        35                  40                  45

His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
                100                 105                 110

Gly Gln Tyr Asn Ile Ser Trp Arg Ser Tyr Tyr Glu Asp Pro Ala Phe

```
              115                 120                 125

Tyr Met Leu Lys Gly Lys Leu Gln Tyr Glu Leu Gln Tyr Arg Asn Arg
    130                 135                 140

Gly Asp Gly Ser Gly Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
                180                 185                 190

Gly Thr Trp Ser Glu Trp Ser Asp Pro Val Ile Phe Gln Thr Gln Ser
            195                 200                 205

Glu Glu Leu Lys Glu
    210

<210> SEQ ID NO 74
<211> LENGTH: 674
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Gln Val Gln Leu Val Glu Ser Gly Gly Gly Val Val Gln Pro Gly Arg
1                   5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255
```

-continued

```
Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Cys Thr Leu Pro Pro Ser Gln Glu Glu Met Thr
            340                 345                 350

Lys Asn Gln Val Ser Leu Ser Cys Ala Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Val
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Gly Ser Gly Gly Gly
            435                 440                 445

Gly Ser Gly Pro Leu Gly Val Arg Gly Gly Gly Ser Cys Pro Asp
            450                 455                 460

Leu Val Cys Tyr Thr Asp Tyr Leu Gln Thr Val Ile Cys Ile Leu Glu
465                 470                 475                 480

Met Trp Asn Leu His Pro Ser Thr Leu Thr Leu Thr Trp Gln Asp Gln
                485                 490                 495

Tyr Glu Glu Leu Lys Asp Glu Ala Thr Ser Cys Ser Leu His Arg Ser
            500                 505                 510

Ala His Asn Ala Thr His Ala Thr Tyr Thr Cys His Met Asp Val Phe
            515                 520                 525

His Phe Met Ala Asp Asp Ile Phe Ser Val Asn Ile Thr Asp Gln Ser
            530                 535                 540

Gly Asn Tyr Ser Gln Glu Cys Gly Ser Phe Leu Leu Ala Glu Ser Ile
545                 550                 555                 560

Lys Pro Ala Pro Pro Phe Asn Val Thr Val Thr Phe Ser Gly Gln Tyr
                565                 570                 575

Asn Ile Ser Trp Arg Ser Asp Tyr Glu Asp Pro Ala Phe Tyr Met Leu
            580                 585                 590

Lys Gly Lys Leu Gln Tyr Glu Leu Gln Tyr Arg Asn Arg Gly Asp Pro
            595                 600                 605

Trp Ala Val Ser Pro Arg Arg Lys Leu Ile Ser Val Asp Ser Arg Ser
            610                 615                 620

Val Ser Leu Leu Pro Leu Glu Phe Arg Lys Asp Ser Ser Tyr Glu Leu
625                 630                 635                 640

Gln Val Arg Ala Gly Pro Met Pro Gly Ser Ser Tyr Gln Gly Thr Trp
                645                 650                 655

Ser Glu Trp Ser Asp Pro Val Ile Phe Gln Thr Gln Ser Glu Glu Leu
            660                 665                 670
```

Lys Glu

<210> SEQ ID NO 75
<211> LENGTH: 706
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
        210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

```
Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Ala Gly Gly Gly Ser Gly Gly Gly
            435                 440                 445

Gly Ser Gly Pro Leu Gly Val Arg Gly Gly Gly Ser Gly Gly Gly
    450                 455                 460

Gly Ser Glu Ile Val Leu Thr Gln Ser Pro Gly Thr Leu Ser Leu Ser
465                 470                 475                 480

Pro Gly Glu Arg Ala Thr Leu Ser Cys Arg Ala Ser Gln Ser Val Ser
            485                 490                 495

Ser Ser Tyr Leu Ala Trp Tyr Gln Gln Lys Pro Gly Gln Ala Pro Arg
            500                 505                 510

Leu Leu Ile Tyr Gly Ala Ser Arg Arg Ala Thr Gly Ile Pro Asp Arg
            515                 520                 525

Phe Ser Gly Ser Gly Ser Gly Thr Asp Phe Thr Leu Thr Ile Ser Arg
    530                 535                 540

Leu Glu Pro Glu Asp Phe Ala Val Tyr Tyr Cys Gln Arg Tyr Gly Ser
545                 550                 555                 560

Ser His Thr Phe Gly Gln Gly Thr Lys Leu Glu Ile Ser Gly Gly Gly
            565                 570                 575

Gly Ser Gly Gly Gly Gly Ser Gly Gly Gly Gly Ser Glu Val Gln Leu
            580                 585                 590

Val Gln Ser Gly Ala Glu Val Lys Lys Pro Gly Glu Ser Leu Lys Ile
            595                 600                 605

Ser Cys Lys Val Ser Gly Tyr Phe Phe Thr Thr Tyr Trp Ile Gly Trp
            610                 615                 620

Val Arg Gln Met Pro Gly Lys Gly Leu Glu Tyr Met Gly Ile Ile Tyr
625                 630                 635                 640

Pro Gly Asp Ser Asp Thr Arg Tyr Ser Pro Ser Phe Gln Gly Gln Val
            645                 650                 655

Thr Ile Ser Ala Asp Lys Ser Ile Ser Thr Ala Tyr Leu Gln Trp Ser
            660                 665                 670

Ser Leu Lys Ala Ser Asp Thr Ala Met Tyr Tyr Cys Ala Arg Gly Gly
            675                 680                 685

Asn Trp Asn Cys Phe Asp Tyr Trp Gly Gln Gly Thr Leu Val Thr Val
    690                 695                 700

Ser Ser
705
```

```
<210> SEQ ID NO 76
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 76

Thr Tyr Trp Ile Gly
1               5

<210> SEQ ID NO 77
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Ile Ile Tyr Pro Gly Asp Ser Asp Thr Arg Tyr Ser Pro Ser Phe Gln
1               5                   10                  15

Gly

<210> SEQ ID NO 78
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Gly Asn Trp Asn Cys Phe Asp Tyr
1               5

<210> SEQ ID NO 79
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Arg Ala Ser Gln Ser Val Ser Ser Ser Tyr Leu Ala
1               5                   10

<210> SEQ ID NO 80
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gly Ala Ser Arg Arg Ala Thr
1               5

<210> SEQ ID NO 81
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

```
Gln Arg Tyr Gly Ser Ser His Thr
1               5

<210> SEQ ID NO 82
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gly Asn Trp Asn Ser Phe Asp Tyr
1               5

<210> SEQ ID NO 83
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Phe Phe Thr Thr Tyr
            20                  25                  30

Trp Ile Gly Trp Val Arg Gln Met Pro Gly Lys Gly Leu Glu Tyr Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asn Trp Asn Cys Phe Asp Tyr Trp Gly Gln Gly Thr
            100                 105                 110

Leu Val Thr Val Ser Ser
        115

<210> SEQ ID NO 84
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Glu Ile Val Leu Thr Gln Ser Pro Gly Thr Leu Ser Leu Ser Pro Gly
1               5                   10                  15

Arg Glu Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60
```

-continued

```
Gly Ser Gly Ser Gly Thr Asp Phe Thr Leu Thr Ile Ser Arg Leu Glu
65              70              75                      80

Pro Glu Asp Phe Ala Val Tyr Tyr Cys Gln Arg Tyr Gly Ser Ser His
            85              90                  95

Thr Phe Gly Gln Gly Thr Lys Leu Glu Ile Ser Arg Thr Val Ala Ala
            100             105                 110

Pro Ser Val Phe Ile Phe Pro
            115
```